US008318147B2

(12) United States Patent
Klucher et al.

(10) Patent No.: US 8,318,147 B2
(45) Date of Patent: Nov. 27, 2012

(54) USE OF IL-29 FOR TREATING A DENGUE VIRUS INFECTION

(75) Inventors: Kevin M. Klucher, Bellevue, WA (US); Pallavur V Sivakumar, Seattle, WA (US); Wayne R Kindsvogel, Seattle, WA (US); Katherine E Henderson, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/225,741

(22) Filed: Sep. 6, 2011

(65) Prior Publication Data

US 2012/0020919 A1 Jan. 26, 2012

Related U.S. Application Data

(62) Division of application No. 12/608,840, filed on Oct. 29, 2009, now abandoned, which is a division of application No. 11/929,063, filed on Oct. 30, 2007, now abandoned, which is a division of application No. 11/548,487, filed on Oct. 11, 2006, now abandoned, which is a division of application No. 11/531,646, filed on Sep. 13, 2006, now abandoned, which is a division of application No. 10/691,923, filed on Oct. 23, 2003, now Pat. No. 7,135,170.

(60) Provisional application No. 60/420,714, filed on Oct. 23, 2002, provisional application No. 60/463,939, filed on Apr. 18, 2003, provisional application No. 60/420,713, filed on Oct. 23, 2002, provisional application No. 60/463,982, filed on Apr. 18, 2003.

(51) Int. Cl.
*A61K 38/19* (2006.01)
*A61K 38/21* (2006.01)
*A61K 45/00* (2006.01)

(52) U.S. Cl. .......................... 424/85.2; 514/3.7

(58) Field of Classification Search ........................ None
See application file for complete search history.

(56) References Cited

U.S. PATENT DOCUMENTS

| 5,206,344 | A | 4/1993 | Katre et al. |
| 6,927,040 | B2 | 8/2005 | Sheppard et al. |
| 7,038,032 | B2 | 5/2006 | Sheppard et al. |
| 7,135,170 | B2 | 11/2006 | Klucher et al. |
| 2004/0029228 | A1 | 2/2004 | Presnell et al. |
| 2005/0037012 | A1 | 2/2005 | Brady et al. |
| 2005/0244423 | A1 | 11/2005 | Klucher et al. |
| 2007/0015204 | A1 | 1/2007 | Klucher et al. |
| 2007/0048262 | A1 | 3/2007 | Klucher et al. |
| 2007/0053933 | A1 | 3/2007 | Sheppard et al. |
| 2007/0065401 | A1 | 3/2007 | Klucher et al. |
| 2007/0128160 | A1 | 6/2007 | Klucher et al. |
| 2007/0172451 | A1 | 7/2007 | Klucher et al. |
| 2008/0124499 | A1 | 5/2008 | Klucher et al. |

FOREIGN PATENT DOCUMENTS

| EP | 0 032 134 | 7/1981 |
| WO | 02/20569 | 3/2002 |
| WO | 02/086087 | 10/2002 |
| WO | 02/092762 | 11/2002 |
| WO | 03/066002 | 8/2003 |
| WO | 03/089603 | 10/2003 |
| WO | 2004/037995 | 5/2004 |

OTHER PUBLICATIONS

Zompi et al, Viruses 2012, vol. 4, pp. 62-82.*
Kotenko et al., "IFN-λs mediate antiviral protection through a distinct class II cytokine receptor complex," *Nature Immunology* 4(1):69-77, 2003.
Sheppard et al., "IL-28,Il-29 and their class II cytokine receptor IL-28R," *Nature Immunology* 4(1):63-68, 2003.
Langer et al., "The Class II cytokine receptor (CRF2) family: overview and patterns of receptor-ligand interactions," *Cytokine and Growth Factor Reviews* 15:33-48, 2004.
Donnelly et al., "The expanded family of class II cytokines that share the IL-10 receptor-2 (IL-10R2) chain," *J. Leukocyte Biol.* 76:314-321, 2004.
Dumoutier et al., "Role of the Interleukin (IL)–28 Receptor Tyrosine Residues for Antiviral and Antiproliferative Activity of IL-29/Interferon-λ1," *J. Biochem.* 279(31):32269-32274, 2004.
University Calif. Santa Cruz Genome Browser—Chromosome 19, Apr. 20, 2001.
U.S. Appl. No. 11/548,487, filed Oct. 11, 2006, Klucher et al.
University Calif. Santa Cruz Genome Browser Database—Aug. 6, 2001, Accession No. C19001210.
University Calif. Santa Cruz Genome Browser Database—Aug. 6, 2001, Accession No. C19001212.
University Calif. Santa Cruz Genome Browser Database—Aug. 6, 2001, Accession No. C19001213.
University Calif. Santa Cruz Genome Browser Database—Dec. 22, 2001, Accession No. C19001260.
University Calif. Santa Cruz Genome Browser Database—Dec. 22, 2001, Accession No. C19001256. University Calif. Santa Cruz Genome Browser Database—Dec. 22, 2001, Accession No. C19001257.
Ensembl Contig. View Sanger Institute—Apr. 19, 2001, Accession No. AC011445.
Ensembl Contig. View Sanger Institute—Apr. 18, 2000, Accession No. AC018477.
Adams et al., "3,400 expressed sequence tags identify diversity of transcripts from human brain," *Nat. Genet.* 4:256-267, 1993.
GenBank Submission XP-002202436, Oct. 12, 2000.
GenBank Submission XP-002202437, Dec. 12, 1999.
Ben-Nathan et al., "Models of West Nile virus disease", Drug Discovery: Disease Models, vol. 3(10), pp. 49-53 (2006).

* cited by examiner

*Primary Examiner* — Elizabeth C Kemmerer
*Assistant Examiner* — Fozia Hamud
(74) *Attorney, Agent, or Firm* — Bing Hai

(57) ABSTRACT

IL-28A, IL-28B, IL-29, and certain mutants thereof have been shown to have antiviral activity on a spectrum of viral species. Of particular interest is the antiviral activity demonstrated on viruses that infect liver, such as hepatitis B virus and hepatitis C virus. In addition, IL-28A, IL-28B, IL-29, and mutants thereof do not exhibit some of the antiproliferative activity on hematopoietic cells that is observed with interferon treatment. Without the immunosuppressive effects accompanying interferon treatment, IL-28A, IL-28B, and IL-29 will be useful in treating immunocompromised patients for viral infections.

4 Claims, No Drawings

USE OF IL-29 FOR TREATING A DENGUE VIRUS INFECTION

REFERENCE TO RELATED APPLICATIONS

The present application is a divisional of U.S. patent application Ser. No. 12/608,840, filed Oct. 29, 2009, which is a divisional of U.S. patent application Ser. No. 11/929,063, filed Oct. 30, 2007, now abandoned, which is a divisional of U.S. patent application Ser. No. 11/548,487, filed Oct. 11, 2006, now abandoned, which is a divisional of U.S. patent application Ser. No. 11/531,646, filed Sep. 13, 2006, now abandoned, which is a divisional of U.S. patent application Ser. No. 10/691,923, now U.S. Pat. No. 7,135,170, filed Oct. 23, 2003, which claims the benefit of U.S. Provisional Application Ser. No. 60/420,714, filed Oct. 23, 2002, U.S. Provisional Application Ser. No. 60/463,939, filed Apr. 18, 2003, U.S. Provisional Application Ser. No. 60/420,713, filed Oct. 23, 2002, and U.S. Provisional Application Ser. No. 60/463,982, filed Apr. 18, 2003, all of which are herein incorporated by reference.

BACKGROUND OF THE INVENTION

Strategies for treating infectious disease often focus on ways to enhance immunity. For instance, the most common method for treating viral infection involves prophylactic vaccines that induce immune-based memory responses. Another method for treating viral infection includes passive immunization via immunoglobulin therapy (Meissner, *J. Pediatr.* 124:S17-21, 1994). Administration of Interferon alpha (IFN-α) is another method for treating viral infections such as genital warts (Reichman et al., *Ann. Intern. Med.* 108:675-9, 1988) and chronic viral infections like hepatitis C virus (HCV) (Davis et al., *New Engl. J. Med.* 339:1493-9, 1998) and hepatitis B virus (HBV). For instance, IFN-α and IFN-β are critical for inhibiting virus replication (reviewed by Vilcek et al., (Eds.), *Interferons and other cytokines. In Fields Fundamental Virology.*, 3$^{rd}$ ed., Lippincott-Raven Publishers Philadelphia, Pa., 1996, pages 341-365). In response to viral infection, CD4+ T cells become activated and initiate a T-helper type I (TH1) response and the subsequent cascade required for cell-mediated immunity. That is, following their expansion by specific growth factors like the cytokine IL-2, T-helper cells stimulate antigen-specific CD8+ T-cells, macrophages, and NK cells to kill virally infected host cells. Although oftentimes efficacious, these methods have limitations in clinical use. For instance, many viral infections are not amenable to vaccine development, nor are they treatable with antibodies alone. In addition, IFN's are not extremely effective and they can cause significant toxicities; thus, there is a need for improved therapies.

Not all viruses and viral diseases are treated identically because factors, such as whether an infection is acute or chronic and the patient's underlying health, influence the type of treatment that is recommended. Generally, treatment of acute infections in immunocompetent patients should reduce the disease's severity, decrease complications, and decrease the rate of transmission. Safety, cost, and convenience are essential considerations in recommending an acute antiviral agent. Treatments for chronic infections should prevent viral damage to organs such as liver, lungs, heart, central nervous system, and gastrointestinal system, making efficacy the primary consideration.

Chronic hepatitis is one of the most common and severe viral infections of humans worldwide belonging to the Hepadnaviridae family of viruses. Infected individuals are at high risk for developing liver cirrhosis, and eventually, hepatic cancer. Chronic hepatitis is characterized as an inflammatory liver disease continuing for at least six months without improvement. The majority of patients suffering from chronic hepatitis are infected with either chronic HBV, HCV or are suffering from autoimmune disease. The prevalence of HCV infection in the general population exceeds 1% in the United States, Japan, China and Southeast Asia.

Chronic HCV can progress to cirrhosis and extensive necrosis of the liver. Although chronic HCV is often associated with deposition of type I collagen leading to hepatic fibrosis, the mechanisms of fibrogenesis remain unknown. Liver (hepatic) fibrosis occurs as a part of the wound-healing response to chronic liver injury. Fibrosis occurs as a complication of haemochromatosis, Wilson's disease, alcoholism, schistosomiasis, viral hepatitis, bile duct obstruction, toxin exposure, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

There are few effective treatments for hepatitis. For example, treatment of autoimmune chronic hepatitis is generally limited to immunosuppressive treatment with corticosteroids. For the treatment of HBV and HCV, the FDA has approved administration of recombinant IFN-α. However, IFN-α is associated with a number of dose-dependent adverse effects, including thrombocytopenia, leukopenia, bacterial infections, and influenza-like symptoms. Other agents used to treat chronic HBV or HCV include the nucleoside analog RIBAVIRIN™ and ursodeoxycholic acid; however, neither has been shown to be very effective. RIBAVIRIN™+IFN combination therapy for results in 47% rate of sustained viral clearance (Lanford, R. E. and Bigger, C. *Virology* 293: 1-9 (2002). (See Medicine, (D.C. Dale and D. D. Federman, eds.) (Scientific American, Inc., New York), 4:VIII:1-8 (1995)).

Respiratory syncytial virus is the major cause of pneumonia and bronchiolitis in infancy. RSV infects more than half of infants during their first year of exposure, and nearly all are infected after a second year. During seasonal epidemics most infants, children, and adults are at risk for infection or reinfection. Other groups at risk for serious RSV infections include premature infants, immune compromised children and adults, and the elderly. Symptoms of RSV infection range from a mild cold to severe bronchiolitis and pneumonia. Respiratory syncytial virus has also been associated with acute otitis media and RSV can be recovered from middle ear fluid. Herpes simplex virus-1 (HSV-1) and herpes simplex virus-2 (HSV-2) may be either lytic or latent, and are the causative agents in cold sores (HSV-1) and genital herpes, typically associated with lesions in the region of the eyes, mouth, and genitals (HSV-2). These viruses are a few examples of the many viruses that infect humans for which there are few adequate treatments available once infection has occurred.

The demonstrated activities of the IL-28 and IL-29 cytokine family provides methods for treating specific viral infections, in particular, liver specific viral infections. The activity of IL-28 and IL-29 also demonstrate that these cytokines provide methods for treating immunocompromised patients. The methods for these and other uses that should be apparent to those skilled in the art from the teachings herein.

SUMMARY OF THE INVENTION

In one aspect, the present invention provides methods for treating viral infections comprising administering to a mammal with a viral infection causing liver inflammation a therapeutically effective amount of a polypeptide comprising an amino acid sequence that has at least 95% identity to SEQ ID NO:2 from amino acid residue 22 to residue 205, wherein after administration of the polypeptide the viral infection level or liver inflammation is reduced. In other embodiments, the methods comprise administering polypeptide comprising an amino acid sequence as shown in SEQ ID NO:18, SEQ ID NO:24, SEQ ID NO:26, SEQ ID NO:28, SEQ ID NO:30, or SEQ ID NO:36. In other embodiments, the polypeptide is conjugated to a polyalkyl oxide moiety, such as PEG. In another embodiment, a reduction in the viral infection level is measured as a decrease in viral load, an increase in antiviral antibodies, a decrease in serological levels of alanine aminotransferase or histological improvement. In another embodiment, the mammal is a human. In another embodiment, the present invention provides that the viral infection is a hepatitis B virus infection or a hepatitis C virus infection.

In another aspect, the present invention provides methods of treating a viral infection comprising administering to a mammal with a viral infection causing liver inflammation a therapeutically effective amount of polypeptide comprising an amino acid sequence that has at least 95% identity to SEQ ID NO:4 from amino acid residue 20 to residue 200, wherein after administration of the polypeptide the viral infection is reduced. In another embodiments, the polypeptide comprises an amino acid sequence as shown in SEQ ID NO:20, SEQ ID NO:32, SEQ ID NO:34, or SEQ ID NO:38. In another embodiment, the polypeptide is conjugated to a polyalkyl oxide moiety, such as PEG. In another embodiment, the reduction in the viral infection levels is measured as a decrease in viral load, an increase in antiviral antibodies, a decrease in serological levels of alanine aminotransferase or histological improvement. In another embodiment, the mammal is a human. In another embodiment, the viral infection is a hepatitis B virus infection or a hepatitis C virus infection.

In another aspect, the present invention provides methods for treating liver inflammation comprising administering to a mammal in need thereof a therapeutically effective amount of a polypeptide comprising an amino acid sequence that has at least 95% identity to SEQ ID NO:2 from amino acid residue 22 to residue 205, wherein after administration of the polypeptide the liver inflammation is reduced. In one embodiment, the invention provides that the polypeptide comprises an amino acid sequence as shown in SEQ ID NO:18, SEQ ID NO:28, SEQ ID NO:30; SEQ ID NO:24, SEQ ID NO:26 or SEQ ID NO:36. In another embodiment, the polypeptide is conjugated to a polyalkyl oxide moiety, such as PEG. In another embodiment, the present invention provides that the reduction in the liver inflammation is measured as a decrease in serological level of alanine aminotransferase or histological improvement. In another embodiment, the mammal is a human. In another embodiment, the liver inflammation is associated with a hepatitis C virus infection or a hepatitis B virus infection.

In another aspect, the present invention provides methods of treating a viral infection comprising administering to an immunocompromised mammal with an viral infection a therapeutically effective amount of a polypeptide comprising an amino acid sequence that has at least 95% identity to SEQ ID NO:2 from amino acid residue 22 to amino acid residue 205, wherein after administration of the polypeptide the viral infection is reduced. In another embodiment, the polypeptide comprises an amino acid sequence as shown in SEQ ID NO:18, SEQ ID NO:28, SEQ ID NO:30; SEQ ID NO:24, SEQ ID NO:26 or SEQ ID NO:36. In another embodiment, the polypeptide is conjugated to a polyalkyl oxide moiety, such as PEG. In another embodiment, a reduction in the viral infection level is measured as a decrease in viral load, an increase in antiviral antibodies, a decrease in serological levels of alanine aminotransferase or histological improvement. In another embodiment, the mammal is a human. In another embodiment, the present invention provides that the viral infection is a hepatitis B virus infection or a hepatitis C virus infection.

In another aspect, the present invention provides methods of treating a viral infection comprising administering to an immunocompromised mammal with a viral infection a therapeutically effective amount of a polypeptide comprising an amino acid sequence that has at least 95% identity to SEQ ID NO:4 from amino acid residue 20 to residue 200, wherein after administration of the polypeptide the viral infection is reduced. In other embodiments, the polypeptide comprises an amino acid sequence as shown in SEQ ID NO:20, SEQ ID NO:32, SEQ ID NO:34, or SEQ ID NO:38. In another embodiment, the polypeptide is conjugated to a polyalkyl oxide moiety, such as PEG. In another embodiment, the reduction in the viral infection levels is measured as a decrease in viral load, an increase in antiviral antibodies, a decrease in serological levels of alanine aminotransferase or histological improvement. In another embodiment, the mammal is a human. In another embodiment, the viral infection is a hepatitis B virus infection or a hepatitis C virus infection.

In another aspect, the present invention provides methods of treating liver inflammation comprising administering to an immunocompromised mammal with liver inflammation a therapeutically effective amount of a polypeptide comprising an amino acid sequence that has at least 95% identity to SEQ ID NO:2 from amino acid residue 22 to amino acid residue 205, wherein after administration of the polypeptide the liver inflammation is reduced. In another embodiment, the polypeptide comprises an amino acid sequence as shown in SEQ ID NO:18, SEQ ID NO:28, SEQ ID NO:30; SEQ ID NO:24, SEQ ID NO:26 or SEQ ID NO:36. In another embodiment, the polypeptide is conjugated to a polyalkyl oxide moiety, such as PEG. In another embodiment, a reduction in the liver inflammation level is measured as a decrease in serological levels of alanine aminotransferase or histological improvement. In another embodiment, the mammal is a human. In another embodiment, the present invention provides that the viral infection is a hepatitis B virus infection or a hepatitis C virus infection.

In another aspect, the present invention provides methods of treating liver inflammation comprising administering to an immunocompromised mammal with liver inflammation a therapeutically effective amount of a polypeptide comprising an amino acid sequence that has at least 95% identity to SEQ ID NO:4 from amino acid residue 20 to residue 200, wherein after administration of the polypeptide the liver inflammation is reduced. In other embodiments, the polypeptide comprises an amino acid sequence as shown in SEQ ID NO:20, SEQ ID NO:32, SEQ ID NO:34, or SEQ ID NO:38. In another embodiment, the polypeptide is conjugated to a polyalkyl oxide moiety, such as PEG. In another embodiment, the reduction in the liver inflammation is measured as a decrease in serological levels of alanine aminotransferase or histological improvement. In another embodiment, the mammal is a human. In another embodiment, the viral infection is a hepatitis B virus infection or a hepatitis C virus infection.

DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, an increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

"zcyto20", "zcyto21", "zcyto22" are the previous designations for human IL-28A, IL-29, and IL-28B. IL-28A nucleotide and amino acid sequences are shown in SEQ ID NOS: 1, 2, 17, 18, 35, 36. IL-28B nucleotide and amino acid sequences are shown in SEQ ID NOS: 5, 6, 21, 22, 39, 40. IL-29 nucleotide and amino acid sequences are shown in SEQ ID NOS: 3, 4, 19, 20, 37, 38. These sequences are described in PCT application WO 02/086087 and U.S. Provisional Patent Application No. 60/493,194, both commonly assigned to ZymoGenetics, Inc., incorporated herein by reference.

"zcyto24" and "zcyto25" are the previous designations for mouse IL-28A and IL-28B, and are shown in SEQ ID NOS: 7, 8, 9, 10, respectively. The polynucleotide and polypeptides are fully described in PCT application WO 02/086087 commonly assigned to ZymoGenetics, Inc., incorporated herein by reference.

"zcytor19" is the previous designation for IL-28 receptor α-subunit, and is shown in SEQ ID NOS: 11, 12, 13, 14, 15, 16. The polynucleotides and polypeptides are described in PCT application WO 02/20569 on behalf of Schering, Inc., and WO 02/44209 assigned to ZymoGenetics, Inc and incorporated herein by reference. "IL-28 receptor" denotes the IL-28α-subunit and CRF2-4 subunit forming a heterodimeric receptor.

All references cited herein are incorporated by reference in their entirety.

We have previously reported the discovery of a new family of interferon-like molecules in PCT applications, PCT/US01/21087 and PCT/US02/12887, and Sheppard et al., *Nature Immunol.* 4:63-68, 2003; herein all incorporated by reference. This new family includes molecules designated zcyto20 (SEQ ID NOS: 1 and 2; 17 and 18), zcyto21 (SEQ ID NOS:3 and 4; 19 and 20), zcyto22 (SEQ ID NOS:5 and 6; 21 and 22), zcyto24 (SEQ ID NOS:7 and 8), zcyto25 (SEQ ID NOS: 9 and 10), where zcyto20, 21, and 22 are human sequences, and zcyto24 and 25 are mouse sequences. HUGO designations have been assigned to the interferon-like proteins. Zcyto20 has been designated IL-28A, zycto22 has been designated IL-28B, zycto21 has been designated IL-29, and will be referred to by the HUGO names hereafter. Kotenko et al., *Nature Immunol.* 4:69-77, 2003, have identified IL-28A as IFNλ2, IL-28B as IFNλ3, and IL-29 as IFNλ1. The receptor for these proteins, originally designated zcytor19 (SEQ ID NOS: 11 and 12), has been designated as IL-28RA by HUGO.

The present invention provides methods for using IL-28 and IL-29 as an antiviral agent in a broad spectrum of viral infections. In certain embodiments, the methods include using IL-28 and IL-29 in viral infections that are specific for liver, such as hepatitis. Furthermore, data indicate that Il-28 and IL-29 exhibit these antiviral activities without some of the toxicities associated with the use of IFN therapy for viral infection. One of the toxicities related to type I interferon therapy is myelosuppression. This is due to type I interferons suppression of bone marrow progenitor cells. Because IL-29 does not significantly suppress bone marrow cell expansion or B cell proliferation as is seen with IFN-α, IL-29 will have less toxicity associated with treatment. Similar results would be expected with IL-28A and IL-28B.

IFN-α may be contraindicated in some patients, particularly when doses sufficient for efficacy have some toxicity or myelosuppressive effects. Examples of patients for which IFN is contraindicated can include (1) patients given previous immunosuppressive medication, (2) patients with HIV or hemophilia, (3) patients who are pregnant, (4) patients with a cytopenia, such as leukocyte deficiency, neutropenia, thrombocytopenia, and (5) patients exhibiting increased levels of serum liver enzymes. Moreover, IFN therapy is associated with symptoms that are characterized by nausea, vomiting, diarrhea and anorexia. The result being that some populations of patients will not tolerate IFN therapy, and IL-28A, IL-28B, and IL-29 can provide an alternative therapy for some of those patients.

The methods of the present invention comprise administering a therapeutically effective amount of IL-28A, IL-28B, IL-29, or mutant of said molecules that have retained some biological activity associated with IL-28A, IL-28B or IL-29, alone or in combination with other biologics or pharmaceuticals. The present invention provides methods of treating a mammal with a chronic or acute viral infection, causing liver inflammation, thereby reducing the viral infection or liver inflammation. In another aspect, the present invention provides methods of treating liver specific diseases, in particular liver disease where viral infection is in part an etiologic agent. These methods are based on the discovery that IL-28 and IL-29 have antiviral activity on hepatic cells.

As stated above, the methods of the present invention provide administering a therapeutically effective amount of IL-28A, IL-28B, IL-29, or mutant of said molecules that have retained some biological activity associated with IL-28A, IL-28B or IL-29, alone or in combination with other biologics or pharmaceuticals. The present invention provides methods of treatment of a mammal with a viral infection selected from the group consisting of hepatitis A, hepatitis B, hepatitis C, and hepatitis D. Other aspects of the present invention provide methods for using IL-28 or IL-29 as an antiviral agent in viral infections selected from the group consisting of respiratory syncytial virus, herpes virus, Epstein-Barr virus, influenza virus, adenovirus, parainfluenza virus, rhino virus, coxsackie virus, vaccinia virus, west nile virus, dengue virus, venezuelan equine encephalitis virus, pichinde virus and polio virus. In certain embodiments, the mammal can have either a chronic or acute viral infection.

In another aspect, the methods of the present invention also include a method of treating a viral infection comprising administering a therapeutically effective amount of IL-28A, IL-28B, IL-29, or mutant of said molecules that have retained some biological activity associated with IL-28A, IL-28B or IL-29, alone or in combination with other biologics or pharmaceuticals, to an immunompromised mammal with a viral infection, thereby reducing the viral infection, such as is described above. All of the above methods of the present invention can also comprise the administration of zcyto24 or zcyto25 as well.

Description of IL-28A, IL-28B, and IL-29 Polynucleotides and Polypeptides

An IL-28A gene encodes a polypeptide of 205 amino acids, as shown in SEQ ID NO:2. The signal sequence for IL-28A comprises amino acid residue 1 (Met) through amino acid residue 21 (Ala) of SEQ ID NO:2. The mature peptide for IL-28A begins at amino acid residue 22 (Val). A variant IL-28A gene encodes a polypeptide of 200 amino acids, as shown in SEQ ID NO:18. The signal sequence for IL-28A can be predicted as comprising amino acid residue −25 (Met) through amino acid residue −1 (Ala) of SEQ ID NO:18. The mature peptide for IL-28A begins at amino acid residue 1 (Val). IL-28A helices are predicted as follow: helix A is defined by amino acid residues 24 (Leu) to 40 (Glu); helix B by amino acid residues 58 (Thr) to 65 (Gln); helix C by amino acid residues 69 (Arg) to 85 (Ala); helix D by amino acid residues 95 (Val) to 114 (Ala); helix E by amino acid residues 126 (Thr) to 142 (Lys); and helix F by amino acid residues 148 (Cys) to 169 (Ala); as shown in SEQ ID NO: 18. When a polynucleotide sequence encoding the mature polypeptide is expressed in a prokaryotic system, such as *E. coli*, the a secretory signal sequence may not be required and the an N-terminal Met will be present, resulting in expression of a polypeptide such as is shown in SEQ ID NO:36.

The IL-29 gene encodes a polypeptide of 200 amino acids, as shown in SEQ ID NO:4. The signal sequence for IL-29 comprises amino acid residue 1 (Met) through amino acid residue 19 (Ala) of SEQ ID NO:4. The mature peptide for IL-29 begins at amino acid residue 20 (Gly). IL-29 has been described in published PCT application WO 02/02627. A variant IL-29 gene encodes a polypeptide of 200 amino acids, as shown in SEQ ID NO:20, where amino acid residue 169 is Asn instead of Asp. The signal sequence for IL-29 can be predicted as comprising amino acid residue −19 (Met) through amino acid residue −1 (Ala) of SEQ ID NO:20. The mature peptide for IL-29 begins at amino acid residue 1 (Gly). IL-29 has been described in PCT application WO 02/02627. IL-29 helices are predicted as follows: helix A is defined by amino acid residues 30 (Ser) to 44 (Leu); helix B by amino acid residues 57 (Asn) to 65 (Val); helix C by amino acid residues 70 (Val) to 85 (Ala); helix D by amino acid residues 92 (Glu) to 114 (Gln); helix E by amino acid residues 118 (Thr) to 139 (Lys); and helix F by amino acid residues 144 (Gly) to 170 (Leu); as shown in SEQ ID NO: 20. When a polynucleotide sequence encoding the mature polypeptide is expressed in a prokaryotic system, such as *E. coli*, the a secretory signal sequence may not be required and the an N-terminal Met will be present, resulting in expression of a polypeptide such as is shown in SEQ ID NO:38.

The IL-28B gene encodes a polypeptide of 205 amino acids, as shown in SEQ ID NO:6. The signal sequence for IL-28B comprises amino acid residue 1 (Met) through amino acid residue 21 (Ala) of SEQ ID NO:6. The mature peptide for IL-28B begins at amino acid residue 22 (Val). A variant IL-28B gene encodes a polypeptide of 200 amino acids, as shown in SEQ ID NO:22. The signal sequence for IL-28B can be predicted as comprising amino acid residue −21 (Met) through amino acid residue −1 (Ala) of SEQ ID NO:22. The mature peptide for IL-28B begins at amino acid residue 1 (Val). IL-28B helices are predicted as follow: helix A is defined by amino acid residues 8 (Leu) to 41 (Glu); helix B by amino acid residues 58 (Trp) to 65 (Gln); helix C by amino acid residues 69 (Arg) to 86 (Ala); helix D by amino acid residues 95 (Gly) to 114 (Ala); helix E by amino acid residues 126 (Thr) to 142 (Lys); and helix F by amino acid residues 148 (Cys) to 169 (Ala); as shown in SEQ ID NO: 2. When a polynucleotide sequence encoding the mature polypeptide is expressed in a prokaryotic system, such as *E. coli*, the a secretory signal sequence may not be required and the an N-terminal Met will be present, resulting in expression of a polypeptide such as is shown in SEQ ID NO:40.

Zcyto24 gene encodes a polypeptide of 202 amino acids, as shown in SEQ ID NO:8. Zcyto24 secretory signal sequence comprises amino acid residue 1 (Met) through amino acid residue 28 (Ala) of SEQ ID NO:8. An alternative site for cleavage of the secretory signal sequence can be found at amino acid residue 24 (Thr). The mature polypeptide comprises amino acid residue 29 (Asp) to amino acid residue 202 (Val).

Zcyto25 gene encodes a polypeptide of 202 amino acids, as shown in SEQ ID NO:10. Zcyto25 secretory signal sequence comprises amino acid residue 1 (Met) through amino acid residue 28 (Ala) of SEQ ID NO:10. An alternative site for cleavage of the secretory signal sequence can be found at amino acid residue 24 (Thr). The mature polypeptide comprises amino acid residue 29 (Asp) to amino acid residue 202 (Val).

The present invention provides methods comprising administration of polypeptides having mutations in the IL-28 and TL-29 wildtype sequence that result in expression of single forms of the IL-28 or IL-29 molecule. Exemplary mutants are shown in SEQ ID NOS: 24, 28, and 32. When IL-28 and IL-29 are expressed in *E. coli*, an N-terminal Methionine is present. SEQ ID NOS: 26, 30 and 34 show the amino acid residue numbering for IL-28A and IL-29 mutants when the N-terminal Met is present. Table 1 shows the possible combinations of intramolecular disulfide bonded cysteine pairs for wildtype IL-28A, IL-28B, and IL-29.

bers of the same family of cytokines. IL-28RA receptor is a class II cytokine receptor. Class II cytokine receptors usually bind to four-helix-bundle cytokines. For example, interleukin-10 and the interferons bind receptors in this class (e.g., interferon-gamma receptor, alpha and beta chains and the interferon-alpha/beta receptor alpha and beta chains).

Class II cytokine receptors are characterized by the presence of one or more cytokine receptor modules (CRM) in their extracellular domains. Other class II cytokine receptors

TABLE 1

| | | | | | | | | | |
|---|---|---|---|---|---|---|---|---|---|
| IL-28A SEQ ID NO: 18 | $C_{16}$-$C_{115}$ | $C_{48}$-$C_{148}$ | $C_{50}$-$C_{148}$ | $C_{167}$-$C_{174}$ | $C_{16}$-$C_{48}$ | $C_{16}$-$C_{50}$ | $C_{48}$-$C_{115}$ | $C_{50}$-$C_{115}$ | $C_{115}$-$C_{148}$ |
| Met IL-28A SEQ ID NO: 36 | $C_{17}$-$C_{116}$ | $C_{49}$-$C_{149}$ | $C_{51}$-$C_{1498}$ | $C_{168}$-$C_{175}$ | $C_{17}$-$C_{49}$ | $C_{17}$-$C_{51}$ | $C_{49}$-$C_{116}$ | $C_{51}$-$C_{116}$ | $C_{116}$-$C_{149}$ |
| IL-29 SEQ ID NO: 20 | $C_{15}$-$C_{112}$ | $C_{49}$-$C_{145}$ | $C_{112}$-$C_{171}$ | | | | | | |
| Met IL-29 SEQ ID NO: 38 | $C_{16}$-$C_{113}$ | $C_{50}$-$C_{146}$ | $C_{113}$-$C_{172}$ | | | | | | |
| IL-28B SEQ ID NO: 22 | $C_{16}$-$C_{115}$ | $C_{48}$-$C_{148}$ | $C_{50}$-$C_{148}$ | $C_{167}$-$C_{174}$ | $C_{16}$-$C_{48}$ | $C_{16}$-$C_{50}$ | $C_{48}$-$C_{115}$ | $C_{50}$-$C_{115}$ | $C_{115}$-$C_{148}$ |
| Met IL-28B SEQ ID NO: 40 | $C_{17}$-$C_{116}$ | $C_{49}$-$C_{149}$ | $C_{51}$-$C_{1498}$ | $C_{168}$-$C_{175}$ | $C_{17}$-$C_{49}$ | $C_{17}$-$C_{51}$ | $C_{49}$-$C_{116}$ | $C_{51}$-$C_{116}$ | $C_{116}$-$C_{149}$ |

Conjugation of interferons with water-soluble polymers has been shown to enhance the circulating half-life of the interferon, and to reduce the immunogenicity of the polypeptide (see, for example, Nieforth et al., *Clin. Pharmacol. Ther.* 59:636 (1996), and Monkarsh et al., *Anal. Biochem.* 247:434 (1997)). Suitable water-soluble polymers include polyethylene glycol (PEG), monomethoxy-PEG, mono-(C1-C10) alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 40,000. A Cysteine mutant IL-28 or IL-29 conjugate can also comprise a mixture of such water-soluble polymers.

One example of a IL-28 or IL-29 conjugate comprises a IL-28 or IL-29 moiety, or mutant thereof, and a polyalkyl oxide moiety attached to the N-terminus of the IL-28 or IL-29 moiety. PEG is one suitable polyalkyl oxide. As an illustration, IL-28 or IL-29 can be modified with PEG, a process known as "PEGylation." PEGylation of IL-28 or IL-29 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet* 27:290 (1994), and Francis et al., *Int J Hematol* 68:1 (1998)). The methods of the present invention include administration of IL-28, IL-29, and mutants thereof conjugated to water-soluble polymers, such as PEG.

IL-28A, IL-29, IL-28B, zcyto24 and zcyto25, each have been shown to form a complex with the orphan receptor designated zcytor19 (IL-28RA). IL-28RA is described in a commonly assigned patent application PCT/US01/44808. TL-28B, IL-29, zcyto24, and zcyto25 have been shown to bind or signal through IL-28RA as well, further supporting that IL-28A, IL-29, IL-28B, zcyto24 and zcyto25 are members include zcytor11 (commonly owned U.S. Pat. No. 5,965, 704), CRF2-4 (Genbank Accession No. Z17227), IL-10R (Genbank Accession No.s U00672 and NM_001558), DIRS1, zcyto7 (commonly owned U.S. Pat. No. 5,945,511), and tissue factor. IL-28RA, like all known class II receptors except interferon-alpha/beta receptor alpha chain, has only a single class II CRM in its extracellular domain.

Analysis of a human cDNA clone encoding IL-28RA (SEQ ID NO:11) revealed an open reading frame encoding 520 amino acids (SEQ ID NO:12) comprising a secretory signal sequence (residues 1 (Met) to 20 (Gly) of SEQ ID NO:12) and a mature IL-28RA cytokine receptor polypeptide (residues 21 (Arg) to 520 (Arg) of SEQ ID NO:12) an extracellular ligand-binding domain of approximately 206 amino acid residues (residues 21 (Arg) to 226 (Asn) of SEQ ID NO:12), a transmembrane domain of approximately 23 amino acid residues (residues 227 (Trp) to 249 (Trp) of SEQ ID NO:12), and an intracellular domain of approximately 271 amino acid residues (residues 250 (Lys) to 520 (Arg) of SEQ ID NO:12). Within the extracellular ligand-binding domain, there are two fibronectin type III domains and a linker region. The first fibronectin type III domain comprises residues 21 (Arg) to 119 (Tyr) of SEQ ID NO:12, the linker comprises residues 120 (Leu) to 124 (Glu) of SEQ ID NO:12, and the second fibronectin type III domain comprises residues 125 (Pro) to 223 (Pro) of SEQ ID NO:12.

In addition, a human cDNA clone encoding a IL-28RA variant with a 29 amino acid deletion was identified. This IL-28RA variant (as shown in SEQ ID NO:13) comprises an open reading frame encoding 491 amino acids (SEQ ID NO:14) comprising a secretory signal sequence (residues 1 (Met) to 20 (Gly) of SEQ ID NO:14) and a mature IL-28RA cytokine receptor polypeptide (residues 21 (Arg) to 491 (Arg) of SEQ ID NO:14) an extracellular ligand-binding domain of approximately 206 amino acid residues (residues 21 (Arg) to 226 (Asn) of SEQ ID NO:14, a transmembrane domain of approximately 23 amino acid residues (residues 227 (Trp) to 249 (Trp) of SEQ ID NO:14), and an intracellular domain of approximately 242 amino acid residues (residues 250 (Lys) to 491 (Arg) of SEQ ID NO:14).

A truncated soluble form of the IL-28RA receptor mRNA appears to be naturally expressed. Analysis of a human cDNA clone encoding the truncated soluble IL-28RA (SEQ ID NO:15) revealed an open reading frame encoding 211 amino acids (SEQ ID NO:16) comprising a secretory signal sequence (residues 1 (Met) to 20 (Gly) of SEQ ID NO:16) and a mature truncated soluble IL-28RA receptor polypeptide (residues 21 (Arg) to 211 (Ser) of SEQ ID NO:16) a truncated extracellular ligand-binding domain of approximately 143 amino acid residues (residues 21 (Arg) to 163 (Trp) of SEQ ID NO:16), no transmembrane domain, but an additional domain of approximately 48 amino acid residues (residues 164 (Lys) to 211 (Ser) of SEQ ID NO:16).

IL-28RA is a member of the same receptor subfamily as the class II cytokine receptors, and receptors in this subfamily may associate to form homodimers that transduce a signal. Several members of the subfamily (e.g., receptors that bind interferon, IL-10, IL-19, and IL-TIF) combine with a second subunit (termed a β-subunit) to bind ligand and transduce a signal. However, in many cases, specific β-subunits associate with a plurality of specific cytokine receptor subunits. For example, class II cytokine receptors, such as, zcytor11 (U.S. Pat. No. 5,965,704) and CRF2-4 receptor heterodimerize to bind the cytokine IL-TIF (See, WIPO publication WO 00/24758; Dumontier et al., *J. Immunol.* 164:1814-1819, 2000; Spencer, S D et al., *J. Exp. Med.* 187:571-578, 1998; Gibbs, V C and Pennica *Gene* 186:97-101, 1997 (CRF2-4 cDNA); Xie, M E et al., *J. Biol. Chem.* 275: 31335-31339, 2000). IL-10β receptor is believed to be synonymous with CRF2-4 (Dumoutier, L. et al., *Proc. Nat'l. Acad. Sci.* 97:10144-10149, 2000; Liu Y et al, *J. Immunol.* 152; 1821-1829, 1994 (IL-10R cDNA). Therefore, one could expect that zcyto20, zcyto21, zcyto22, zcyto24 and zcyto25 would bind either monomeric, homodimeric, heterodimeric and multimeric zcytor19 receptors. Experimental evidence has identified CRF2-4 as the putative binding partner for IL-28RA.

Examples of biological activity for molecules used to identify IL-28 or IL-29 molecules that are useful in the methods of the present invention include molecules that can bind to the IL-28 receptor with some specificity. Generally, a ligand binding to its cognate receptor is specific when the $K_D$ falls within the range of 100 nM to 100 pM. Specific binding in the range of 100 mM to 10 nM $K_D$ is low affinity binding. Specific binding in the range of 2.5 pM to 100 pM $K_D$ is high affinity binding. In another example, biologically active IL-28 or IL-29 molecules are capable of some level of antiviral activity associated with wildtype IL-28 or IL-29.

Use of IL-28A, IL-28B, and IL-29 for Viral Infections

IL-28 and IL-29 can be used in treating liver specific diseases, in particular liver disease where viral infection is in part an etiologic agent. In particular IL-28 and IL-29 will be used to treat a mammal with a viral infection selected from the group consisting of hepatitis A, hepatitis B, hepatitis C, and hepatitis D. When liver disease is inflammatory and continuing for at least six months, it is generally considered chronic hepatitis. Hepatitis C virus (HCV) patients actively infected will be positive for HCV-RNA in their blood, which is detectable by reverse transcriptase/polymerase chain reaction (RT-PCR) assays. The methods of the present invention will slow the progression of the liver disease. Clinically, diagnostic tests for HCV include serologic assays for antibodies and molecular tests for viral particles. Enzyme immunoassays are available (Vrielink et al., *Transfusion* 37:845-849, 1997), but may require confirmation using additional tests such as an immunoblot assay (Pawlotsky et al., *Hepatology* 27:1700-1702, 1998). Qualitative and quantitative assays generally use polymerase chain reaction techniques, and are preferred for assessing viremia and treatment response (Poynard et al., *Lancet* 352:1426-1432, 1998; McHutchinson et al., *N. Engl. J. Med.* 339:1485-1492, 1998). Several commercial tests are available, such as, quantitative RT-PCR (Amplicor HCV Monitor™, Roche Molecular Systems, Branchburg, N.J.) and a branched DNA (deoxyribonucleic acid) signal amplification assay (Quantiplex™ HCV RNA Assay [bDNA], Chiron Corp., Emeryville, Calif.). A non-specific laboratory test for liver inflammation or necrosis measures alanine aminotransferase level (ALT) and is inexpensive and readily available (National Institutes of Health Consensus Development Conference Panel, *Hepatology* 26 (Suppl. 1):2S-10S, 1997). Histologic evaluation of liver biopsy is generally considered the most accurate means for determining hepatitis progression (Yano et al., *Hepatology* 23:1334-1340, 1996.) For a review of clinical tests for HCV, see, Lauer et al., *N. Engl. J. Med.* 345:41-52, 2001.

There are several in vivo models for testing HBV and HCV that are known to those skilled in art. For example, the effects of IL-28 or IL-29 on mammals infected with HBV can accessed using a woodchuck model. Briefly, woodchucks chronically infected with woodchuck hepatitis virus (WHV) develop hepatitis and hepatocellular carcinoma that is similar to disease in humans chronically infected with HBV. The model has been used for the preclinical assessment of antiviral activity. A chronically infected WHV strain has been established and neonates are inoculated with serum to provide animals for studying the effects of certain compounds using this model. (For a review, see, Tannant et al., *ILAR J.* 42 (2):89-102, 2001). Chimpanzees may also be used to evaluate the effect of IL-28 and IL-29 on HBV infected mammals. Using chimpanzees, characterization of HBV was made and these studies demonstrated that the chimpanzee disease was remarkably similar to the disease in humans (Barker et al., *J. Infect. Dis.* 132:451-458, 1975 and Tabor et al., *J. Infect. Dis.* 147:531-534, 1983.) The chimpanzee model has been used in evaluating vaccines (Prince et al., In: *Vaccines* 97 Cold Spring Harbor Laboratory Press, 1997.) Therapies for HIV are routinely tested using non-human primates infected with simian immunodeficiency viruses (for a review, see, Hirsch et al., *Adv. Pharmcol.* 49:437-477, 2000 and Nathanson et al., *AIDS* 13 (suppl. A):S113-S120, 1999.) For a review of use of non-human primates in HIV, hepatitis, malaria, respiratory syncytial virus, and other diseases, see, Sibal et al., *ILAR J.* 42 (2):74-84, 2001.

Other examples of the types of viral infections for which IL-28A, IL-28B, and IL-29 can be useful include, but are not limited to: infections caused by DNA Viruses (e.g., Herpes Viruses such as Herpes Simplex viruses, Epstein-Barr virus, Cytomegalovirus; Pox viruses such as Variola (small pox) virus; Hepadnaviruses (e.g, Hepatitis B virus); Papilloma viruses; Adenoviruses); RNA Viruses (e.g., HIV I, II; HTLV I, II; Poliovirus; Hepatitis A; Orthomyxoviruses (e.g., Influenza viruses); Paramyxoviruses (e.g., Measles virus); Rabies virus; Hepatitis C); Rhinovirus, Respiratory Syncytial Virus, West Nile Virus, Yellow Fever, Rift Valley Virus, Lassa Fever Virus, Ebola Virus, Lymphocytic Choriomeningitis Virus, which replicates in tissues including liver, and the like. Moreover, examples of the types of diseases for which IL-28 and IL-29 could be used include, but are not limited to: Acquired immunodeficiency; Hepatitis; Gastroenteritis; Hemorrhagic diseases; Enteritis; Carditis; Encephalitis; Paralysis; Brochiolitis; Upper and lower respiratory disease; Respiratory Papillomatosis; Arthritis; Disseminated disease, hepatocellular carcinoma resulting rom chronic Hepatitis C infection. In addition, viral disease in other tissues may be treated with IL-28A, IL-28B, and IL-29, for example viral meningitis, and HIV-related disease. For example, a transgenic model for testing the activity of a therapeutic sample is described in the following examples and described in Money, et al., *Antiviral Ther.*, 3 (Suppl 3):59-68, 1998.

Animal models that are used to test for efficacy in specific viruses are known. For example, Dengue Virus can be tested using a model as such as described in Huang et al., *J. Gen. Virol. September*; 81(Pt 9):2177-82, 2000. West Nile Virus can be tested using the model as described in Xiao et al., *Emerg. Infect. Dis.* July-August; 7(4):714-21, 2001 or Mashimo et al., *Proc. Natl. Acad. Sci. U S A*. August 20;99 (17):11311-6, 2002. Venezuelan equine encephalitis virus model is described in Jackson et al., *Veterinary Pathology*, 28 (5): 410-418, 1991; Vogel et al., *Arch. Pathol. Lab. Med. February*; 120(2):164-72, 1996; Lukaszewski and Brooks, *J. of Virology*, 74(11):5006-5015, 2000. Rhinoviruses models are described in Yin and Lomax, *J. Gen. Virol.* 67 (Pt 11): 2335-40, 1986. Models for respiratory syncytial virus are described in Byrd and Prince, *Clin. Infect. Dis.* 25(6):1363-8, 1997. Other models are known in the art and it is well within the skill of those ordinarily skilled in the art to know how to use such models.

IL-28A, IL-28B, and IL-29 can be used in combination with antiviral agents, including those described above. Some of the more common treatments for viral infection include drugs that inhibit viral replication such as ACYCLOVIR™. In addition, the combined use of some of these agents form the basis for highly active antiretroviral therapy (HAART) used for the treatment of AIDS. Examples in which the combination of immunotherapy (i.e. cytokines) and antiviral drugs shows improved efficacy include the use of interferon plus RIBAVIRIN™ for the treatment of chronic hepatitis C infection (Maddrey, *Semin. Liver. Dis.* 19 Suppl 1:67-75, 1999) and the combined use of IL-2 and HAART (Ross, et al, ibid.) Thus, as IL-28 and IL-29 can stimulate the immune system against disease, it can similarly be used in HAART applications.

In particular, IL-28A, IL-28B, and IL-29 may be useful in monotherapy or combination therapy with IFN-α (with or without RIBAVIRIN™) in patients who do not respond well to IFN therapy. These patients may not respond to IFN therapy due to having less type I interferon receptor on the surface of their cells (Yatsuhashi H, et al., *J Hepatol. Jun.* 30(6):995-1003, 1999; Mathai et al., *J Interferon Cytokine Res.* September 19(9):1011-8, 1999; Fukuda et al., *J. Med. Virol.* 63(3):220-7, 2001). IL-28A, IL-28B, and IL-29 may also be useful in monotherapy or combination therapy with IFN-α (with or without RIBAVIRIN™) in patients who have less type I interferon receptor on the surface of their cells due to down-regulation of the type I interferon receptor after type I interferon treatment (Dupont et al., *J. Interferon Cytokine Res.* 22(4):491-501, 2002).

IL-28 or IL-29 can be used in combination with other immunotherapies including cytokines, immunoglobulin transfer, and various co-stimulatory molecules. In addition to antiviral drugs, IL-28, IL-29, or mutants thereof could be used in combination with any other immunotherapy that is intended to stimulate the immune system. Thus, IL-28, IL-29, or mutants thereof could be used with other cytokines such as Interferon or IL-2. IL-28, IL-29, or mutants thereof could also be added to methods of passive immunization that involve immunoglobulin transfer, one example bring the use of antibodies to treat RSV infection in high risk patients (Meissner HC, ibid.). In addition, IL-28, IL-29, or mutants thereof could be used with additional co-stimulatory molecules such as 4-1BB ligand that recognize various cell surface molecules like CD137 (Tan, J T et al., *J Immunol.* 163:4859-68, 1999).

C. Use of IL-28A, IL-28B, and IL-29 in Immunocompromised Patients

IL-28 and IL-29 can be used as a monotherapy for acute and chronic viral infections and for immunocompromised patients. Methods that enhance immunity can accelerate the recovery time in patients with unresolved infections. Immunotherapies can have an even greater impact on subsets of immunocompromised patients such as the very young or elderly as well as patients that suffer immunodeficiencies acquired through infection, or induced following medical interventions such as chemotherapy or bone marrow ablation. Examples of the types of indications being treated via immune-modulation include; the use of IFN-α for chronic hepatitis (Perry CM, and Jarvis B, *Drugs* 61:2263-88, 2001), the use of IL-2 following HIV infection (Mitsuyasu R., *J. Infect. Dis.* 185 Suppl 2:S115-22, 2002; and Ross R W et al., Expert Opin. Biol. Ther. 1:413-24, 2001), and the use of either IFN-α. (Faro A, *Springer Semin. Immunopathol.* 20:425-36, 1998) for treating Epstein Barr Virus infections following transplantation. Experiments performed in animal models indicate that IL-2 and GM-CSF may also be efficacious for treating EBV related diseases (Baiocchi R A et al., *J. Clin. Invest.* 108:887-94, 2001).

In summary, IL-28, IL-29, or mutants thereof can be used:

as a monotherapy for acute and chronic viral infections and for immunocompromised patients. Methods that enhance immunity can accelerate the recovery time in patients with unresolved infections.

in combination with other antiviral agents such as ACYCLOVIR™, interferon plus RIBAVIRIN™.

in combination with other immunotherapies including cytokines, immunoglobulin transfer, and various co-stimulatory molecules.

to treat a mammal with a chronic or acute viral infection that has resulted liver inflammation, thereby reducing the viral infection and/or liver inflammation. In particular IL-28 and IL-29 will be used to treat a mammal with a viral infection selected from the group consisting of hepatitis A, hepatitis B, hepatitis C, and hepatitis D.

as an antiviral agent in viral infections selected from the group consisting of respiratory syncytial virus, herpes virus, Epstein-Barr virus, influenza virus, adenovirus, parainfluenza virus, rhino virus, coxsackie virus, vaccinia virus, west nile virus, dengue virus, venezuelan equine encephalitis virus, pichinde virus and polio virus.

EXAMPLES

Example 1

Induction of IL-28A, IL-29, IL-28B by Poly I:C and Viral Infection

Freshly isolated human peripheral blood mononuclear cells were grown in the presence of polyinosinic acid-polycytidylic acid (poly I:C; 100 μg/ml) (SIGMA; St. Louis, Mo.), encephalomyocarditis virus (EMCV) with an MOI of 0.1, or in medium alone. After a 15 h incubation, total RNA was isolated from cells and treated with RNase-free DNase. 100 ng total RNA was used as template for one-step RT-PCR using the Superscript One-Step RT-PCR with Platinum Taq kit and gene-specific primers as suggested by the manufacturer (Invitrogen).

Low to undetectable amounts of human IL-28A, IL-28B, and IL-29, IFN-α and IFN-β RNA were seen in untreated cells. In contrast, the amount of IL-28A, IL-29, IL-28B RNA was increased by both poly I:C treatment and viral infection, as was also seen for the type I interferons. These experiments indicate that IL-28A, IL-29, IL-28B, like type I interferons, can be induced by double-stranded RNA or viral infection.

Example 2

IL-28, IL-29 Signaling Activity Compared to IFNα in HepG2 Cells

A. Cell Transfections

HepG2 cells were transfected as follows: 700,000 HepG2 cells/well (6 well plates) were plated approximately 18 h prior to transfection in 2 milliliters DMEM+10% fetal bovine serum. Per well, 1 microgram pISRE-Luciferase DNA (Stratagene) and 1 microgram pIRES2-EGFP DNA (Clontech,) were added to 6 microliters Fugene 6 reagent (Roche Biochemicals) in a total of 100 microliters DMEM. This transfection mix was added 30 minutes later to the pre-plated HepG2 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM+0.5% FBS.

B. Signal Transduction Reporter Assays

The signal transduction reporter assays were done as follows: Following an 18 h incubation at 37° C. in DMEM+0.5% FBS, transfected cells were stimulated with 100 ng/ml IL-28A, IL-29, IL-28B, zcyto24, zcyto25 and huIFN-α2a ligands. Following a 4-hour incubation at 37° degrees, the cells were lysed, and the relative Tight units (RLU) were measured on a luminometer after addition of a luciferase substrate. The results obtained are shown as the fold induction of the RLU of the experimental samples over the medium alone control (RLU of experimental samples/RLU of medium alone=fold induction). Table 2 shows that IL-28A, IL-29, IL-28B, zcyto24 and zcyto25 induce ISRE signaling in human HepG2 liver cells transfected with ISRE-luciferase.

TABLE 2

Fold Induction of Cytokine-dependent ISRE Signaling in HepG2 Cells

| Cytokine | Fold Inductn. |
|---|---|
| IL-28A | 5.6 |
| IL-29 | 4 |
| IL-28B | 5.8 |
| Zcyto24 | 4.7 |
| Zcyto25 | 3 |
| HuIFN-a2a | 5.8 |

Example 3

IL-29 Antiviral Activity Compared to IFNα in HepG2 Cells

An antiviral assay was adapted for EMCV (American Type Culture Collection # VR-129B, Manassas, Va.) with human cells (Familletti, P., et al., *Methods Enzym.* 78: 387-394, 1981). Cells were plated with cytokines and incubated 24 hours prior to challenge by EMCV at a multiplicity of infection of 0.1 to 1. The cells were analyzed for viability with a dye-uptake bioassay 24 hours after infection (Berg, K., et al., *Apmis* 98: 156-162, 1990). Target cells were given MTT and incubated at 37° C. for 2 hours. A solubiliser solution was added, incubated overnight at 37° C. and the optical density at 570 nm was determined. OD570 is directly proportional to antiviral activity.

The results show the antiviral activity when IL-29 and IFN on were tested with HepG2 cells: IL-29, IFNβ and IFN α-2a were added at varying concentration to HepG2 cells prior to EMCV infection and dye-uptake assay. The mean and standard deviation of the OD570 from triplicate wells is plotted. OD570 is directly proportional to antiviral activity. For IL-29, the EC50 was 0.60 ng/ml; for IFN-α2a, the EC50 was 0.57 ng/ml; and for IFN-β, the EC50 was 0.46 ng/ml.

Example 4

IL-28RA mRNA Expression in Liver and Lymphocyte Subsets

In order to further examine the mRNA distribution for IL-28RA, semi-quantitative RT-PCR was performed using the SDS 7900HT system (Applied Biosystems, CA). One-step RT-PCR was performed using 100 ng total RNA for each sample and gene-specific primers. A standard curve was generated for each primer set using Bjab RNA and all sample values were normalized to HPRT. The normalized results are summarized in Tables 2-4. The normalized values for IFNAR2 and CRF2-4 are also shown.

Table 3: B and T cells express significant levels of IL-28RA mRNA. Low levels are seen in dendritic cells and most monocytes.

TABLE 3

| Cell/Tissue | IL-28RA | IFNAR2 | CRF2-4 |
|---|---|---|---|
| Dendritic Cells unstim | .04 | 5.9 | 9.8 |
| Dendritic Cells + IFNg | .07 | 3.6 | 4.3 |
| Dendritic Cells | .16 | 7.85 | 3.9 |
| CD14+ stim'd with LPS/IFNg | .13 | 12 | 27 |
| CD14+ monocytes resting | .12 | 11 | 15.4 |
| Hu CD14+ Unact. | 4.2 | TBD | TBD |
| Hu CD14+ 1 ug/ml LPS act. | 2.3 | TBD | TBD |
| H. Inflamed tonsil | 3 | 12.4 | 9.5 |
| H. B-cells + PMA/Iono 4 & 24 hrs | 3.6 | 1.3 | 1.4 |
| Hu CD19+ resting | 6.2 | TBD | TBD |
| Hu CD19+ 4 hr. PMA/Iono | 10.6 | TBD | TBD |
| Hu CD19+ 24 hr Act. PMA/Iono | 3.7 | TBD | TBD |
| IgD+ B-cells | 6.47 | 13.15 | 6.42 |
| IgM+ B-cells | 9.06 | 15.4 | 2.18 |
| IgD− B-cells | 5.66 | 2.86 | 6.76 |
| NKCells + PMA/Iono | 0 | 6.7 | 2.9 |
| Hu CD3+ Unactivated | 2.1 | TBD | TBD |
| CD4+ resting | .9 | 8.5 | 29.1 |
| CD4+ Unstim 18 hrs | 1.6 | 8.4 | 13.2 |
| CD4+ + Poly I/C | 2.2 | 4.5 | 5.1 |
| CD4+ + PMA/Iono | .3 | 1.8 | .9 |
| CD3 neg resting | 1.6 | 7.3 | 46 |
| CD3 neg unstim 18 hrs | 2.4 | 13.2 | 16.8 |
| CD3 neg + Poly VC 18 hrs | 5.7 | 7 | 30.2 |
| CD3 neg + LPS 18 hrs | 3.1 | 11.9 | 28.2 |
| CD8+ unstim 18 hrs | 1.8 | 4.9 | 13.1 |
| CD8+ stim'd with PMA/Ion 18 hrs | .3 | .6 | 1.1 |

As shown in Table 4, normal liver tissue and liver derived cell lines display substantial levels of IL-28RA and CRF2-4 mRNA.

TABLE 4

| Cell/Tissue | IL-28RA | IFNAR2 | CRF2-4 |
|---|---|---|---|
| HepG2 | 1.6 | 3.56 | 2.1 |
| HepG2 UGAR 5/10/02 | 1.1 | 1.2 | 2.7 |
| HepG2, CGAT HKES081501C | 4.3 | 2.1 | 6 |
| HuH7 5/10/02 | 1.63 | 16 | 2 |
| HuH7 hepatoma - CGAT | 4.2 | 7.2 | 3.1 |
| Liver, normal - CGAT #HXYZ020801K | 11.7 | 3.2 | 8.4 |
| Liver, NAT—Normal adjacent tissue | 4.5 | 4.9 | 7.7 |

TABLE 4-continued

| Cell/Tissue | IL-28RA | IFNAR2 | CRF2-4 |
|---|---|---|---|
| Liver, NAT—Normal adjacent tissue | 2.2 | 6.3 | 10.4 |
| Hep SMVC hep vein | 0 | 1.4 | 6.5 |
| Hep SMCA hep. Artery | 0 | 2.1 | 7.5 |
| Hep. Fibro | 0 | 2.9 | 6.2 |
| Hep. Ca. | 3.8 | 2.9 | 5.8 |
| Adenoca liver | 8.3 | 4.2 | 10.5 |
| SK-Hep-1 adenoca. Liver | .1 | 1.3 | 2.5 |
| AsPC-1 Hu. Pancreatic adenocarc. | .7 | .8 | 1.3 |
| Hu. Hep. Stellate cells | .025 | 4.4 | 9.7 |

As shown in Table 5, primary airway epithelial cells contain abundant levels of IL-28RA and CRF2-4.

TABLE 5

| Cell/Tissue | IL-28RA | IFNAR2 | CRF2-4 |
|---|---|---|---|
| U87MG - glioma | 0 | .66 | .99 |
| NHBE unstim | 1.9 | 1.7 | 8.8 |
| NHBE + TNF-alpha | 2.2 | 5.7 | 4.6 |
| NHBE + poly I/C | 1.8 | nd | nd |
| Small Airway Epithelial Cells | 3.9 | 3.3 | 27.8 |
| NHLF—Normal human lung fibroblasts | 0 | nd | nd |

As shown in Table 6, IL-28RA is present in normal and diseased liver specimens, with increased expression in tissue from Hepatitis C and Hepatitis B infected specimens.

TABLE 6

| Cell/Tissue | IL-28RA | CRF2-4 | IFNAR2 |
|---|---|---|---|
| Liver with Coagulation Necrosis | 8.87 | 15.12 | 1.72 |
| Liver with Autoimmune Hepatitis | 6.46 | 8.90 | 3.07 |
| Neonatal Hepatitis | 6.29 | 12.46 | 6.16 |
| Endstage Liver disease | 4.79 | 17.05 | 10.58 |
| Fulminant Liver Failure | 1.90 | 14.20 | 7.69 |
| Fulminant Liver failure | 2.52 | 11.25 | 8.84 |
| Cirrhosis, primary biliary | 4.64 | 12.03 | 3.62 |
| Cirrhosis Alcoholic (Laennec's) | 4.17 | 8.30 | 4.14 |
| Cirrhosis, Cryptogenic | 4.84 | 7.13 | 5.06 |
| Hepatitis C+, with cirrhosis | 3.64 | 7.99 | 6.62 |
| Hepatitis C+ | 6.32 | 11.29 | 7.43 |
| Fulminant hepatitis secondary to Hep A | 8.94 | 21.63 | 8.48 |
| Hepatitis C+ | 7.69 | 15.88 | 8.05 |
| Hepatitis B+ | 1.61 | 12.79 | 6.93 |
| Normal Liver | 8.76 | 5.42 | 3.78 |
| Normal Liver | 1.46 | 4.13 | 4.83 |
| Liver NAT | 3.61 | 5.43 | 6.42 |
| Liver NAT | 1.97 | 10.37 | 6.31 |
| Hu Fetal Liver | 1.07 | 4.87 | 3.98 |
| Hepatocellular Carcinoma | 3.58 | 3.80 | 3.22 |
| Adenocarcinoma Liver | 8.30 | 10.48 | 4.17 |
| hep. SMVC, hep. Vein | 0.00 | 6.46 | 1.45 |
| Hep SMCA hep. Artery | 0.00 | 7.55 | 2.10 |
| Hep. Fibroblast | 0.00 | 6.20 | 2.94 |
| HuH7 hepatoma | 4.20 | 3.05 | 7.24 |
| HepG2 Hepatocellular carcinoma | 3.40 | 5.98 | 2.11 |
| SK-Hep-1 adenocar. Liver | 0.03 | 2.53 | 1.30 |
| HepG2 Unstim | 2.06 | 2.98 | 2.28 |
| HepG2 + zcyto21 | 2.28 | 3.01 | 2.53 |
| HepG2 + IFNα | 2.61 | 3.05 | 3.00 |
| Normal Female Liver - degraded | 1.38 | 6.45 | 4.57 |
| Normal Liver - degraded | 1.93 | 4.99 | 6.25 |
| Normal Liver - degraded | 2.41 | 2.32 | 2.75 |
| Disease Liver - degraded | 2.33 | 3.00 | 6.04 |
| Primary Hepatocytes from Clonetics | 9.13 | 7.97 | 13.30 |

As shown in Tables 7-11, IL-28RA is detectable in normal B cells, B lymphoma cell lines, T cells, T lymphoma cell lines (Jurkat), normal and transformed lymphocytes (B cells and T cells) and normal human monocytes.

TABLE 7

| | HPRT Mean | IL-28RA Mean | IL-28RA norm | IFNAR2 | IFNR2 norm | CRF2-4 | CRF2-4 Norm |
|---|---|---|---|---|---|---|---|
| CD14+ 24 hr unstim #A38 | 13.1 | 68.9 | 5.2 | 92.3 | 7.0 | 199.8 | 15.2 |
| CD14+ 24 hr stim #A38 | 6.9 | 7.6 | 1.1 | 219.5 | 31.8 | 276.6 | 40.1 |
| CD14+ 24 hr unstim #A112 | 17.5 | 40.6 | 2.3 | 163.8 | 9.4 | 239.7 | 13.7 |
| CD14+ 24 hr stim #A112 | 11.8 | 6.4 | 0.5 | 264.6 | 22.4 | 266.9 | 22.6 |
| CD14+ rest #X | 32.0 | 164.2 | 5.1 | 1279.7 | 39.9 | 699.9 | 21.8 |
| CD14+ + LPS #X | 21.4 | 40.8 | 1.9 | 338.2 | 15.8 | 518.0 | 24.2 |
| CD14+ 24 hr unstim #A39 | 26.3 | 86.8 | 3.3 | 297.4 | 11.3 | 480.6 | 18.3 |
| CD14+ 24 hr stim #A39 | 16.6 | 12.5 | 0.8 | 210.0 | 12.7 | 406.4 | 24.5 |
| HL60 Resting | 161.2 | 0.2 | 0.0 | 214.2 | 1.3 | 264.0 | 1.6 |
| HL60 + PMA | 23.6 | 2.8 | 0.1 | 372.5 | 15.8 | 397.5 | 16.8 |
| U937 Resting | 246.7 | 0.0 | 0.0 | 449.4 | 1.8 | 362.5 | 1.5 |
| U937 + PMA | 222.7 | 0.0 | 0.0 | 379.2 | 1.7 | 475.9 | 2.1 |
| Jurkat Resting | 241.7 | 103.0 | 0.4 | 327.7 | 1.4 | 36.1 | 0.1 |
| Jurkat Activated | 130.7 | 143.2 | 1.1 | | | | |
| Colo205 | 88.8 | 43.5 | 0.5 | | | | |
| HT-29 | 26.5 | 30.5 | 1.2 | | | | |

TABLE 8

| | HPRT SD | IL-28RA SD |
|---|---|---|
| Mono 24 hr unstim #A38 | 0.6 | 2.4 |
| Mono 24 hr stim #A38 | 0.7 | 0.2 |
| Mono 24 hr unstim #A112 | 2.0 | 0.7 |
| Mono 24 hr stim +#A112 | 0.3 | 0.1 |
| Mono rest #X | 5.7 | 2.2 |
| Mono + LPS #X | 0.5 | 1.0 |
| Mono 24 hr unstim #A39 | 0.7 | 0.8 |
| Mono 24 hr stim #A39 | 0.1 | 0.7 |
| HL60 Resting | 19.7 | 0.1 |
| HL60 + PMA | 0.7 | 0.4 |
| U937 Resting | 7.4 | 0.0 |
| U937 + PMA | 7.1 | 0.0 |
| Jurkat Resting | 3.7 | 1.1 |
| Jurkat Activated | 2.4 | 1.8 |

TABLE 8-continued

|  | HPRT SD | IL-28RA SD |
|---|---|---|
| Colo205 | 1.9 | 0.7 |
| HT-29 | 2.3 | 1.7 |

TABLE 9

|  | Mean Hprt | Mean IFNAR2 | Mean IL-28RA | Mean CRF |
|---|---|---|---|---|
| CD3+/CD4+ 0 | 10.1 | 85.9 | 9.0 | 294.6 |
| CD4/CD3+ Unstim 18 hrs | 12.9 | 108.7 | 20.3 | 170.4 |
| CD4+/CD3+ + Poly I/C 18 hrs | 24.1 | 108.5 | 52.1 | 121.8 |
| CD4+/CD3+ + PMA/Iono 18 hrs | 47.8 | 83.7 | 16.5 | 40.8 |
| CD3 neg 0 | 15.4 | 111.7 | 24.8 | 706.1 |
| CD3 neg unstim 18 hrs | 15.7 | 206.6 | 37.5 | 263.0 |
| CD3 neg + Poly I/C 18 hrs | 9.6 | 67.0 | 54.7 | 289.5 |
| CD3 neg + LPS 18 hrs | 14.5 | 173.2 | 44.6 | 409.3 |
| CD8+ Unstim. 18 hrs | 6.1 | 29.7 | 11.1 | 79.9 |
| CD8+ + PMA/Iono 18 hrs | 78.4 | 47.6 | 26.1 | 85.5 |
| 12.8.1 - NHBE Unstim | 47.4 | 81.1 | 76.5 | 415.6 |
| 12.8.2 - NHBE + TNF-alpha | 42.3 | 238.8 | 127.7 | 193.9 |
| SAEC | 15.3 | 49.9 | 63.6 | 426.0 |

TABLE 10

|  | IL-28RA Norm | CRF Norm | IFNAR2 Norm | IL-28RA SD | CRF SD | IFNAR2 SD |
|---|---|---|---|---|---|---|
| CD3+/CD4+ 0 | 0.9 | 29.1 | 8.5 | 0.1 | 1.6 | 0.4 |
| CD4/CD3+ Unstim 18 hrs | 1.6 | 13.2 | 8.4 | 0.2 | 1.6 | 1.4 |
| CD4+/CD3+ + Poly I/C 18 hrs | 2.2 | 5.1 | 4.5 | 0.1 | 0.3 | 0.5 |
| CD4+/CD3+ + PMA/Iono 18 hrs | 0.3 | 0.9 | 1.8 | 0.0 | 0.1 | 0.3 |
| CD3 neg 0 | 1.6 | 46.0 | 7.3 | 0.2 | 4.7 | 1.3 |
| CD3 neg unstim 18 hrs | 2.4 | 16.8 | 13.2 | 0.4 | 2.7 | 2.3 |
| CD3 neg + Poly I/C 18 hrs | 5.7 | 30.2 | 7.0 | 0.3 | 1.7 | 0.8 |
| CD3 neg + LPS 18 hrs | 3.1 | 28.2 | 11.9 | 0.4 | 5.4 | 2.9 |
| CD8+ Unstim. 18 hrs | 1.8 | 13.1 | 4.9 | 0.1 | 1.1 | 0.3 |
| CD8+ + PMA/Iono 18 hrs | 0.3 | 1.1 | 0.6 | 0.0 | 0.1 | 0.0 |
| 12.8.1 - NHBE Unstim | 1.6 | 8.8 | 1.7 | 0.1 | 0.4 | 0.1 |
| 12.8.2 - NHBE + TNF-alpha | 3.0 | 4.6 | 5.7 | 0.1 | 0.1 | 0.1 |
| SAEC | 4.1 | 27.8 | 3.3 | 0.2 | 1.1 | 0.3 |

TABLE 11

|  | SD Hprt | SD IFNAR2 | SD IL-28RA | SD CRF |
|---|---|---|---|---|
| CD3+/CD4+ 0 | 0.3 | 3.5 | 0.6 | 12.8 |
| CD4/CD3+ Unstim 18 hrs | 1.4 | 13.7 | 1.1 | 8.5 |
| CD4+/CD3+ + Poly I/C 18 hrs | 1.3 | 9.8 | 1.6 | 3.4 |
| CD4+/CD3+ + PMA/Iono 18 hrs | 4.0 | 10.3 | 0.7 | 3.7 |
| CD3 neg 0 | 1.4 | 16.6 | 1.6 | 28.6 |
| CD3 neg unstim 18 hrs | 2.4 | 16.2 | 2.7 | 12.6 |
| CD3 neg + Poly I/C 18 hrs | 0.5 | 7.0 | 1.0 | 8.3 |
| CD3 neg + LPS 18 hrs | 1.0 | 39.8 | 5.6 | 73.6 |
| CD8+ Unstim. 18 hrs | 0.2 | 1.6 | 0.5 | 6.1 |
| CD8+ + PMA/Iono 18 hrs | 1.3 | 1.7 | 0.2 | 8.1 |
| 12.8.1 - NHBE Unstim | 2.4 | 5.6 | 2.7 | 2.8 |
| 12.8.2 - NHBE + TNF-alpha | 0.5 | 3.4 | 3.5 | 3.4 |
| SAEC | 0.5 | 4.8 | 1.8 | 9.9 |

Example 5

Mouse IL-28 Does Not Effect Daudi Cell Proliferation

Human Daudi cells were suspended in RPMI+10% FBS at 50,000 cells/milliliter and 5000 cells were plated per well in a 96 well plate. IL-29-CEE (IL-29 conjugated with glu tag), IFN-γ or IFN-α2a was added in 2-fold serial dilutions to each well. IL-29-CEE was used at a concentration range of from 1000 ng/ml to 0.5 ng/ml. IFN-γ was used at a concentration range from 125 ng/ml to 0.06 ng/ml. IFN-α2a was used at a concentration range of from 62 ng/ml to 0.03 ng/ml. Cells were incubated for 72 h at 37° C. After 72 h. Alamar Blue (Accumed, Chicago, Ill.) was added at 20 microliters/well. Plates were further incubated at 37° C., 5% CO, for 24 hours. Plates were read on the Fmax™ plate reader (Molecular Devices, Sunnyvale, Calif.) using the SoftMax™ Pro program, at wavelengths 544 (Excitation) and 590 (Emission). Alamar Blue gives a fluorometric readout based on the metabolic activity of cells, and is thus a direct measurement of cell proliferation in comparison to a negative control. The results indicate that IL-29-CEE, in contrast to IFN-α2a, has no significant effect on proliferation of Daudi cells.

Example 6

Mouse IL-28 Does Not Have Antiproliferative Effect on Mouse B cells

Mouse B cells were isolated from 2 Balb/C spleens (7 months old) by depleting CD43+ cells using MACS magnetic beads. Purified B cells were cultured in vitro with LPS, anti-IgM or anti-CD40 monoclonal antibodies. Mouse IL-28 or mouse IFNα was added to the cultures and $^3$H-thymidine was added at 48 hrs. and $^3$H-thymidine incorporation was measured after 72 hrs. culture.

IFNα at 10 ng/ml inhibited $^3$H-thymidine incorporation by mouse B cells stimulated with either LPS or anti-IgM. However mouse IL-28 did not inhibit $^3$H-thymidine incorporation at any concentration tested including 1000 ng/ml. In contrast, both mIFNα and mouse IL-28 increased $^3$H thymidine incorporation by mouse B cells stimulated with anti-CD40 MAb.

These data demonstrate that mouse IL-28 unlike IFNα displays no antiproliferative activity even at high concentrations. In addition, zcyto24 enhances proliferation in the presence of anti-CD40 MAbs. The results illustrate that mouse IL-28 differs from IFNα in that mouse IL-28 does not display antiproliferative activity on mouse B cells, even at high concentrations. In addition, mouse IL-28 enhances proliferation in the presence of anti-CD40 monoclonal antibodies.

Example 7

Bone Marrow Expansion Assay

Fresh human marrow mononuclear cells (Poietic Technologies, Gaithersburg, Md.) were adhered to plastic for 2 hrs in αMEM, 10% FBS, 50 micromolar β-mercaptoethanol, 2 ng/ml FLT3L at 37° C. Non adherent cells were then plated at 25,000 to 45,000 cells/well (96 well tissue culture plates) in αMEM, 10% FBS, 50 micromolar β-mercaptoethanol, 2 ng/ml FLT3L in the presence or absence of 1000 ng/ml IL-29-

CEE, 100 ng/ml IL-29-CEE, 10 ng/ml IL-29-CEE, 100 ng/ml IFN-α2a, 10 ng/ml IFN-α2a or 1 ng/ml α2a. These cells were incubated with a variety of cytokines to test for expansion or differentiation of hematopoietic cells from the marrow (20 ng/ml IL-2, 2 ng/ml IL-3, 20 ng/ml IL-4, 20 ng/ml IL-5, 20 ng/ml IL-7, 20 ng/ml IL-10, 20 ng/ml IL-12, 20 ng/ml IL-15, 10 ng/ml IL-21 or no added cytokine). After 8 to 12 days Alamar Blue (Accumed, Chicago, Ill.) was added at 20 microliters/well. Plates were further incubated at 37° C., 5% CO, for 24 hours. Plates were read on the Finax™ plate reader (Molecular Devices Sunnyvale, Calif.) using the SoftMax™ Pro program, at wavelengths 544 (Excitation) and 590 (Emission). Alamar Blue gives a fluourometric readout based on the metabolic activity of cells, and is thus a direct measurement of cell proliferation in comparison to a negative control.

IFN-α2a caused a significant inhibition of bone marrow expansion under all conditions tested. In contrast, IL-29 had no significant effect on expansion of bone marrow cells in the presence of IL-3, IL-4, IL-5, IL-7, IL-10, IL-12, IL-21 or no added cytokine. A small inhibition of bone marrow cell expansion was seen in the presence of IL-2 or IL-15.

Example 8

Inhibition of IL-28 and IL-29 Signaling with Soluble Receptor (zcytor19/CRF2-4)
A. Signal Transduction Reporter Assay A signal transduction reporter assay can be used to show the inhibitor properties of zcytor19-Fc4 homodimeric and zcytor19-Fc/CRF2-4-Fc heterodimeric soluble receptors on zcyto20, zcyto21 and zcyto24 signaling. Human embryonal kidney (FMK) cells overexpressing the zcytor19 receptor are transfected with a reporter plasmid containing an interferon-stimulated response element (ISRE) driving transcription of a luciferase reporter gene. Luciferase activity following stimulation of transfected cells with ligands (including zcyto20 (SEQ ID NO:18), zcyto21 (SEQ ID NO:20), zcyto24 (SEQ ID NO:8)) reflects the interaction of the ligand with soluble receptor.
B. Cell Transfections 293 HEK cells overexpressing zcytor19 were transfected as follows: 700,000 293 cells/well (6 well plates) were plated approximately 18 h prior to transfection in 2 milliliters DMEM+10% fetal bovine serum. Per well, 1 microgram pISRE-Luciferase DNA (Stratagene) and 1 microgram pIRES2-EGFP DNA (Clontech,) were added to 6 microliters Eugene 6 reagent (Roche Biochemicals) in a total of 100 microliters DMEM. This transfection mix was added 30 minutes later to the pre-plated 293 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM 0.5% FBS.
C. Signal Transduction Reporter Assays The signal transduction reporter assays were done as follows: Following an 18 h incubation at 37° C. in DMEM 0.5% FBS, transfected cells were stimulated with 10 ng/ml zcyto20, zcyto21 or zcyto24 and 10 micrograms/ml of the following soluble receptors; human zcytor19-Fc homodimer, human zcytor19-Fc/human CRF2-4-Fc heterodimer, human CRF2-4-Fc homodimer, murine zcytor19-Ig homodimer. Following a 4-hour incubation at 37° C., the cells were lysed, and the relative light units (RLU) were measured on a luminometer after addition of a luciferase substrate. The results obtained are shown as the percent inhibition of ligand-induced signaling in the presence of soluble receptor relative to the signaling in the presence of PBS alone. Table 11 shows that the human zcytor19-Fc/human CRF2-4 heterodimeric soluble receptor is able to inhibit zcyto20, zcyto21 and zcyto24-induced signaling between 16 and 45% of control.

The human zcytor19-Fc homodimeric soluble receptor is also able to inhibit zcyto21-induced signaling by 45%. No significant effects were seen with huCRF2-4-Fc or muzcytor19-Ig homodimeric soluble receptors.

TABLE 12

Percent Inhibition of Ligand-induced Interferon Stimulated Response Element (ISRE) Signaling by Soluble Receptors

| Ligand | Huzcytor19-Fc/huCRF2-4-Fc | Huzcytor19-Fc | HuCRF2-4-Fc | Muzcytor19-Ig |
|---|---|---|---|---|
| Zcyto20 | 16% | 92% | 80% | 91% |
| Zcyto21 | 16% | 45% | 79% | 103% |
| Zcyto24 | 47% | 90% | 82% | 89% |

Example 9

IL-28 and IL-29 Inhibit HIV Replication in Fresh Human PBMCs

Human immunodeficiency virus (HIV) is a pathogenic retrovirus that infects cells of the immune system. CD4 T cells and monocytes are the primary infected cell types. To test the ability of IL-28 and IL-29 to inhibit HIV replication in vitro, PBMCs from normal donors were infected with the HIV virus in the presence of IL-28, IL-29 and MetIL-29C172S-PEG.

Fresh human peripheral blood mononuclear cells (PBMCs) were isolated from whole blood obtained from screened donors who were seronegative for HIV and HBV. Peripheral blood cells were pelleted/washed 2-3 times by low speed centrifugation and resuspended in PBS to remove contaminating platelets. The washed blood cells were diluted 1:1 with Dulbecco's phosphate buffered saline (D-PBS) and layered over 14 mL of Lymphocyte Separation Medium ((LSM; Cellgro™ by Mediatech, Inc. Herndon, Va.); density 1.078+/−0.002 g/ml) in a 50 mL centrifuge tube and centrifuged for 30 minutes at 600×G. Banded PBMCs were gently aspirated from the resulting interface and subsequently washed 2× in PBS by low speed centrifugation. After the final wash, cells were counted by trypan blue exclusion and resuspended at $1\times10^7$ cells/mL in RPMI 1640 supplemented with 15% Fetal Bovine Serum (FBS), 2 mM L-glutamine, 4 μg/mL PHA-P. The cells were allowed to incubate for 48-72 hours at 37° C. After incubation, PBMCs were centrifuged and resuspended in RPMI 1640 with 15% FBS, 2 mM L-glutamine, 100 U/mL penicillin, 100 μg/mL streptomycin, 10 μg/mL gentamycin, and 20 U/mL recombinant human IL-2. PBMCs were maintained in the medium at a concentration of $1\text{-}2\times10^6$ cells/mL with biweekly medium changes until used in the assay protocol. Monocytes were depleted from the culture as the result of adherence to the tissue culture flask.

For the standard PBMC assay, PHA-P stimulated cells from at least two normal donors were pooled, diluted in fresh medium to a final concentration of $1\times10^6$ cells/mL, and plated in the interior wells of a 96 well round bottom microplate at 50 μL/well ($5\times10^4$ cells/well). Test dilutions were prepared at a 2× concentration in microtiter tubes and 100 μL of each concentration was placed in appropriate wells in a standard format. IL-28, IL-29 and MetIL-29C172S-PEG were added at concentrations from 0-10 μg/ml, usually in 1/2 log dilutions. 50 μL of a predetermined dilution of virus stock was placed in each test well (final MOI of 0.1). Wells with only cells and virus added were used for virus control. Separate plates were prepared identically without virus for drug cytotoxicity studies using an MTS assay system. The PBMC cultures were maintained for seven days following infection, at which time cell-free supernatant samples were collected and assayed for reverse transcriptase activity and p24 antigen levels.

A decrease in reverse transcriptase activity or p24 antigen levels with IL-28, IL-29 and MetIL-29C172S-PEG would be indicators of antiviral activity. Result would demonstrate that IL-28 and IL-29 may have therapeutic value in treating HIV and AIDS.

Example 10

IL-28 and IL-29 Inhibit GBV-B Replication in Marmoset Liver Cells

HCV is a member of the Flaviviridae family of RNA viruses. HCV does not replicate well in either ex-vivo or in vitro cultures and therefore, there are no satisfactory systems to test the anti-HCV activity of molecules in vitro. GB virus B (GBV-B) is an attractive surrogate model for use in the development of anti-HCV antiviral agents since it has a relatively high level of sequence identity with HCV and is a hepatotropic virus. To date, the virus can only be grown in the primary hepatocytes of certain non-human primates. This is accomplished by either isolating hepatocytes in vitro and infecting them with GBV-B, or by isolating hepatocytes from GBV-B infected marmosets and directly using them with antiviral compounds.

The effects of IL-28, IL-29 and MetIL-29C172S-PEG are assayed on GBV-B extracellular RNA production by TaqMan RT-PCR and on cytotoxicity using CellTiter96® reagent (Promega, Madison, Wis.) at six half-log dilutions IL-28, IL-29 or MetIL-29C172S-PEG polypeptide in triplicate. Untreated cultures serve as the cell and virus controls. Both RIBAVIRIN® (200 μg/ml at the highest test concentration) and IFN-α (5000 IU/ml at the highest test) are included as positive control compounds. Primary hepatocyte cultures are isolated and plated out on collagen-coated plates. The next day the cultures are treated with the test samples (IL-28, IL-29, MetIL-29C172S-PEG, IFNα, or RIBAVIRIN®) for 24 hr before being exposed to GBV-B virions or treated directly with test samples when using in vivo infected hepatocytes. Test samples and media are added the next day, and replaced three days later. Three to four days later (at day 6-7 post test sample addition) the supernatant is collected and the cell numbers quantitated with CellTiter96®: Viral RNA is extracted from the supernatant and quantified with triplicate replicates in a quantitative TaqMan RT-PCR assay using an in vitro transcribed RNA containing the RT-PCR target as a standard. The average of replicate samples is computed. Inhibition of virus production is assessed by plotting the average RNA and cell number values of the triplicate samples relative to the untreated virus and cell controls. The inhibitory concentration of drug resulting in 50% inhibition of GBV-B RNA production (IC50) and the toxic concentration resulting in destruction of 50% of cell numbers relative to control values (TC50) are calculated by interpolation from graphs created with the data.

Inhibition of the GBV-B RNA production by IL-28 and 29 is an indication of the antiviral properties of IL-28 and IL-29 on this Hepatitis C-like virus on hepatocytes, the primary organ of infection of Hepatitis C, and positive results suggest that IL-28 or IL-29 may be useful in treating HCV infections in humans.

Example 11

IL-28, IL-29 and MetIL-29C172S-PEG Inhibit HBV Replication in WT10 Cells

Chronic hepatitis B (HBV) is one of the most common and severe viral infections of humans belonging to the Hepadnaviridae family of viruses. To test the antiviral activities of IL-28 and IL-29 against HBV, IL-28, IL-29 and MetIL-29C172S-PEG were tested against HBV in an in vitro infection system using a variant of the human liver line HepG2. IL-28, IL-29 and MetIL-29C172S-PEG inhibited viral replication in this system, suggesting therapeutic value in treating HBV in humans.

WT10 cells are a derivative of the human liver cell line HepG2 2.2.15. WT10 cells are stably transfected with the HBV genome, enabling stable expression of HBV transcripts in the cell line (Fu and Cheng, *Antimicrobial Agents Chemother.* 44(12):3402-3407, 2000). In the WT10 assay the drug in question and a 3TC control will be assayed at five concentrations each, diluted in a half-log series. The endpoints are TaqMan PCR for extracellular HBV DNA (IC50) and cell numbers using CellTiter96 reagent (TC50). The assay is similar to that described by Korba et al. *Antiviral Res.* 15(3):217-228, 1991 and Korba et al., *Antiviral Res.* 19(1): 55-70, 1992. Briefly, WT10 cells are plated in 96-well microtiter plates. After 16-24 hours the confluent monolayer of HepG2-2.2.15 cells is washed and the medium is replaced with complete medium containing varying concentrations of a test samples in triplicate. 3TC is used as the positive control, while media alone is added to cells as a negative control (virus control, VC). Three days later the culture medium is replaced with fresh medium containing the appropriately diluted test samples. Six days following the initial addition of the test compound, the cell culture supernatant is collected, treated with pronase and DNAse, and used in a real-time quantitative TaqMan PCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability which is used to calculate toxicity ($TC_{50}$). The therapeutic index (TI) is calculated as $TC_{50}/IC_{50}$.

IL-28, IL-29 and MetIL-29C172S-PEG inhibited HepB viral replication in WT10 cells with an IC50<0.032 ug/ml. This demonstrates antiviral activity of IL-28 and IL-29 against HBV grown in liver cell lines, providing evidence of therapeutic value for treating HBV in human patients.

Example 12

IL-28, IL-29 and MetIL-29C172S-PEG Inhibit BVDV Replication in Bovine Kidney Cells HCV is a member of the Flaviviridae family of RNA viruses. Other viruses belonging to this family are the bovine viral diarrhea virus (BVDV) and yellow fever virus (YFV). HCV does not replicate well in either ex vivo or in vitro cultures and therefore there are no systems to test anti-HCV activity in vitro. The BVDV and YFV assays are used as surrogate viruses for HCV to test the antiviral activities against the Flavivirida family of viruses.

The antiviral effects of IL-28, IL-29 and MetIL-29C172S-PEG were assessed in inhibition of cytopathic effect assays (CPE). The assay measured cell death using Madin-Darby bovine kidney cells (MDBK) after infection with cytopathic BVDV virus and the inhibition of cell death by addition of IL-28, IL-29 and MetIL-29C172S-PEG. The MDBK cells were propagated in Dulbecco's modified essential medium (DMEM) containing phenol red with 10% horse serum, 1% glutamine and 1% penicillin-streptomycin. CPE inhibition assays were performed in DMEM without phenol red with 2% FBS, 1% glutamine and 1% Pen-Strep. On the day preceding the assays, cells were trypsinized (1% trypsin-EDTA), washed, counted and plated out at $10^4$ cells/well in a 96-well flat-bottom BioCoat® plates (Fisher Scientific, Pittsburgh, Pa.) in a volume of 100 μl/well. The next day, the medium was removed and a pre-titered aliquot of virus was added to the cells. The amount of virus was the maximum dilution that would yield complete cell killing (>80%) at the time of maximal CPE development (day 7 for BVDV). Cell viability was determined using a CellTiter96® reagent (Promega) according to the manufacturer's protocol, using a Vmax plate reader (Molecular Devices, Sunnyvale, Calif.). Test samples were tested at six concentrations each, diluted in assay medium in a half-log series. IfNα and RIBAVIRIN® were used as positive controls. Test sample were added at the time of viral infection. The average background and sample color-corrected data for percent CPE reduction and percent cell viability at each concentration were determined relative to controls and the $IC_{50}$ calculated relative to the $TC_{50}$.

IL-28, IL-29 and MetIL-29C172S-PEG inhibited cell death induced by BVDV in MDBK bovine kidney cells. IL-28 inhibited cell death with an $IC_{50}$ of 0.02 μg/ml, IL-29 inhibited cell death with an $IC_{50}$ of 0.19 μg/ml, and MetIL-29C172S-PEG inhibited cell death with an $IC_{50}$ of 0.45 μg/ml. This demonstrated that IL-28 and IL-29 have antiviral activity against the Flavivirida family of viruses.

Example 13

Induction of Interferon Stimulated Genes by IL-28 and IL-29

A. Human Peripheral Blood Mononuclear Cells

Freshly isolated human peripheral blood mononuclear cells were grown in the presence of IL-29 (20 ng/mL), IFNα₂a (2 ng/ml) (PBL Biomedical Labs, Piscataway, N.J.), or in medium alone. Cells were incubated for 6, 24, 48, or 72 hours, and then total RNA was isolated and treated with RNase-free DNase. 100 ng total RNA was used as a template for One-Step Semi-Quantitative RT-PCR® using Taqman One-Step RT-PCR Master Mix® Reagents and gene specific primers as suggested by the manufacturer. (Applied Biosystems, Branchburg, N.J.) Results were normalized to HPRT and are shown as the fold induction over the medium alone control for each time-point. Table 13 shows that IL-29 induces Interferon Stimulated Gene Expression in human peripheral blood mononuclear cells at all time-points tested.

TABLE 13

|  | MxA Fold induction | Pkr Fold Induction | OAS Fold Induction |
| --- | --- | --- | --- |
| 6 hr IL29 | 3.1 | 2.1 | 2.5 |
| 6 hr IFNα2a | 17.2 | 9.6 | 16.2 |
| 24 hr IL29 | 19.2 | 5.0 | 8.8 |
| 24 hr IFNα2a | 57.2 | 9.4 | 22.3 |
| 48 hr IL29 | 7.9 | 3.5 | 3.3 |
| 48 hr IFNα2a | 18.1 | 5.0 | 17.3 |
| 72 hr IL29 | 9.4 | 3.7 | 9.6 |
| 72 hr IFNα2a | 29.9 | 6.4 | 47.3 |

B. Activated Human T Cells

Human T cells were isolated by negative selection from freshly harvested peripheral blood mononuclear cells using the Pan T-cell Isolation® kit according to manufacturer's instructions (Miltenyi, Auburn, Calif.). T cells were then activated and expanded for 5 days with plate-bound anti-CD3, soluble anti-CD28 (0.5 ug/ml), (Pharmingen, San Diego, Calif.) and Interleukin 2 (IL-2; 100 U/ml) (R&D Systems, Minneapolis, Minn.), washed and then expanded for a further 5 days with IL-2. Following activation and expansion, cells were stimulated with IL-28A (20 ng/ml), IL-29 (20 ng/ml), or medium alone for 3, 6, or 18 hours. Total RNA was isolated and treated with RNase-Free DNase. One-Step Semi-Quantitative RT-PCR® was performed as described in the example above. Results were normalized to HPRT and are shown as the fold induction over the medium alone control for each time-point. Table 14 shows that IL-28 and IL-29 induce Interferon Stimulated Gene expression in activated human T cells at all time-points tested.

TABLE 14

|  | MxA Fold Induction | Pkr Fold Induction | OAS Fold Induction |
| --- | --- | --- | --- |
| Donor #1 3 hr IL28 | 5.2 | 2.8 | 4.8 |
| Donor #1 3 hr IL29 | 5.0 | 3.5 | 6.0 |
| Donor #1 6 hr IL28 | 5.5 | 2.2 | 3.0 |
| Donor #1 6 hr IL29 | 6.4 | 2.2 | 3.7 |
| Donor #1 18 hr IL28 | 4.6 | 4.8 | 4.0 |
| Donor #1 18 hr IL29 | 5.0 | 3.8 | 4.1 |
| Donor #2 3 hr IL28 | 5.7 | 2.2 | 3.5 |
| Donor #2 3 hr IL29 | 6.2 | 2.8 | 4.7 |
| Donor #2 6 hr IL28 | 7.3 | 1.9 | 4.4 |
| Donor #2 6 hr IL29 | 8.7 | 2.6 | 4.9 |
| Donor #2 18 hr IL28 | 4.7 | 2.3 | 3.6 |
| Donor #2 18 hr IL29 | 4.9 | 2.1 | 3.8 |

C. Primary Human Hepatocytes

Freshly isolated human hepatocytes from two separate donors (Cambrex, Baltimore, Md. and CellzDirect, Tucson, Ariz.) were stimulated with IL-28A (50 ng/ml), IL-29 (50 ng/ml), IFNα₂a (50 ng/ml), or medium alone for 24 hours. Following stimulation, total RNA was isolated and treated with RNase-Free DNase. One-step semi-quantitative RT-PCR was performed as described previously in the example above. Results were normalized to HPRT and are shown as the fold induction over the medium alone control for each time-point. Table 15 shows that IL-28 and IL-29 induce Interferon Stimulated Gene expression in primary human hepatocytes following 24-hour stimulation.

TABLE 15

|  | MxA Fold Induction | Pkr Fold Induction | OAS Fold Induction |
| --- | --- | --- | --- |
| Donor #1 IL28 | 31.4 | 6.4 | 30.4 |
| Donor #1 IL29 | 31.8 | 5.2 | 27.8 |
| Donor #1 IFN-α2a | 63.4 | 8.2 | 66.7 |
| Donor #2 IL28 | 41.7 | 4.2 | 24.3 |
| Donor #2 IL29 | 44.8 | 5.2 | 25.2 |
| Donor #2 IFN-α2a | 53.2 | 4.8 | 38.3 |

D. HepG2 and HuH7: Human Liver Hepatoma Cell Lines

HepG2 and HuH7 cells (ATCC NOS. 8065, Manassas, Va.) were stimulated with IL-28A (10 ng/ml), IL-29 (10 ng/ml), IFNα₂a (10 ng/ml), IFNB (1 ng/ml) (PBL Biomedical, Piscataway, N.J.), or medium alone for 24 or 48 hours. In a separate culture, HepG2 cells were stimulated as described above with 20 ng/ml of MetIL-29C172S-PEG or MetIL-29-PEG. Total RNA was isolated and treated with RNase-Free DNase. 100 ng Total RNA was used as a template for one-step semi-quantitative RT-PCR as described previously. Results were normalized to HPRT and are shown as the fold induction over the medium alone control for each time-point. Table 16 shows that IL-28 and IL-29 induce ISG expression in HepG2 and HuH7 liver hepatoma cell lines after 24 and 48 hours.

TABLE 16

|  | MxA Fold Induction | Pkr Fold Induction | OAS Fold Induction |
| --- | --- | --- | --- |
| HepG2 24 hr IL28 | 12.4 | 0.7 | 3.3 |
| HepG2 24 hr IL29 | 36.6 | 2.2 | 6.4 |
| HepG2 24 hr IFNα2a | 12.2 | 1.9 | 3.2 |

TABLE 16-continued

|  | MxA Fold Induction | Pkr Fold Induction | OAS Fold Induction |
|---|---|---|---|
| HepG2 24 hr IFNβ | 93.6 | 3.9 | 19.0 |
| HepG2 48 hr IL28 | 2.7 | 0.9 | 1.1 |
| HepG2 48 hr IL29 | 27.2 | 2.1 | 5.3 |
| HepG2 48 hr IFNα2a | 2.5 | 0.9 | 1.2 |
| HepG2 48 hr IFNβ | 15.9 | 1.8 | 3.3 |
| HuH7 24 hr IL28 | 132.5 | 5.4 | 52.6 |
| HuH7 24 hr IL29 | 220.2 | 7.0 | 116.6 |
| HuH7 24 hr IFNα2a | 157.0 | 5.7 | 67.0 |
| HuH7 24 hr IFNβ | 279.8 | 5.6 | 151.8 |
| HuH7 48 hr IL28 | 25.6 | 3.4 | 10.3 |
| HuH7 48 hr IL29 | 143.5 | 7.4 | 60.3 |
| HuH7 48 hr IFNα2a | 91.3 | 5.8 | 32.3 |
| HuH7 48 hr IFNβ | 65.0 | 4.2 | 35.7 |

TABLE 17

|  | MxA Fold Induction | OAS Fold Induction | Pkr Fold Induction |
|---|---|---|---|
| MetIL-29-PEG | 36.7 | 6.9 | 2.2 |
| MetIL-29C172S-PEG | 46.1 | 8.9 | 2.8 |

Data shown is for 20 ng/ml metIL-29-PEG and metIL-29C172S-PEG versions of IL-29 after culture for 24 hours.

Data shown is normalized to HPRT and shown as fold induction over unstimulated cells.

Example 14

Antiviral Activity of IL-28 and IL-29 in HCV Replicon System

The ability of antiviral drugs to inhibit HCV replication can be tested in vitro with the HCV replicon system. The replicon system consists of the Huh7 human hepatoma cell line that has been transfected with subgenomic RNA replicons that direct constitutive replication of HCV genomic RNAs (Blight, K. J. et al. *Science* 290:1972-1974, 2000). Treatment of replicon clones with IFNα at 10 IU/ml reduces the amount of HCV RNA by 85% compared to untreated control cell lines. The ability of IL-28A and IL-29 to reduce the amount of HCV RNA produced by the replicon clones in 72 hours indicates the antiviral state conferred upon Huh7 cells by IL-28A/IL-29 treatment is effective in inhibiting HCV replicon replication, and thereby, very likely effective in inhibiting HCV replication.

The ability of IL-28A and IL-29 to inhibit HCV replication as determined by Bayer Branched chain DNA kit, is be done under the following conditions:

IL28 alone at increasing concentrations (6)* up to 1.0 µg/ml

IL29 alone at increasing concentrations (6)* up to 1.0 µg/ml

PEGIL29 alone at increasing concentrations (6)* up to 1.0 µg/ml

IFNα$_2$A alone at 0.3, 1.0, and 3.0 IU/ml

Ribavirin alone.

The positive control is IFNα and the negative control is ribavirin.

The cells are stained after 72 hours with Alomar Blue to assess viablility.

*The concentrations for conditions 1-3 are:

µg/ml, 0.32 µg/ml, 0.10 µg/ml, 0.032 µg/ml, 0.010 µg/ml, 0.0032 µg/ml.

The replicon clone (BB7) is treated 1× per day for 3 consecutive days with the doses listed above. Total HCV RNA is measured after 72 hours.

Example 15

IL-28 and IL-29 have Antiviral Activity Against Pathogenic Viruses

Two methods are used to assay in vitro antiviral activity of IL-28 and IL-29 against a panel of pathogenic viruses including, among others, adenovirus, parainfluenza virus. respiratory syncytial virus, rhino virus, coxsackie virus, influenza virus, vaccinia virus, west nile virus, dengue virus, venezuelan equine encephalitis virus, pichinde virus and polio virus. These two methods are inhibition of virus-induced cytopathic effect (CPE) determined by visual (microscopic) examination of the cells and increase in neutral red (NR) dye uptake into cells. In the CPE inhibition method, seven concentrations of test drug (log 10 dilutions, such as 1000, 100, 10, 1, 0.1, 0.01, 0.001 ng/ml) are evaluated against each virus in 96-well flat-bottomed microplates containing host cells. The compounds are added 24 hours prior to virus, which is used at a concentration of approximately 5 to 100 cell culture infectious doses per well, depending upon the virus, which equates to a multiplicity of infection (MOI) of 0.01 to 0.0001 infectious particles per cell. The tests are read after incubation at 37° C. for a specified time sufficient to allow adequate viral cytopathic effect to develop. In the NR uptake assay, dye (0.34% concentration in medium) is added to the same set of plates used to obtain the visual scores. After 2 h, the color intensity of the dye absorbed by and subsequently eluted from the cells is determined using a microplate autoreader. Antiviral activity is expressed as the 50% effective (virus-inhibitory) concentration (EC50) determined by plotting compound concentration versus percent inhibition on semilogarithmic graph paper. The EC50/IC50 data in some cases may be determined by appropriate regression analysis software. In general, the EC50s determined by NR assay are two- to fourfold higher than those obtained by the CPE method.

TABLE 18

| Visual Assay | | | | | |
|---|---|---|---|---|---|
| Virus | Cell line | Drug | EC50 Visual | IC50 Visual | SI Visual (IC50/EC50) |
| Adenovirus | A549 | IL-28A | >10 µg/ml | >10 µg/ml | 0 |
| Adenovirus | A549 | IL-29 | >10 µg/ml | >10 µg/ml | 0 |
| Adenovirus | A549 | MetIL-29C172S-PEG | >10 µg/ml | >10 µg/ml | 0 |
| Parainfluenza virus | MA-104 | IL-28A | >10 µg/ml | >10 µg/ml | 0 |
| Parainfluenza virus | MA-104 | IL-29 | >10 µg/ml | >10 µg/ml | 0 |

TABLE 18-continued

| | | | Visual Assay | | |
|---|---|---|---|---|---|
| Virus | Cell line | Drug | EC50 Visual | IC50 Visual | SI Visual (IC50/EC50) |
| Parainfluenza virus | MA-104 | MetIL-29C172S-PEG | >10 µg/ml | >10 µg/ml | 0 |
| Respiratory syncytial virus | MA-104 | IL-28A | >10 µg/ml | >10 µg/ml | 0 |
| Respiratory syncytial virus | MA-104 | IL-29 | >10 µg/ml | >10 µg/ml | 0 |
| Respiratory syncytial virus | MA-104 | MetIL-29C172S-PEG | >10 µg/ml | >10 µg/ml | 0 |
| Rhino 2 | KB | IL-28A | >10 µg/ml | >10 µg/ml | 0 |
| Rhino 2 | KB | IL-29 | >10 µg/ml | >10 µg/ml | 0 |
| Rhino 2 | KB | MetIL-29C172S-PEG | >10 µg/ml | >10 µg/ml | 0 |
| Rhino 9 | HeLa | IL-28A | >10 µg/ml | >10 µg/ml | 0 |
| Rhino 9 | HeLa | IL-29 | >10 µg/ml | >10 µg/ml | 0 |
| Rhino 9 | HeLa | MetIL-29C172S-PEG | >10 µg/ml | >10 µg/ml | 0 |
| Coxsackie B4 virus | KB | IL-28A | >10 µg/ml | >10 µg/ml | 0 |
| Coxsackie B4 virus | KB | IL-29 | >10 µg/ml | >10 µg/ml | 0 |
| Coxsackie B4 virus | KB | MetIL-29C172S-PEG | >10 µg/ml | >10 µg/ml | 0 |
| Influenza (type A [H3N2]) | Maden-Darby Canine Kidney | IL-28A | >10 µg/ml | >10 µg/ml | 0 |
| Influenza (type A [H3N2]) | Maden-Darby Canine Kidney | IL-29 | >10 µg/ml | >10 µg/ml | 0 |
| Influenza (type A [H3N2]) | Maden-Darby Canine Kidney | MetIL-29C172S-PEG | >10 µg/ml | >10 µg/ml | 0 |
| Influenza (type A [H3N2]) | Vero | IL-28A | 0.1 µg/ml | >10 µg/ml | >100 |
| Influenza (type A [H3N2]) | Vero | IL-29 | >10 µg/ml | >10 µg/ml | 0 |
| Influenza (type A [H3N2]) | Vero | MetIL-29C172S-PEG | 0.045 µg/ml | >10 µg/ml | >222 |
| Vaccinia virus | Vero | IL-28A | >10 µg/ml | >10 µg/ml | 0 |
| Vaccinia virus | Vero | IL-29 | >10 µg/ml | >10 µg/ml | 0 |
| Vaccinia virus | Vero | MetIL-29C172S-PEG | >10 µg/ml | >10 µg/ml | 0 |
| West Nile virus | Vero | IL-28A | 0.00001 µg/ml | >10 µg/ml | >1,000,000 |
| West Nile virus | Vero | IL-29 | 0.000032 µg/ml | >10 µg/ml | >300,000 |
| West Nile virus | Vero | MetIL-29C172S-PEG | 0.001 µg/ml | >10 µg/ml | >10,000 |
| Dengue virus | Vero | IL-28A | 0.01 µg/ml | >10 µg/ml | >1000 |
| Dengue virus | Vero | IL-29 | 0.032 µg/ml | >10 µg/ml | >312 |
| Dengue virus | Vero | MetIL-29C172S-PEG | 0.0075 µg/ml | >10 µg/ml | >1330 |
| Venezuelan equine encephalitis virus | Vero | IL-28A | 0.01 µg/ml | >10 µg/ml | >1000 |
| Venezuelan equine encephalitis virus | Vero | IL-29 | 0.012 µg/ml | >10 µg/ml | >833 |

TABLE 18-continued

Visual Assay

| Virus | Cell line | Drug | EC50 Visual | IC50 Visual | SI Visual (IC50/EC50) |
|---|---|---|---|---|---|
| Venezuelan equine encephalitis virus | Vero | MetIL-29C172S-PEG | 0.0065 µg/ml | >10 µg/ml | >1538 |
| Pichinde virus | BSC-1 | IL-28A | >10 µg/ml | >10 µg/ml | 0 |
| Pichinde virus | BSC-1 | IL-29 | >10 µg/ml | >10 µg/ml | 0 |
| Pichinde virus | BSC-1 | MetIL-29C172S-PEG | >10 µg/ml | >10 µg/ml | 0 |
| Polio virus | Vero | IL-28A | >10 µg/ml | >10 µg/ml | 0 |
| Polio virus | Vero | IL-29 | >10 µg/ml | >10 µg/ml | 0 |
| Polio virus | Vero | MetIL-29C172S-PEG | >10 µg/ml | >10 µg/ml | 0 |

TABLE 19

Neutral Red Assay

| Virus | Cell line | Drug | EC50 NR | IC50 NR | SI NR (IC50/EC50) |
|---|---|---|---|---|---|
| Adenovirus | A549 | IL-28A | >10 µg/ml | >10 µg/ml | 0 |
| Adenovirus | A549 | IL-29 | >10 µg/ml | >10 µg/ml | 0 |
| Adenovirus | A549 | MetIL-29C172S-PEG | >10 µg/ml | >10 µg/ml | 0 |
| Parainfluenza virus | MA-104 | IL-28A | >10 µg/ml | >10 µg/ml | 0 |
| Parainfluenza virus | MA-104 | IL-29 | >10 µg/ml | >10 µg/ml | 0 |
| Parainfluenza virus | MA-104 | MetIL-29C172S-PEG | >10 µg/ml | >10 µg/ml | 0 |
| Respiratory syncytial virus | MA-104 | IL-28A | >10 µg/ml | >10 µg/ml | 0 |
| Respiratory syncytial virus | MA-104 | IL-29 | >10 µg/ml | >10 µg/ml | 0 |
| Respiratory syncytial virus | MA-104 | MetIL-29C172S-PEG | 5.47 µg/ml | >10 µg/ml | >2 |
| Rhino 2 | KB | IL-28A | >10 µg/ml | >10 µg/ml | 0 |
| Rhino 2 | KB | IL-29 | >10 µg/ml | >10 µg/ml | 0 |
| Rhino 2 | KB | MetIL-29C172S-PEG | >10 µg/ml | >10 µg/ml | 0 |
| Rhino 9 | HeLa | IL-28A | 1.726 µg/ml | >10 µg/ml | >6 |
| Rhino 9 | HeLa | IL-29 | 0.982 µg/ml | >10 µg/ml | >10 |
| Rhino 9 | HeLa | MetIL-29C172S-PEG | 2.051 µg/ml | >10 µg/ml | >5 |
| Coxsackie B4 virus | KB | IL-28A | >10 µg/ml | >10 µg/ml | 0 |
| Coxsackie B4 virus | KB | IL-29 | >10 µg/ml | >10 µg/ml | 0 |
| Coxsackie B4 virus | KB | MetIL-29C172S-PEG | >10 µg/ml | >10 µg/ml | 0 |
| Influenza (type A [H3N2]) | Maden-Darby Canine Kidney | IL-28A | >10 µg/ml | >10 µg/ml | 0 |
| Influenza (type A [H3N2]) | Maden-Darby Canine Kidney | IL-29 | >10 µg/ml | >10 µg/ml | 0 |
| Influenza (type A [H3N2]) | Maden-Darby Canine Kidney | MetIL-29C172S-PEG | >10 µg/ml | >10 µg/ml | 0 |
| Influenza (type A [H3N2]) | Vero | IL-28A | 0.25 µg/ml | >10 µg/ml | >40 |
| Influenza (type A [H3N2]) | Vero | IL-29 | 2 µg/ml | >10 µg/ml | >5 |

TABLE 19-continued

Neutral Red Assay

| Virus | Cell line | Drug | EC50 NR | IC50 NR | SI NR (IC50/EC50) |
|---|---|---|---|---|---|
| Influenza (type A [H3N2]) | Vero | MetIL-29C172S-PEG | 1.4 μg/ml | >10 μg/ml | >7 |
| Vaccinia virus | Vero | IL-28A | >10 μg/ml | >10 μg/ml | 0 |
| Vaccinia virus | Vero | IL-29 | >10 μg/ml | >10 μg/ml | 0 |
| Vaccinia virus | Vero | MetIL-29C172S-PEG | >10 μg/ml | >10 μg/ml | 0 |
| West Nile virus | Vero | IL-28A | 0.0001 μg/ml | >10 μg/ml | >100,000 |
| West Nile virus | Vero | IL-29 | 0.00025 μg/ml | >10 μg/ml | >40,000 |
| West Nile virus | Vero | MetIL-29C172S-PEG | 0.00037 μg/ml | >10 μg/ml | >27,000 |
| Dengue virus | Vero | IL-28A | 0.1 μg/ml | >10 μg/ml | >100 |
| Dengue virus | Vero | IL-29 | 0.05 μg/ml | >10 μg/ml | >200 |
| Dengue virus | Vero | MetIL-29C172S-PEG | 0.06 μg/ml | >10 μg/ml | >166 |
| Venezuelan equine encephalitis virus | Vero | IL-28A | 0.035 μg/ml | >10 μg/ml | >286 |
| Venezuelan equine encephalitis virus | Vero | IL-29 | 0.05 μg/ml | >10 μg/ml | >200 |
| Venezuelan equine encephalitis virus | Vero | MetIL-29C172S-PEG | 0.02 μg/ml | >10 μg/ml | >500 |
| Pichinde virus | BSC-1 | IL-28A | >10 μg/ml | >10 μg/ml | 0 |
| Pichinde virus | BSC-1 | IL-29 | >10 μg/ml | >10 μg/ml | 0 |
| Pichinde virus | BSC-1 | MetIL-29C172S-PEG | >10 μg/ml | >10 μg/ml | 0 |
| Polio virus | Vero | IL-28A | >1.672 μg/ml | >10 μg/ml | >6 |
| Polio virus | Vero | IL-29 | >10 μg/ml | >10 μg/ml | 0 |
| Polio virus | Vero | MetIL-29C172S-PEG | >10 μg/ml | >10 μg/ml | 0 |

Example 16

IL-28, IL-29, metIL-29-PEG and metIL-29C172S-PEG Stimulate ISG Induction in the Mouse Liver Cell Line AML-12

Interferon stimulated genes (ISGs) are genes that are induced by type I interferons (IFNs) and also by the IL-28 and IL-29 family molecules, suggesting that IFN and IL-28 and IL-29 induce similar pathways leading to antiviral activity. Human type I IFNs (IFNα1-4 and IFNβ) have little or no activity on mouse cells, which is thought to be caused by lack of species cross-reactivity. To test if human IL-28 and IL-29 have effects on mouse cells, ISG induction by human IL-28 and IL-29 was evaluated by real-time PCR on the mouse liver derived cell line AML-12.

AML-12 cells were plated in 6-well plates in complete DMEM media at a concentration of $2 \times 10^6$ cells/well. Twenty-four hours after plating cells, human IL-28 and IL-29 were added to the culture at a concentration of 20 ng/ml. As a control, cells were either stimulated with mouse IFNα (positive control) or unstimulated (negative). Cells were harvested at 8, 24, 48 and 72 hours after addition of CHO-derived human M-28A (SEQ ID NO:18) or M-29 (SEQ ID NO:20). RNA was isolated from cell pellets using RNAEasy-kit® (Qiagen, Valencia, Calif.). RNA was treated with DNase (Millipore, Billerica, Mass.) to clean RNA of any contaminating DNA. cDNA was generated using Perkin-Elmer RT mix. ISG gene induction was evaluated by real-time PCR using primers and probes specific for mouse OAS, Pkr and Mx1. To obtain quantitative data, HPRT real-time PCR was duplexed with ISG PCR. A standard curve was obtained using known amounts of RNA from IFN-stimulated mouse PBLs. All data are shown as expression relative to internal HPRT expression.

Human IL-28A and IL-29 stimulated ISG induction in the mouse hepatocyte cell line AML-12 and demonstrated that unlike type I IFNs, the IL-28/29 family proteins showed cross-species reactivity.

TABLE 20

| Stimulation | OAS | PkR | Mx1 |
|---|---|---|---|
| None | 0.001 | 0.001 | 0.001 |
| Human IL-28 | 0.04 | 0.02 | 0.06 |
| Human IL-29 | 0.04 | 0.02 | 0.07 |
| Mouse IL-28 | 0.04 | 0.02 | 0.08 |
| Mouse IFNα | 0.02 | 0.02 | 0.01 |

All data shown were expressed as fold relative to HPRT gene expression ng of OAS mRNA=normalized value of OAS mRNA amount relative to internal ng of HPRT mRNA housekeeping gene, HPRT As an example, the data for the 48 hour time point is shown.

TABLE 21

| | AML12's | | |
|---|---|---|---|
| | Mx1 Fold Induction | OAS Fold Induction | Pkr Fold Induction |
| MetIL-29-PEG | 728 | 614 | 8 |
| MetIL-29C172S-PEG | 761 | 657 | 8 |

Cells were stimulated with 20 ng/ml metIL-29-PEG or metIL-29C172S-PEG for 24 hours.

Data shown is normalized to HPRT and shown as fold induction over unstimulated cells.

Example 17

ISGs are Efficiently Induced in Spleens of Transgenic Mice Expressing Human IL-29

Transgenic (Tg) mice were generated expressing human IL-29 under the control of the Eu-lck promoter. To study if human IL-29 has biological activity in vivo in mice, expression of ISGs was analyzed by real-time PCR in the spleens of Eu-lck IL-29 transgenic mice.

Transgenic mice (C3H/C57BL/6) were generated using a construct that expressed the human IL-29 gene under the control of the Eu-lck promoter. This promoter is active in T cells and B cells. Transgenic mice and their non-transgenic littermates (n=2/gp) were sacrificed at about 10 weeks of age. Spleens of mice were isolated. RNA was isolated from cell pellets using RNAEasy-kit® (Qiagen). RNA was treated with DNase to clean RNA of any contaminating DNA. cDNA was generated using Perkin-Elmer RT® mix. ISO gene induction was evaluated by real-time PCR using primers and probes (5' FAM, 3' NFQ) specific for mouse OAS, Pkr and Mx1. To obtain quantitative data, HPRT real-time PCR was duplexed with ISG PCR. Furthermore, a standard curve was obtained using known amounts of IFN stimulated mouse PBLs. All data are shown as expression relative to internal HPRT expression.

Spleens isolated from IL-29 Tg mice showed high induction of ISGs OAS, Pkr and Mx1 compared to their non-Tg littermate controls suggesting that human IL-29 is biologically active in vivo in mice.

TABLE 22

| Mice | OAS | PkR | Mx1 |
|---|---|---|---|
| Non-Tg | 4.5 | 4.5 | 3.5 |
| IL-29 Tg | 12 | 8 | 21 |

All data shown are fold expression relative to HPRT gene expression. The average expression in two mice is shown Example 18

Human IL-28 and IL-29 Protein Induce ISG Gene Expression in Liver, Spleen and Blood of Mice To determine whether human IL-28 and IL-29 induce interferon stimulated genes in vivo, CHO-derived human IL-28A and IL-29 protein were injected into mice. In addition, *E. coli* derived IL-29 was also tested in in vivo assays as described above using MetIL-29C172S-PEG and MetIL-29-PEG. At various time points and at different doses, ISG gene induction was measured in the blood, spleen and livers of the mice.

C57BL/6 mice were injected i.p or i.v with a range of doses (10 μg-250 μg) of CHO-derived human IL-28A and IL-29 or MetIL-29C172S-PEG and MetIL-29C16-C113-PEG. Mice were sacrificed at various time points (1 hr-48 hr). Spleens and livers were isolated from mice, and RNA was isolated. RNA was also isolated from the blood cells. The cells were pelleted and RNA isolated from pellets using RNAEasy®-kit (Qiagen). RNA was treated with DNase (Amicon) to rid RNA of any contaminating DNA. cDNA was generated using Perkin-Elmer RT mix (Perkin-Elmer). ISG gene induction was measured by real-time PCR using primers and probes specific for mouse OAS, Pkr and Mx1. To obtain quantitative data, HPRT real-time PCR was duplexed with ISG PCR. A standard curve was calculated using known amounts of IFN-stimulated mouse PBLs. All data are shown as expression relative to internal HPRT expression.

Human IL-29 induced ISG gene expression (OAS, Pkr, Mx1) in the livers, spleen and blood of mice in a dose dependent manner. Expression of ISGs peaked between 1-6 hours after injection and showed sustained expression above control mice upto 48 hours. In this experiment, human IL-28A did not induce ISG gene expression.

TABLE 23

| Injection | OAS-1 hr | OAS-6 hr | OAS-24 hr | OAS-48 hr |
|---|---|---|---|---|
| None - liver | 1.6 | 1.6 | 1.6 | 1.6 |
| IL-29 liver | 2.5 | 4 | 2.5 | 2.8 |
| None - spleen | 1.8 | 1.8 | 1.8 | 1.8 |
| IL-29 - spleen | 4 | 6 | 3.2 | 3.2 |
| None - blood | 5 | 5 | 5 | 5 |
| IL-29 blood | 12 | 18 | 11 | 10 |

Results shown are fold expression relative to HPRT gene expression. A sample data set for IL-29 induced OAS in liver at a single injection of 250 ng i.v. is shown. The data shown is the average expression from 5 different animals/group.

TABLE 24

| Injection | OAS (24 hr) |
|---|---|
| None | 1.8 |
| IL-29 10 μg | 3.7 |
| IL-29 50 μg | 4.2 |
| IL-29 250 μg | 6 |

TABLE 25

| | MetIL-29-PEG | | | | MetIL-29C172S-PEG | | | | Naive |
|---|---|---|---|---|---|---|---|---|---|
| | 3 hr | 6 hr | 12 hr | 24 hr | 3 hr | 6 hr | 12 hr | 24 hr | 24 hr |
| PKR | 18.24 | 13.93 | 4.99 | 3.77 | 5.29 | 5.65 | 3.79 | 3.55 | 3.70 |
| OAS | 91.29 | 65.93 | 54.04 | 20.81 | 13.42 | 13.02 | 10.54 | 8.72 | 6.60 |
| Mx1 | 537.51 | 124.99 | 33.58 | 35.82 | 27.89 | 29.34 | 16.61 | 0.00 | 10.98 |

Mice were injected with 100 µg of proteins i.v. Data shown is fold expression over HPRT expression from livers of mice. Similar data was obtained from blood and spleens of mice.

Example 19

IL-28 and IL-29 Induce ISG Protein in Mice

To analyze of the effect of human IL-28 and IL-29 on induction of ISG protein (OAS), serum and plasma from IL-28 and IL-29 treated mice were tested for OAS activity.

C57BL/6 mice were injected i.v with PBS or a range of concentrations (10 µg-250 ng) of human IL-28 or IL-29. Serum and plasma were isolated from mice at varying time points, and OAS activity was measured using the OAS radio-immunoassay (RIA) kit from Eiken Chemicals (Tokyo, Japan).

IL-28 and IL-29 induced OAS activity in the serum and plasma of mice showing that these proteins are biologically active in vivo.

TABLE 26

| Injection | OAS-1 hr | OAS-6 hr | OAS-24 hr | OAS-48 hr |
|---|---|---|---|---|
| None | 80 | 80 | 80 | 80 |
| IL-29 | 80 | 80 | 180 | 200 |

OAS activity is shown at pmol/dL of plasma for a single concentration (250 µg) of human IL-29.

Example 20

IL-28 and IL-29 Inhibit Adenoviral Pathology in Mice

To test the antiviral activities of IL-28 and IL-29 against viruses that infect the liver, the test samples were tested in mice against infectious adenoviral vectors expressing an internal green fluorescent protein (GFP) gene. When injected intravenously, these viruses primarily target the liver for gene expression. The adenoviruses are replication deficient, but cause liver damage due to inflammatory cell infiltrate that can be monitored by measurement of serum levels of liver enzymes like AST and ALT, or by direct examination of liver pathology.

C57B1/6 mice were given once daily intraperitoneal injections of 50 µg mouse IL-28 (zcyto24 as shown in SEQ ID NO:9) or metIL-29C172S-PEG for 3 days. Control animals were injected with PBS. One hour following the 3$^{rd}$ dose, mice were given a single bolus intravenous tail vein injection of the adenoviral vector, AdGFP (1×10$^9$ plaque-forming units (pfu)). Following this, every other day mice were given an additional dose of PBS, mouse IL-28 or metIL-29C172S-PEG for 4 more doses (total of 7 doses). One hour following the final dose of PBS, mouse IL-28 or metIL-29C172S-PEG mice were terminally bleed and sacrificed. The serum and liver tissue were analyzed. Serum was analyzed for AST and ALT liver enzymes. Liver was isolated and analyzed for GFP expression and histology. For histology, liver specimens were fixed in formalin and then embedded in paraffin followed by H&E staining. Sections of liver that had been blinded to treat were examined with a light microscope. Changes were noted and scored on a scale designed to measure liver pathology and inflammation.

Mouse IL-28 and IL-29 inhibited adenoviral infection and gene expression as measured by liver fluorescence. PBS-treated mice (n=8) had an average relative liver fluorescence of 52.4 (arbitrary units). In contrast, IL-28-treated mice (n=8) had a relative liver fluorescence of 34.5, and IL-29-treated mice (n=8) had a relative liver fluorescence of 38.9. A reduction in adenoviral infection and gene expression led to a reduced liver pathology as measured by serum ALT and AST levels and histology. PBS-treated mice (n=8) had an average serum AST of 234 U/L (units/liter) and serum ALT of 250 U/L. In contrast, IL-28-treated mice (n=8) had an average serum AST of 193 U/L and serum ALT of 216 U/L, and IL-29-treated mice (n=8) had an average serum AST of 162 U/L and serum ALT of 184 U/L. In addition, the liver histology indicated that mice given either mouse IL-28 or IL-29 had lower liver and inflammation scores than the PBS-treated group. The livers from the IL-29 group also had less proliferation of sinusoidal cells, fewer mitotic figures and fewer changes in the hepatocytes (e.g. vacuolation, presence of multiple nuclei, hepatocyte enlargement) than in the PBS treatment group. These data demonstrate that mouse IL-28 and IL-29 have antiviral properties against a liver-trophic virus.

Example 21

LCMV Models

Lymphocytic choriomeningitis virus (LCMV) infections in mice are an excellent model of acture and chronic infection. These models are used to evaluate the effect of cytokines on the antiviral immune response and the effects IL-28 and IL-29 have viral load and the antiviral immune response. The two models used are: LCMV Armstrong (acute) infection and LCMV Clone 13 (chronic) infection. (See, e.g., Wherry et al., *J. Virol.* 77:4911-4927, 2003; Blattman et al., *Nature Med.* 9(5):540-547, 2003; Hoffman et al., *J. Immunol.* 170:1339-1353, 2003.) There are three stages of CD8 T cell development in response to virus: 1) expansion, 2) contraction, and 3) memory (acute model). IL-28 or IL-29 is injected during each stage for both acute and chronic models. In the chronic model, IL-28 or IL-29 is injected 60 days after infection to assess the effect of IL-28 or IL-29 on persistent viral load. For both acute and chronic models, IL-28 or IL-29 is injected, and the viral load in blood, spleen and liver is examined. Other parameter that can be examined include: tetramer staining by flow to count the number of LCMV-specific CD8+ T cells; the ability of tetramer+ cells to produce cytokines when stimulated with their cognate LCMV antigen; and the ability of LCMV-specific CD8+ T cells to proliferate in response to their cognate LCMV antigen. LCMV-specific T cells are phenotyped by flow cytometry to assess the cells activation and differentiation state. Also, the ability of LCMV-specific CTL to lyse target cells bearing their cognate LCMV antigen is examined. The number and function of LCMV-specific CD4+ T cells is also assessed.

A reduction in viral load after treatment with IL-28 or IL-29 is determined. A 50% reduction in viral load in any organ, especially liver, would be significant. For IL-28 or IL-29 treated mice, a 20% increase in the percentage of tetramer positive T cells that proliferate, make cytokine, or display a mature phenotype relative to untreated mice would also be considered significant.

IL-28 or IL-29 injection leading to a reduction in viral load is due to more effective control of viral infection especially in the chronic model where untreated the viral titers remain elevated for an extended period of time. A two fold reduction in viral titer relative to untreated mice is considered significant.

Example 22

Influenza Model of Acute Viral Infection
A. Preliminary Experiment to test antiviral activity.

To determine the antiviral activity of IL-28 or IL-29 on acute infection by Influenza virus, an in vivo study using influenza infected c57B1/6 mice is performed using the following protocol:

Animals: 6 weeks-old female BALB/c mice (Charles River) with 148 mice, 30 per group.

Groups:

Absolute control (not infected) to run in parallel for antibody titre and histopathology (2 animals per group)

Vehicle (i.p.) saline

Amantadine (positive control) 10 mg/day during 5 days (per os) starting 2 hours before infection IL-28 or IL-29 treated (5 µg, i.p. starting 2 hours after infection)

IL-28 or IL-29 (25 µg, i.p. starting 2 hours after infection)

IL-28 or IL-29 (125 µg, i.p. starting 2 hours after infection)

Day 0—Except for the absolute controls, all animals infected with Influenza virus For viral load (10 at LD50)

For immunology workout (LD30)

Day 0-9—daily injections of IL-28 or IL-29 (i.p.)

Body weight and general appearance recorded (3 times/week)

Day 3—sacrifice of 8 animals per group

Viral load in right lung (TCID50)

Histopathology in left lung

Blood sample for antibody titration

Day 10—sacrifice of all surviving animals collecting blood samples for antibody titration, isolating lung lymphocytes (4 pools of 3) for direct CTL assay (in all 5 groups), and quantitative immunophenotyping for the following markers: CD3/CD4, CD3/CD8, CD3/CD8/CD11b, CD8/CD44/CD62L, CD3/DX5, GR-1/F480, and CD19.

Study No. 2

Efficacy study of IL-28 or IL-29 in C57B1/6 mice infected with mouse-adapted virus is done using 8 weeks-old female C57B1/6 mice (Charles River).

Group 1: Vehicle (i.p.)

Group 2: Positive control: Anti-influenza neutralizing antibody (goat anti-influenza A/USSR(H1N1) (Chemicon International, Temecula, Calif.); 40 µg/mouse at 2 h and 4 h post infection (10 µl intranasal)

Group 3: IL-28 or IL-29 (5 µg, i.p.)

Group 4: IL-28 or IL-29 (25 µg, i.p.)

Group 5: IL-28 or IL-29 (125 µg, i.p.)

Following-life observations and immunological workouts are prepared:

Day 0—all animals infected with Influenza virus (dose determined in experiment 2)

Day 0-9—daily injections of IL-28 or IL-29 (i.p.)

Body weight and general appearance recorded every other day

Day 10—sacrifice of surviving animals and perform viral assay to determine viral load in lung.

Isolation of lung lymphocytes (for direct CTL assay in the lungs using EL-4 as targets and different E:T ratio (based on best results from experiments 1 and 2).

Tetramer staining: The number of CD8+ T cells binding MHC Class I tetramers containing influenza A nucleoprotein (NP) epitope are assessed using complexes of MHC class I with viral peptides: FLU-NP$_{366-374}$/D$^b$ (ASNENME™), (LMCV peptide/D$^b$).

Quantitative immunophenotyping of the following: CD8, tetramer, intracellular IFNγ, NK1.1, CD8, tetramer, CD62L, CD44, CD3(+ or −), NK1.1(+), intracellular IFNγ, CD4, CD8, NK1.1, DX5, CD3 (+ or −), NK1.1, DX5, tetramer, Single colour samples for cytometer adjustment.

Survival/Re-Challenge Study

Day 30: Survival study with mice are treated for 9 days with different doses of IL-28 or IL-29 or with positive anti-influenza antibody control. Body weight and antibody production in individual serum samples (Total, IgG1, IgG2a, IgG2b) are measured.

Re-Challenge Study:

Day 0: Both groups will be infected with A/PR virus (1LD30).

Group 6 will not be treated.

Group 7 will be treated for 9 days with 125 µg of IL-28 or IL-29.

Day 30: Survival study

Body weight and antibody production in individual serum samples (Total, IgG1, IgG2a, IgG2b) are measured.

Day 60: Re-challenge study

Survivors in each group will be divided into 2 subgroups

Group 6A and 7A will be re-challenge with A/PR virus (1 LD30)

Group 6B and 7B will be re-challenge with A/PR virus (1 LD30).

Both groups will be followed up and day of sacrifice will be determined. Body weight and antibody production in individual serum samples (Total, IgG1, IgG2a, IgG2b) are measured.

Example 21

IL-28 and IL-29 have Antiviral Activity Against Hepatitis B virus (HBV) In Vivo

A transgenic mouse model (Guidotti et al., *J. Virology* 69:6158-6169, 1995) supports the replication of high levels of infectious HBV and has been used as a chemotherapeutic model for HBV infection. Transgenic mice are treated with antiviral drugs and the levels of HBV DNA and RNA are measured in the transgenic mouse liver and serum following treatment. HBV protein levels can also be measured in the transgenic mouse serum following treatment. This model has been used to evaluate the effectiveness of lamivudine and IFN-α in reducing HBV viral titers.

HBV TG mice (male) are given intraperitoneal injections of 2.5, 25 or 250 micrograms IL-28 or IL-29 every other day for 14 days (total of 8 doses). Mice are bled for serum collection on day of treatment (day 0) and day 7. One hour following the final dose of IL-29 mice undergo a terminal bleed and are sacrificed. Serum and liver are analyzed for liver HBV DNA, liver HBV RNA, serum HBV DNA, liver HBc, serum Hbe and serum HBs.

Reduction in liver HBV DNA, liver HBV RNA, serum HBV DNA, liver HBc, serum Hbe or serum HBs in response to IL-28 or IL-29 reflects antiviral activity of these compounds against HBV.

Example 22

IL-28 and IL-29 Inhibit Human Herpesvirus-8 (HHV-8) Replication in BCBL-1 Cells

The antiviral activities of IL-28 and IL-29 were tested against HHV-8 in an in vitro infection system using a B-lymphoid cell line, BCBL-1.

In the HHV-8 assay the test compound and a ganciclovir control were assayed at five concentrations each, diluted in a half-log series. The endpoints were TaqMan PCR for extracellular HHV-8 DNA (IC50) and cell numbers using CellTiter96® reagent (TC50; Promega, Madison, Wis.). Briefly, BCBL-1 cells were plated in 96-well microtiter plates. After 16-24 hours the cells were washed and the medium was replaced with complete medium containing various concentrations of the test compound in triplicate. Ganciclovir was the positive control, while media alone was a negative control (virus control, VC). Three days later the culture medium was replaced with fresh medium containing the appropriately diluted test compound. Six days following the initial administration of the test compound, the cell culture supernatant was collected, treated with pronase and DNAse and then used in a real-time quantitative TaqMan PCR assay. The PCR-amplified HHV-8 DNA was detected in real-time by monitoring increases in fluorescence signals that result from the exonucleolytic degradation of a quenched fluorescent probe molecule that hybridizes to the amplified HHV-8 DNA. For each PCR amplification, a standard curve was simultaneously generated using dilutions of purified HHV-8 DNA. Antiviral activity was calculated from the reduction in HHV-8 DNA levels ($IC_{50}$). A novel dye uptake assay was then employed to measure cell viability which was used to calculate toxicity ($TC_{50}$). The therapeutic index (TI) is calculated as $TC_{50}/IC_{50}$.

IL-28 and IL-29 inhibit HHV-8 viral replication in BCBL-1 cells. IL-28A had an $IC_{50}$ of 1 μg/ml and a $TC_{50}$ of >10 μg/ml (TI>10). IL-29 had an $IC_{50}$ of 6.5 μg/ml and a $TC_{50}$ of >10 μg/ml (TI>1.85). MetIL-29C172S-PEG had an $IC_{50}$ of 0.14 μg/ml and a $TC_{50}$ of >10 μg/ml (TI>100).

Example 23

IL-28 and IL-29 Antiviral Activity Against Epstein Barr Virus (EBV)

The antiviral activities of IL-28 and IL-29 are tested against EBV in an in vitro infection system in a B-lymphoid cell line, P3HR-1. In the EBV assay the test compound and a control are assayed at five concentrations each, diluted in a half-log series. The endpoints are TaqMan PCR for extracellular EBV DNA (IC50) and cell numbers using CellTiter96® reagent (TC50; Promega). Briefly, P3HR-1 cells are plated in 96-well microtiter plates. After 16-24 hours the cells are washed and the medium is replaced with complete medium containing various concentrations of the test compound in triplicate. In addition to a positive control, media alone is added to cells as a negative control (virus control, VC). Three days later the culture medium is replaced with fresh medium containing the appropriately diluted test compound. Six days following the initial administration of the test compound, the cell culture supernatant is collected, treated with pronase and DNAse and then used in a real-time quantitative TaqMan PCR assay. The PCR-amplified EBV DNA is detected in real-time by monitoring increases in fluorescence signals that result from the exonucleolytic degradation of a quenched fluorescent probe molecule that hybridizes to the amplified EBV DNA. For each PCR amplification, a standard curve was simultaneously generated using dilutions of purified EBV DNA. Antiviral activity is calculated from the reduction in EBV DNA levels ($IC_{50}$). A novel dye uptake assay was then employed to measure cell viability which was used to calculate toxicity ($TC_{50}$). The therapeutic index (TI) is calculated as $TC_{50}/IC_{50}$.

Example 24

IL-28 and IL-29 Antiviral Activity Against Herpes Simplex Virus-2 (HSV-2)

The antiviral activities of IL-28 and IL-29 were tested against HSV-2 in an in vitro infection system in Vero cells. The antiviral effects of IL-28 and IL-29 were assessed in inhibition of cytopathic effect assays (CPE). The assay involves the killing of Vero cells by the cytopathic HSV-2 virus and the inhibition of cell killing by IL-28 and IL-29. The Vero cells are propagated in Dulbecco's modified essential medium (DMEM) containing phenol red with 10% horse serum, 1% glutamine and 1% penicillin-streptomycin, while the CPE inhibition assays are performed in DMEM without phenol red with 2% FBS, 1% glutamine and 1% Pen-Strep. On the day preceding the assays, cells were trypsinized (1% trypsin-EDTA), washed, counted and plated out at $10^4$ cells/well in a 96-well flat-bottom BioCoat® plates (Fisher Scientific, Pittsburgh, Pa.) in a volume of 100 μl/well. The next morning, the medium was removed and a pre-titered aliquot of virus was added to the cells. The amount of virus used is the maximum dilution that would yield complete cell killing (>80%) at the time of maximal CPE development. Cell viability is determined using a CellTiter 96® reagent (Promega) according to the manufacturer's protocol, using a Vmax plate reader (Molecular Devices, Sunnyvale, Calif.). Compounds are tested at six concentrations each, diluted in assay medium in a half-log series. Acyclovir was used as a positive control. Compounds are added at the time of viral infection. The average background and drug color-corrected data for percent CPE reduction and percent cell viability at each concentration are determined relative to controls and the $IC_{50}$ calculated relative to the $TC_{50}$.

IL-28A, IL-29 and MetIL-29C172S-PEG did not inhibit cell death ($IC_{50}$ of >10 ug/ml) in this assay. There was also no antiviral activity of IFNα in the is assay.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of treating a Dengue virus infection in a mammal comprising administering to the mammal a therapeutically effective amount of a polypeptide comprising an amino acid sequence having at least 95% sequence identity to-amino acid residues 20-200 of SEQ ID NO:34, and wherein after administration of the polypeptide the Dengue virus infection is reduced.

2. The method of claim 1 wherein the polypeptide is conjugated to a polyalkyl oxide moiety.

3. The method of claim 2 wherein the polyalkyl oxide moiety is a polyethylene glycol.

4. The method of claim 1, wherein the polypeptide comprises amino acid 20-200 of SEQ ID NO:34.

* * * * *

SEQUENCE LISTING

```
<160> NUMBER OF SEQ ID NOS: 40

<210> SEQ ID NO 1
<211> LENGTH: 618
<212> TYPE: DNA
<213> ORGANISM: Homo sapiens
<220> FEATURE:
<221> NAME/KEY: CDS
<222> LOCATION: (1)...(618)
<220> FEATURE:
<221> NAME/KEY: misc_feature
<222> LOCATION: (0)...(0)
<223> OTHER INFORMATION: IL-28A
```

<400> SEQUENCE: 1

```
atg act ggg gac tgc acg cca gtg ctg gtg ctg atg gcc gca gtg ctg      48
Met Thr Gly Asp Cys Thr Pro Val Leu Val Leu Met Ala Ala Val Leu
 1               5                  10                  15 acc gtg act gga gca gtt cct gtc gcc agg ctc cac ggg gct ctc ccg      96
Thr Val Thr Gly Ala Val Pro Val Ala Arg Leu His Gly Ala Leu Pro
             20                  25                  30 gat gca agg ggc tgc cac ata gcc cag ttc aag tcc ctg tct cca cag    144
Asp Ala Arg Gly Cys His Ile Ala Gln Phe Lys Ser Leu Ser Pro Gln
         35                  40                  45 gag ctg cag gcc ttt aag agg gcc aaa gat gcc tta gaa gag tcg ctt    192
Glu Leu Gln Ala Phe Lys Arg Ala Lys Asp Ala Leu Glu Glu Ser Leu
     50                  55                  60 ctg ctg aag gac tgc agg tgc cac tcc cgc ctc ttc ccc agg acc tgg    240
Leu Leu Lys Asp Cys Arg Cys His Ser Arg Leu Phe Pro Arg Thr Trp
 65                  70                  75                  80 gac ctg agg cag ctg cag gtg agg gag cgc ccc atg gct ttg gag gct    288
Asp Leu Arg Gln Leu Gln Val Arg Glu Arg Pro Met Ala Leu Glu Ala
                 85                  90                  95 gag ctg gcc ctg acg ctg aag gtt ctg gag gcc acc gct gac act gac    336
Glu Leu Ala Leu Thr Leu Lys Val Leu Glu Ala Thr Ala Asp Thr Asp
            100                 105                 110 cca gcc ctg gtg gac gtc ttg gac cag ccc ctt cac acc ctg cac cat    384
Pro Ala Leu Val Asp Val Leu Asp Gln Pro Leu His Thr Leu His His
        115                 120                 125 atc ctc tcc cag ttc cgg gcc tgt gtg agt cgt cag ggc ctg ggc acc    432
Ile Leu Ser Gln Phe Arg Ala Cys Val Ser Arg Gln Gly Leu Gly Thr
    130                 135                 140 cag atc cag cct cag ccc acg gca ggg ccc agg acc cgg ggc cgc ctc    480
Gln Ile Gln Pro Gln Pro Thr Ala Gly Pro Arg Thr Arg Gly Arg Leu
145                 150                 155                 160 cac cat tgg ctg tac cgg ctc cag gag gcc cca aaa aag gag tcc cct    528
His His Trp Leu Tyr Arg Leu Gln Glu Ala Pro Lys Lys Glu Ser Pro
                165                 170                 175 ggc tgc ctc gag gcc tct gtc acc ttc aac ctc ttc cgc ctc ctc acg    576
Gly Cys Leu Glu Ala Ser Val Thr Phe Asn Leu Phe Arg Leu Leu Thr
            180                 185                 190 cga gac ctg aat tgt gtt gcc agt ggg gac ctg tgt gtc tga            618
Arg Asp Leu Asn Cys Val Ala Ser Gly Asp Leu Cys Val  *
        195                 200                 205
```

<210> SEQ ID NO 2
<211> LENGTH: 205
<212> TYPE: PRT
<213> ORGANISM: Homo sapiens

<400> SEQUENCE: 2

```
Met Thr Gly Asp Cys Thr Pro Val Leu Val Leu Met Ala Ala Val Leu
 1               5                  10                  15

Thr Val Thr Gly Ala Val Pro Val Ala Arg Leu His Gly Ala Leu Pro
             20                  25                  30

Asp Ala Arg Gly Cys His Ile Ala Gln Phe Lys Ser Leu Ser Pro Gln
         35                  40                  45

Glu Leu Gln Ala Phe Lys Arg Ala Lys Asp Ala Leu Glu Glu Ser Leu
     50                  55                  60

Leu Leu Lys Asp Cys Arg Cys His Ser Arg Leu Phe Pro Arg Thr Trp
 65                  70                  75                  80

Asp Leu Arg Gln Leu Gln Val Arg Glu Arg Pro Met Ala Leu Glu Ala
                 85                  90                  95
```

```
Glu Leu Ala Leu Thr Leu Lys Val Leu Glu Ala Thr Ala Asp Thr Asp
            100                 105                 110

Pro Ala Leu Val Asp Val Leu Asp Gln Pro Leu His Thr Leu His His
            115                 120                 125

Ile Leu Ser Gln Phe Arg Ala Cys Val Ser Arg Gln Gly Leu Gly Thr
            130                 135                 140

Gln Ile Gln Pro Gln Pro Thr Ala Gly Pro Arg Thr Arg Gly Arg Leu
145                 150                 155                 160

His His Trp Leu Tyr Arg Leu Gln Glu Ala Pro Lys Lys Glu Ser Pro
                165                 170                 175

Gly Cys Leu Glu Ala Ser Val Thr Phe Asn Leu Phe Arg Leu Leu Thr
            180                 185                 190

Arg Asp Leu Asn Cys Val Ala Ser Gly Asp Leu Cys Val
            195                 200                 205

<210> SEQ ID NO 3
<211> LENGTH: 603
<212> TYPE: DNA
<213> ORGANISM: Homo sapiens
<220> FEATURE:
<221> NAME/KEY: CDS
<222> LOCATION: (1)...(603)
<220> FEATURE:
<221> NAME/KEY: misc_feature
<222> LOCATION: (0)...(0)
<223> OTHER INFORMATION: IL-29

<400> SEQUENCE: 3 atg gct gca gct tgg acc gtg gtg ctg gtg act ttg gtg cta ggc ttg    48
Met Ala Ala Ala Trp Thr Val Val Leu Val Thr Leu Val Leu Gly Leu
1               5                   10                  15 gcc gtg gca ggc cct gtc ccc act tcc aag ccc acc aca act ggg aag    96
Ala Val Ala Gly Pro Val Pro Thr Ser Lys Pro Thr Thr Thr Gly Lys
            20                  25                  30 ggc tgc cac att ggc agg ttc aaa tct ctg tca cca cag gag cta gcg   144
Gly Cys His Ile Gly Arg Phe Lys Ser Leu Ser Pro Gln Glu Leu Ala
        35                  40                  45 agc ttc aag aag gcc agg gac gcc ttg gaa gag tca ctc aag ctg aaa   192
Ser Phe Lys Lys Ala Arg Asp Ala Leu Glu Glu Ser Leu Lys Leu Lys
    50                  55                  60 aac tgg agt tgc agc tct cct gtc ttc ccc ggg aat tgg gac ctg agg   240
Asn Trp Ser Cys Ser Ser Pro Val Phe Pro Gly Asn Trp Asp Leu Arg
65                  70                  75                  80 ctt ctc cag gtg agg gag cgc cct gtg gcc ttg gag gct gag ctg gcc   288
Leu Leu Gln Val Arg Glu Arg Pro Val Ala Leu Glu Ala Glu Leu Ala
                85                  90                  95 ctg acg ctg aag gtc ctg gag gcc gct gct ggc cca gcc ctg gag gac   336
Leu Thr Leu Lys Val Leu Glu Ala Ala Ala Gly Pro Ala Leu Glu Asp
            100                 105                 110 gtc cta gac cag ccc ctt cac acc ctg cac cac atc ctc tcc cag ctc   384
Val Leu Asp Gln Pro Leu His Thr Leu His His Ile Leu Ser Gln Leu
            115                 120                 125 cag gcc tgt atc cag cct cag ccc aca gca ggg ccc agg ccc cgg ggc   432
Gln Ala Cys Ile Gln Pro Gln Pro Thr Ala Gly Pro Arg Pro Arg Gly
        130                 135                 140 cgc ctc cac cac tgg ctg cac cgg ctc cag gag gcc ccc aaa aag gag   480
Arg Leu His His Trp Leu His Arg Leu Gln Glu Ala Pro Lys Lys Glu
145                 150                 155                 160 tcc gct ggc tgc ctg gag gca tct gtc acc ttc aac ctc ttc cgc ctc   528
Ser Ala Gly Cys Leu Glu Ala Ser Val Thr Phe Asn Leu Phe Arg Leu
                165                 170                 175
```

```
ctc acg cga gac ctc aaa tat gtg gcc gat ggg gac ctg tgt ctg aga       576
Leu Thr Arg Asp Leu Lys Tyr Val Ala Asp Gly Asp Leu Cys Leu Arg
        180                 185                 190 acg tca acc cac cct gag tcc acc tga                                   603
Thr Ser Thr His Pro Glu Ser Thr *
        195                 200

<210> SEQ ID NO 4
<211> LENGTH: 200
<212> TYPE: PRT
<213> ORGANISM: Homo sapiens

<400> SEQUENCE: 4

Met Ala Ala Ala Trp Thr Val Val Leu Val Thr Leu Val Leu Gly Leu
 1               5                  10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asp Leu Cys Leu Arg
            180                 185                 190

Thr Ser Thr His Pro Glu Ser Thr
        195                 200

<210> SEQ ID NO 5
<211> LENGTH: 615
<212> TYPE: DNA
<213> ORGANISM: Homo sapiens
<220> FEATURE:
<221> NAME/KEY: CDS
<222> LOCATION: (1)...(615)
<220> FEATURE:
<221> NAME/KEY: misc_feature
<222> LOCATION: (0)...(0)
<223> OTHER INFORMATION: IL-28B

<400> SEQUENCE: 5 atg acc ggg gac tgc atg cca gtg ctg gtg ctg atg gcc gca gtg ctg        48
Met Thr Gly Asp Cys Met Pro Val Leu Val Leu Met Ala Ala Val Leu
 1               5                  10                  15 acc gtg act gga gca gtt cct gtc gcc agg ctc cgc ggg gct ctc ccg        96
Thr Val Thr Gly Ala Val Pro Val Ala Arg Leu Arg Gly Ala Leu Pro
            20                  25                  30 gat gca agg ggc tgc cac ata gcc cag ttc aag tcc ctg tct cca cag       144
Asp Ala Arg Gly Cys His Ile Ala Gln Phe Lys Ser Leu Ser Pro Gln
```

-continued

```
                    35                  40                  45
gag ctg cag gcc ttt aag agg gcc aaa gat gcc tta gaa gag tcg ctt      192
Glu Leu Gln Ala Phe Lys Arg Ala Lys Asp Ala Leu Glu Glu Ser Leu
         50                  55                  60 ctg ctg aag gac tgc aag tgc cgc tcc cgc ctc ttc ccc agg acc tgg      240
Leu Leu Lys Asp Cys Lys Cys Arg Ser Arg Leu Phe Pro Arg Thr Trp
 65                  70                  75                  80 gac ctg agg cag ctg cag gtg agg gag cgc ccc gtg gct ttg gag gct      288
Asp Leu Arg Gln Leu Gln Val Arg Glu Arg Pro Val Ala Leu Glu Ala
                 85                  90                  95 gag ctg gcc ctg acg ctg aag gtt ctg gag gcc acc gct gac act gac      336
Glu Leu Ala Leu Thr Leu Lys Val Leu Glu Ala Thr Ala Asp Thr Asp
            100                 105                 110 cca gcc ctg ggg gat gtc ttg gac cag ccc ctt cac acc ctg cac cat      384
Pro Ala Leu Gly Asp Val Leu Asp Gln Pro Leu His Thr Leu His His
        115                 120                 125 atc ctc tcc cag ctc cgg gcc tgt gtg agt cgt cag ggc ccg ggc acc      432
Ile Leu Ser Gln Leu Arg Ala Cys Val Ser Arg Gln Gly Pro Gly Thr
    130                 135                 140 cag atc cag cct cag ccc acg gca ggg ccc agg acc cgg ggc cgc ctc      480
Gln Ile Gln Pro Gln Pro Thr Ala Gly Pro Arg Thr Arg Gly Arg Leu
145                 150                 155                 160 cac cat tgg ctg cac cgg ctc cag gag gcc cca aaa aag gag tcc cct      528
His His Trp Leu His Arg Leu Gln Glu Ala Pro Lys Lys Glu Ser Pro
                165                 170                 175 ggc tgc ctc gag gcc tct gtc acc ttc aac ctc ttc cgc ctc ctc acg      576
Gly Cys Leu Glu Ala Ser Val Thr Phe Asn Leu Phe Arg Leu Leu Thr
            180                 185                 190 cga gac ctg aat tgt gtt gcc agc ggg gac ctg tgt gtc                  615
Arg Asp Leu Asn Cys Val Ala Ser Gly Asp Leu Cys Val
        195                 200                 205

<210> SEQ ID NO 6
<211> LENGTH: 205
<212> TYPE: PRT
<213> ORGANISM: Homo sapiens

<400> SEQUENCE: 6

Met Thr Gly Asp Cys Met Pro Val Leu Val Leu Met Ala Ala Val Leu
 1               5                   10                  15

Thr Val Thr Gly Ala Val Pro Val Ala Arg Leu Arg Gly Ala Leu Pro
                20                  25                  30

Asp Ala Arg Gly Cys His Ile Ala Gln Phe Lys Ser Leu Ser Pro Gln
            35                  40                  45

Glu Leu Gln Ala Phe Lys Arg Ala Lys Asp Ala Leu Glu Glu Ser Leu
        50                  55                  60

Leu Leu Lys Asp Cys Lys Cys Arg Ser Arg Leu Phe Pro Arg Thr Trp
 65                 70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Val Ser Arg Gln Gly Pro Gly Thr
    130                 135                 140

Gln Ile Gln Pro Gln Pro Thr Ala Gly Pro Arg Thr Arg Gly Arg Leu
145                 150                 155                 160
```

```
His His Trp Leu His Arg Leu Gln Glu Ala Pro Lys Glu Ser Pro
            165                 170                 175

Gly Cys Leu Glu Ala Ser Val Thr Phe Asn Leu Phe Arg Leu Leu Thr
        180                 185                 190

Arg Asp Leu Asn Cys Val Ala Ser Gly Asp Leu Cys Val
        195                 200                 205

<210> SEQ ID NO 7
<211> LENGTH: 633
<212> TYPE: DNA
<213> ORGANISM: Mus musculus
<220> FEATURE:
<221> NAME/KEY: CDS
<222> LOCATION: (22)...(630)

<400> SEQUENCE: 7
```

| | | | | | | | | | | | | | | | |
|---|---|---|---|---|---|---|---|---|---|---|---|---|---|---|---|
| tcacagaccc cggagagcaa c | atg | aag | cca | gaa | aca | gct | ggg | ggc | cac | atg | | | | | 51 |
| | Met | Lys | Pro | Glu | Thr | Ala | Gly | Gly | His | Met | | | | | |
| | 1 | | | 5 | | | | | | 10 | | | | | |

```
ctc ctc ctg ctg ttg cct ctg ctg ctg gcc gca gtg ctg aca aga acc    99
Leu Leu Leu Leu Leu Pro Leu Leu Leu Ala Ala Val Leu Thr Arg Thr
            15                  20                  25 caa gct gac cct gtc ccc agg gcc acc agg ctc cca gtg gaa gca aag   147
Gln Ala Asp Pro Val Pro Arg Ala Thr Arg Leu Pro Val Glu Ala Lys
        30                  35                  40 gat tgc cac att gct cag ttc aag tct ctg tcc cca aaa gag ctg cag   195
Asp Cys His Ile Ala Gln Phe Lys Ser Leu Ser Pro Lys Glu Leu Gln
        45                  50                  55 gcc ttc aaa aag gcc aag gat gcc atc gag aag agg ctg ctt gag aag   243
Ala Phe Lys Lys Ala Lys Asp Ala Ile Glu Lys Arg Leu Leu Glu Lys
    60                  65                  70 gac ctg agg tgc agt tcc cac ctc ttc ccc agg gcc tgg gac ctg aag   291
Asp Leu Arg Cys Ser Ser His Leu Phe Pro Arg Ala Trp Asp Leu Lys
75                  80                  85                  90 cag ctg cag gtc caa gag cgc ccc aag gcc ttg cag gct gag gtg gcc   339
Gln Leu Gln Val Gln Glu Arg Pro Lys Ala Leu Gln Ala Glu Val Ala
            95                 100                 105 ctg acc ctg aag gtc tgg gag aac atg act gac tca gcc ctg gcc acc   387
Leu Thr Leu Lys Val Trp Glu Asn Met Thr Asp Ser Ala Leu Ala Thr
        110                 115                 120 atc ctg ggc cag cct ctt cat aca ctg agc cac att cac tcc cag ctg   435
Ile Leu Gly Gln Pro Leu His Thr Leu Ser His Ile His Ser Gln Leu
        125                 130                 135 cag acc tgt aca cag ctt cag gcc aca gca gag ccc agg tcc ccg agc   483
Gln Thr Cys Thr Gln Leu Gln Ala Thr Ala Glu Pro Arg Ser Pro Ser
        140                 145                 150 cgc cgc ctc tcc cgc tgg ctg cac agg ctc cag gag gcc cag agc aag   531
Arg Arg Leu Ser Arg Trp Leu His Arg Leu Gln Glu Ala Gln Ser Lys
155                 160                 165                 170 gag acc cct ggc tgc ctg gag gcc tct gtc acc tcc aac ctg ttt cgc   579
Glu Thr Pro Gly Cys Leu Glu Ala Ser Val Thr Ser Asn Leu Phe Arg
                175                 180                 185 ctg ctc acc cgg gac ctc aag tgt gtg gcc aat gga gac cag tgt gtc   627
Leu Leu Thr Arg Asp Leu Lys Cys Val Ala Asn Gly Asp Gln Cys Val
            190                 195                 200 tga cct                                                            633
 *

<210> SEQ ID NO 8
<211> LENGTH: 202
<212> TYPE: PRT
<213> ORGANISM: Mus musculus
```

<400> SEQUENCE: 8

```
Met Lys Pro Glu Thr Ala Gly Gly His Met Leu Leu Leu Leu Pro
1               5                   10                  15

Leu Leu Leu Ala Ala Val Leu Thr Arg Thr Gln Ala Asp Pro Val Pro
            20                  25                  30

Arg Ala Thr Arg Leu Pro Val Glu Ala Lys Asp Cys His Ile Ala Gln
        35                  40                  45

Phe Lys Ser Leu Ser Pro Lys Glu Leu Gln Ala Phe Lys Lys Ala Lys
    50                  55                  60

Asp Ala Ile Glu Lys Arg Leu Leu Glu Lys Asp Leu Arg Cys Ser Ser
65                  70                  75                  80

His Leu Phe Pro Arg Ala Trp Asp Leu Lys Gln Leu Gln Val Gln Glu
                85                  90                  95

Arg Pro Lys Ala Leu Gln Ala Glu Val Ala Leu Thr Leu Lys Val Trp
            100                 105                 110

Glu Asn Met Thr Asp Ser Ala Leu Ala Thr Ile Leu Gly Gln Pro Leu
        115                 120                 125

His Thr Leu Ser His Ile His Ser Gln Leu Gln Thr Cys Thr Gln Leu
    130                 135                 140

Gln Ala Thr Ala Glu Pro Arg Ser Pro Ser Arg Arg Leu Ser Arg Trp
145                 150                 155                 160

Leu His Arg Leu Gln Glu Ala Gln Ser Lys Glu Thr Pro Gly Cys Leu
                165                 170                 175

Glu Ala Ser Val Thr Ser Asn Leu Phe Arg Leu Leu Thr Arg Asp Leu
            180                 185                 190

Lys Cys Val Ala Asn Gly Asp Gln Cys Val
        195                 200
```

<210> SEQ ID NO 9
<211> LENGTH: 632
<212> TYPE: DNA
<213> ORGANISM: Mus musculus
<220> FEATURE:
<221> NAME/KEY: CDS
<222> LOCATION: (22)...(630)

<400> SEQUENCE: 9

```
tcacagaccc cggagagcaa c atg aag cca gaa aca gct ggg ggc cac atg       51
                        Met Lys Pro Glu Thr Ala Gly Gly His Met
                        1               5                   10 ctc ctc ctg ctg ttg cct ctg ctg ctg gcc gca gtg ctg aca aga acc       99
Leu Leu Leu Leu Leu Pro Leu Leu Leu Ala Ala Val Leu Thr Arg Thr
            15                  20                  25 caa gct gac cct gtc ccc agg gcc acc agg ctc cca gtg gaa gca aag      147
Gln Ala Asp Pro Val Pro Arg Ala Thr Arg Leu Pro Val Glu Ala Lys
        30                  35                  40 gat tgc cac att gct cag ttc aag tct ctg tcc cca aaa gag ctg cag      195
Asp Cys His Ile Ala Gln Phe Lys Ser Leu Ser Pro Lys Glu Leu Gln
    45                  50                  55 gcc ttc aaa aag gcc aag ggt gcc atc gag aag agg ctg ctt gag aag      243
Ala Phe Lys Lys Ala Lys Gly Ala Ile Glu Lys Arg Leu Leu Glu Lys
60                  65                  70 gac atg agg tgc agt tcc cac ctc atc tcc agg gcc tgg gac ctg aag      291
Asp Met Arg Cys Ser Ser His Leu Ile Ser Arg Ala Trp Asp Leu Lys
75                  80                  85                  90 cag ctg cag gtc caa gag cgc ccc aag gcc ttg cag gct gag gtg gcc      339
Gln Leu Gln Val Gln Glu Arg Pro Lys Ala Leu Gln Ala Glu Val Ala
                95                  100                 105
```

```
ctg acc ctg aag gtc tgg gag aac ata aat gac tca gcc ctg acc acc        387
Leu Thr Leu Lys Val Trp Glu Asn Ile Asn Asp Ser Ala Leu Thr Thr
        110                 115                 120 atc ctg ggc cag cct ctt cat aca ctg agc cac att cac tcc cag ctg        435
Ile Leu Gly Gln Pro Leu His Thr Leu Ser His Ile His Ser Gln Leu
    125                 130                 135 cag acc tgt aca cag ctt cag gcc aca gca gag ccc aag ccc ccg agt        483
Gln Thr Cys Thr Gln Leu Gln Ala Thr Ala Glu Pro Lys Pro Pro Ser
140                 145                 150 cgc cgc ctc tcc cgc tgg ctg cac agg ctc cag gag gcc cag agc aag        531
Arg Arg Leu Ser Arg Trp Leu His Arg Leu Gln Glu Ala Gln Ser Lys
155                 160                 165                 170 gag act cct ggc tgc ctg gag gac tct gtc acc tcc aac ctg ttt caa        579
Glu Thr Pro Gly Cys Leu Glu Asp Ser Val Thr Ser Asn Leu Phe Gln
                175                 180                 185 ctg ctc ctc cgg gac ctc aag tgt gtg gcc agt gga gac cag tgt gtc        627
Leu Leu Leu Arg Asp Leu Lys Cys Val Ala Ser Gly Asp Gln Cys Val
            190                 195                 200 tga cc                                                                  632
 *

<210> SEQ ID NO 10
<211> LENGTH: 202
<212> TYPE: PRT
<213> ORGANISM: Mus musculus

<400> SEQUENCE: 10

Met Lys Pro Glu Thr Ala Gly Gly His Met Leu Leu Leu Leu Leu Pro
 1               5                  10                  15

Leu Leu Leu Ala Ala Val Leu Thr Arg Thr Gln Ala Asp Pro Val Pro
            20                  25                  30

Arg Ala Thr Arg Leu Pro Val Glu Ala Lys Asp Cys His Ile Ala Gln
        35                  40                  45

Phe Lys Ser Leu Ser Pro Lys Glu Leu Gln Ala Phe Lys Lys Ala Lys
    50                  55                  60

Gly Ala Ile Glu Lys Arg Leu Leu Glu Lys Asp Met Arg Cys Ser Ser
65                  70                  75                  80

His Leu Ile Ser Arg Ala Trp Asp Leu Lys Gln Leu Gln Val Gln Glu
                85                  90                  95

Arg Pro Lys Ala Leu Gln Ala Glu Val Ala Leu Thr Leu Lys Val Trp
            100                 105                 110

Glu Asn Ile Asn Asp Ser Ala Leu Thr Thr Ile Leu Gly Gln Pro Leu
        115                 120                 125

His Thr Leu Ser His Ile His Ser Gln Leu Gln Thr Cys Thr Gln Leu
    130                 135                 140

Gln Ala Thr Ala Glu Pro Lys Pro Pro Ser Arg Arg Leu Ser Arg Trp
145                 150                 155                 160

Leu His Arg Leu Gln Glu Ala Gln Ser Lys Glu Thr Pro Gly Cys Leu
                165                 170                 175

Glu Asp Ser Val Thr Ser Asn Leu Phe Gln Leu Leu Leu Arg Asp Leu
            180                 185                 190

Lys Cys Val Ala Ser Gly Asp Gln Cys Val
        195                 200

<210> SEQ ID NO 11
<211> LENGTH: 1563
<212> TYPE: DNA
<213> ORGANISM: Homo sapiens
```

```
<220> FEATURE:
<221> NAME/KEY: CDS
<222> LOCATION: (1)...(1563)
<220> FEATURE:
<221> NAME/KEY: misc_feature
<222> LOCATION: (0)...(0)
<223> OTHER INFORMATION: IL-28RA

<400> SEQUENCE: 11
```

| | | | | | | | | | | | | | | | | |
|---|---|---|---|---|---|---|---|---|---|---|---|---|---|---|---|---|
| atg | gcg | ggg | ccc | gag | cgc | tgg | ggc | ccc | ctg | ctc | ctg | tgc | ctg | ctg | cag | 48 |
| Met | Ala | Gly | Pro | Glu | Arg | Trp | Gly | Pro | Leu | Leu | Leu | Cys | Leu | Leu | Gln | |
| 1 | | | | 5 | | | | | 10 | | | | | 15 | | |
| gcc | gct | cca | ggg | agg | ccc | cgt | ctg | gcc | cct | ccc | cag | aat | gtg | acg | ctg | 96 |
| Ala | Ala | Pro | Gly | Arg | Pro | Arg | Leu | Ala | Pro | Pro | Gln | Asn | Val | Thr | Leu | |
| | | | 20 | | | | | 25 | | | | | 30 | | | |
| ctc | tcc | cag | aac | ttc | agc | gtg | tac | ctg | aca | tgg | ctc | cca | ggg | ctt | ggc | 144 |
| Leu | Ser | Gln | Asn | Phe | Ser | Val | Tyr | Leu | Thr | Trp | Leu | Pro | Gly | Leu | Gly | |
| | | 35 | | | | | 40 | | | | | 45 | | | | |
| aac | ccc | cag | gat | gtg | acc | tat | ttt | gtg | gcc | tat | cag | agc | tct | ccc | acc | 192 |
| Asn | Pro | Gln | Asp | Val | Thr | Tyr | Phe | Val | Ala | Tyr | Gln | Ser | Ser | Pro | Thr | |
| | 50 | | | | | 55 | | | | | 60 | | | | | |
| cgt | aga | cgg | tgg | cgc | gaa | gtg | gaa | gag | tgt | gcg | gga | acc | aag | gag | ctg | 240 |
| Arg | Arg | Arg | Trp | Arg | Glu | Val | Glu | Glu | Cys | Ala | Gly | Thr | Lys | Glu | Leu | |
| 65 | | | | 70 | | | | | 75 | | | | | 80 | | |
| cta | tgt | tct | atg | atg | tgc | ctg | aag | aaa | cag | gac | ctg | tac | aac | aag | ttc | 288 |
| Leu | Cys | Ser | Met | Met | Cys | Leu | Lys | Lys | Gln | Asp | Leu | Tyr | Asn | Lys | Phe | |
| | | | | 85 | | | | | 90 | | | | | 95 | | |
| aag | gga | cgc | gtg | cgg | acg | gtt | tct | ccc | agc | tcc | aag | tcc | ccc | tgg | gtg | 336 |
| Lys | Gly | Arg | Val | Arg | Thr | Val | Ser | Pro | Ser | Ser | Lys | Ser | Pro | Trp | Val | |
| | | | 100 | | | | | 105 | | | | | 110 | | | |
| gag | tcc | gaa | tac | ctg | gat | tac | ctt | ttt | gaa | gtg | gag | ccg | gcc | cca | cct | 384 |
| Glu | Ser | Glu | Tyr | Leu | Asp | Tyr | Leu | Phe | Glu | Val | Glu | Pro | Ala | Pro | Pro | |
| | | 115 | | | | | 120 | | | | | 125 | | | | |
| gtc | ctg | gtg | ctc | acc | cag | acg | gag | gag | atc | ctg | agt | gcc | aat | gcc | acg | 432 |
| Val | Leu | Val | Leu | Thr | Gln | Thr | Glu | Glu | Ile | Leu | Ser | Ala | Asn | Ala | Thr | |
| | 130 | | | | | 135 | | | | | 140 | | | | | |
| tac | cag | ctg | ccc | ccc | tgc | atg | ccc | cca | ctg | gat | ctg | aag | tat | gag | gtg | 480 |
| Tyr | Gln | Leu | Pro | Pro | Cys | Met | Pro | Pro | Leu | Asp | Leu | Lys | Tyr | Glu | Val | |
| 145 | | | | | 150 | | | | | 155 | | | | | 160 | |
| gca | ttc | tgg | aag | gag | ggg | gcc | gga | aac | aag | acc | cta | ttt | cca | gtc | act | 528 |
| Ala | Phe | Trp | Lys | Glu | Gly | Ala | Gly | Asn | Lys | Thr | Leu | Phe | Pro | Val | Thr | |
| | | | | 165 | | | | | 170 | | | | | 175 | | |
| ccc | cat | ggc | cag | cca | gtc | cag | atc | act | ctc | cag | cca | gct | gcc | agc | gaa | 576 |
| Pro | His | Gly | Gln | Pro | Val | Gln | Ile | Thr | Leu | Gln | Pro | Ala | Ala | Ser | Glu | |
| | | | 180 | | | | | 185 | | | | | 190 | | | |
| cac | cac | tgc | ctc | agt | gcc | aga | acc | atc | tac | acg | ttc | agt | gtc | ccg | aaa | 624 |
| His | His | Cys | Leu | Ser | Ala | Arg | Thr | Ile | Tyr | Thr | Phe | Ser | Val | Pro | Lys | |
| | | 195 | | | | | 200 | | | | | 205 | | | | |
| tac | agc | aag | ttc | tct | aag | ccc | acc | tgc | ttc | ttg | ctg | gag | gtc | cca | gaa | 672 |
| Tyr | Ser | Lys | Phe | Ser | Lys | Pro | Thr | Cys | Phe | Leu | Leu | Glu | Val | Pro | Glu | |
| | 210 | | | | | 215 | | | | | 220 | | | | | |
| gcc | aac | tgg | gct | ttc | ctg | gtg | ctg | cca | tcg | ctt | ctg | ata | ctg | ctg | tta | 720 |
| Ala | Asn | Trp | Ala | Phe | Leu | Val | Leu | Pro | Ser | Leu | Leu | Ile | Leu | Leu | Leu | |
| 225 | | | | | 230 | | | | | 235 | | | | | 240 | |
| gta | att | gcc | gca | ggg | ggt | gtg | atc | tgg | aag | acc | ctc | atg | ggg | aac | ccc | 768 |
| Val | Ile | Ala | Ala | Gly | Gly | Val | Ile | Trp | Lys | Thr | Leu | Met | Gly | Asn | Pro | |
| | | | | 245 | | | | | 250 | | | | | 255 | | |
| tgg | ttt | cag | cgg | gca | aag | atg | cca | cgg | gcc | ctg | gac | ttt | tct | gga | cac | 816 |
| Trp | Phe | Gln | Arg | Ala | Lys | Met | Pro | Arg | Ala | Leu | Asp | Phe | Ser | Gly | His | |
| | | | 260 | | | | | 265 | | | | | 270 | | | |
| aca | cac | cct | gtg | gca | acc | ttt | cag | ccc | agc | aga | cca | gag | tcc | gtg | aat | 864 |
| Thr | His | Pro | Val | Ala | Thr | Phe | Gln | Pro | Ser | Arg | Pro | Glu | Ser | Val | Asn | |

```
                275                 280                 285
gac ttg ttc ctc tgt ccc caa aag gaa ctg acc aga ggg gtc agg ccg      912
Asp Leu Phe Leu Cys Pro Gln Lys Glu Leu Thr Arg Gly Val Arg Pro
290                 295                 300 acg cct cga gtc agg gcc cca gcc acc caa cag aca aga tgg aag aag      960
Thr Pro Arg Val Arg Ala Pro Ala Thr Gln Gln Thr Arg Trp Lys Lys
305                 310                 315                 320 gac ctt gca gag gac gaa gag gag gat gag gag gac aca gaa gat         1008
Asp Leu Ala Glu Asp Glu Glu Glu Asp Glu Glu Asp Thr Glu Asp
                325                 330                 335 ggc gtc agc ttc cag ccc tac att gaa cca cct tct ttc ctg ggg caa     1056
Gly Val Ser Phe Gln Pro Tyr Ile Glu Pro Pro Ser Phe Leu Gly Gln
            340                 345                 350 gag cac cag gct cca ggg cac tcg gag gct ggt ggg gtg gac tca ggg     1104
Glu His Gln Ala Pro Gly His Ser Glu Ala Gly Gly Val Asp Ser Gly
        355                 360                 365 agg ccc agg gct cct ctg gtc cca agc gaa ggc tcc tct gct tgg gat     1152
Arg Pro Arg Ala Pro Leu Val Pro Ser Glu Gly Ser Ser Ala Trp Asp
    370                 375                 380 tct tca gac aga agc tgg gcc agc act gtg gac tcc tcc tgg gac agg     1200
Ser Ser Asp Arg Ser Trp Ala Ser Thr Val Asp Ser Ser Trp Asp Arg
385                 390                 395                 400 gct ggg tcc tct ggc tat ttg gct gag aag ggg cca ggc caa ggg ccg     1248
Ala Gly Ser Ser Gly Tyr Leu Ala Glu Lys Gly Pro Gly Gln Gly Pro
                405                 410                 415 ggt ggg gat ggg cac caa gaa tct ctc cca cca cct gaa ttc tcc aag     1296
Gly Gly Asp Gly His Gln Glu Ser Leu Pro Pro Pro Glu Phe Ser Lys
            420                 425                 430 gac tcg ggt ttc ctg gaa gag ctc cca gaa gat aac ctc tcc tcc tgg     1344
Asp Ser Gly Phe Leu Glu Glu Leu Pro Glu Asp Asn Leu Ser Ser Trp
        435                 440                 445 gcc acc tgg ggc acc tta cca ccg gag ccg aat ctg gtc cct ggg gga    1392
Ala Thr Trp Gly Thr Leu Pro Pro Glu Pro Asn Leu Val Pro Gly Gly
    450                 455                 460 ccc cca gtt tct ctt cag aca ctg acc ttc tgc tgg gaa agc agc cct    1440
Pro Pro Val Ser Leu Gln Thr Leu Thr Phe Cys Trp Glu Ser Ser Pro
465                 470                 475                 480 gag gag gaa gag gag gcg agg gaa tca gaa att gag gac agc gat gcg    1488
Glu Glu Glu Glu Glu Ala Arg Glu Ser Glu Ile Glu Asp Ser Asp Ala
                485                 490                 495 ggc agc tgg ggg gct gag agc acc cag agg acc gag gac agg ggc cgg    1536
Gly Ser Trp Gly Ala Glu Ser Thr Gln Arg Thr Glu Asp Arg Gly Arg
            500                 505                 510 aca ttg ggg cat tac atg gcc agg tga                                1563
Thr Leu Gly His Tyr Met Ala Arg  *
        515                 520

<210> SEQ ID NO 12
<211> LENGTH: 520
<212> TYPE: PRT
<213> ORGANISM: Homo sapiens

<400> SEQUENCE: 12

Met Ala Gly Pro Glu Arg Trp Gly Pro Leu Leu Cys Leu Leu Gln
1               5                   10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
```

-continued

```
            50                  55                  60
Arg Arg Arg Trp Arg Glu Val Glu Glu Cys Ala Gly Thr Lys Glu Leu
 65                  70                  75                  80

Leu Cys Ser Met Met Cys Leu Lys Lys Gln Asp Leu Tyr Asn Lys Phe
                 85                  90                  95

Lys Gly Arg Val Arg Thr Val Ser Pro Ser Lys Ser Pro Trp Val
                100                 105                 110

Glu Ser Glu Tyr Leu Asp Tyr Leu Phe Glu Val Glu Pro Ala Pro Pro
            115                 120                 125

Val Leu Val Leu Thr Gln Thr Glu Glu Ile Leu Ser Ala Asn Ala Thr
        130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
210                 215                 220

Ala Asn Trp Ala Phe Leu Val Leu Pro Ser Leu Ile Leu Leu Leu
225                 230                 235                 240

Val Ile Ala Ala Gly Gly Val Ile Trp Lys Thr Leu Met Gly Asn Pro
                245                 250                 255

Trp Phe Gln Arg Ala Lys Met Pro Arg Ala Leu Asp Phe Ser Gly His
            260                 265                 270

Thr His Pro Val Ala Thr Phe Gln Pro Ser Arg Pro Glu Ser Val Asn
        275                 280                 285

Asp Leu Phe Leu Cys Pro Gln Lys Glu Leu Thr Arg Gly Val Arg Pro
290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Asp Glu Asp Thr Glu Asp
                325                 330                 335

Gly Val Ser Phe Gln Pro Tyr Ile Glu Pro Pro Ser Phe Leu Gly Gln
            340                 345                 350

Glu His Gln Ala Pro Gly His Ser Glu Ala Gly Gly Val Asp Ser Gly
        355                 360                 365

Arg Pro Arg Ala Pro Leu Val Pro Ser Glu Gly Ser Ser Ala Trp Asp
370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                405                 410                 415

Gly Gly Asp Gly His Gln Glu Ser Leu Pro Pro Glu Phe Ser Lys
            420                 425                 430

Asp Ser Gly Phe Leu Glu Glu Leu Pro Glu Asp Asn Leu Ser Ser Trp
        435                 440                 445

Ala Thr Trp Gly Thr Leu Pro Pro Glu Pro Asn Leu Val Pro Gly Gly
    450                 455                 460

Pro Pro Val Ser Leu Gln Thr Leu Thr Phe Cys Trp Glu Ser Ser Pro
465                 470                 475                 480
```

```
Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
            500                 505                 510

Thr Leu Gly His Tyr Met Ala Arg
            515                 520

<210> SEQ ID NO 13
<211> LENGTH: 1476
<212> TYPE: DNA
<213> ORGANISM: Homo sapiens
<220> FEATURE:
<221> NAME/KEY: CDS
<222> LOCATION: (1)...(1476)
<220> FEATURE:
<221> NAME/KEY: misc_feature
<222> LOCATION: (0)...(0)
<223> OTHER INFORMATION: IL-28RA splice variant

<400> SEQUENCE: 13 atg gcg ggg ccc gag cgc tgg ggc ccc ctg ctc ctg tgc ctg ctg cag    48
Met Ala Gly Pro Glu Arg Trp Gly Pro Leu Leu Leu Cys Leu Leu Gln
 1               5                  10                  15 gcc gct cca ggg agg ccc cgt ctg gcc cct ccc cag aat gtg acg ctg    96
Ala Ala Pro Gly Arg Pro Arg Leu Ala Pro Pro Gln Asn Val Thr Leu
                20                  25                  30 ctc tcc cag aac ttc agc gtg tac ctg aca tgg ctc cca ggg ctt ggc   144
Leu Ser Gln Asn Phe Ser Val Tyr Leu Thr Trp Leu Pro Gly Leu Gly
            35                  40                  45 aac ccc cag gat gtg acc tat ttt gtg gcc tat cag agc tct ccc acc   192
Asn Pro Gln Asp Val Thr Tyr Phe Val Ala Tyr Gln Ser Ser Pro Thr
        50                  55                  60 cgt aga cgg tgg cgc gaa gtg gaa gag tgt gcg gga acc aag gag ctg   240
Arg Arg Arg Trp Arg Glu Val Glu Glu Cys Ala Gly Thr Lys Glu Leu
 65                  70                  75                  80 cta tgt tct atg atg tgc ctg aag aaa cag gac ctg tac aac aag ttc   288
Leu Cys Ser Met Met Cys Leu Lys Lys Gln Asp Leu Tyr Asn Lys Phe
                 85                  90                  95 aag gga cgc gtg cgg acg gtt tct ccc agc tcc aag tcc ccc tgg gtg   336
Lys Gly Arg Val Arg Thr Val Ser Pro Ser Ser Lys Ser Pro Trp Val
            100                 105                 110 gag tcc gaa tac ctg gat tac ctt ttt gaa gtg gag ccg gcc cca cct   384
Glu Ser Glu Tyr Leu Asp Tyr Leu Phe Glu Val Glu Pro Ala Pro Pro
        115                 120                 125 gtc ctg gtg ctc acc cag acg gag gag atc ctg agt gcc aat gcc acg   432
Val Leu Val Leu Thr Gln Thr Glu Glu Ile Leu Ser Ala Asn Ala Thr
    130                 135                 140 tac cag ctg ccc ccc tgc atg ccc cca ctg ttt ctg aag tat gag gtg   480
Tyr Gln Leu Pro Pro Cys Met Pro Pro Leu Phe Leu Lys Tyr Glu Val
145                 150                 155                 160 gca ttt tgg ggg ggg ggg gcc gga acc aag acc cta ttt cca gtc act   528
Ala Phe Trp Gly Gly Gly Ala Gly Thr Lys Thr Leu Phe Pro Val Thr
                165                 170                 175 ccc cat ggc cag cca gtc cag atc act ctc cag cca gct gcc agc gaa   576
Pro His Gly Gln Pro Val Gln Ile Thr Leu Gln Pro Ala Ala Ser Glu
            180                 185                 190 cac cac tgc ctc agt gcc aga acc atc tac acg ttc agt gtc ccg aaa   624
His His Cys Leu Ser Ala Arg Thr Ile Tyr Thr Phe Ser Val Pro Lys
        195                 200                 205 tac agc aag ttc tct aag ccc acc tgc ttc ttg ctg gag gtc cca gaa   672
Tyr Ser Lys Phe Ser Lys Pro Thr Cys Phe Leu Leu Glu Val Pro Glu
    210                 215                 220
```

| | | |
|---|---|---|
| gcc aac tgg gct ttc ctg gtg ctg cca tcg ctt ctg ata ctg ctg tta<br>Ala Asn Trp Ala Phe Leu Val Leu Pro Ser Leu Leu Ile Leu Leu Leu<br>225                            230                        235                      240 | | 720 |
| gta att gcc gca ggg ggt gtg atc tgg aag acc ctc atg ggg aac ccc<br>Val Ile Ala Ala Gly Gly Val Ile Trp Lys Thr Leu Met Gly Asn Pro<br>                     245                        250                        255 | | 768 |
| tgg ttt cag cgg gca aag atg cca cgg gcc ctg gaa ctg acc aga ggg<br>Trp Phe Gln Arg Ala Lys Met Pro Arg Ala Leu Glu Leu Thr Arg Gly<br>              260                        265                        270 | | 816 |
| gtc agg ccg acg cct cga gtc agg gcc cca gcc acc caa cag aca aga<br>Val Arg Pro Thr Pro Arg Val Arg Ala Pro Ala Thr Gln Gln Thr Arg<br>275                            280                        285 | | 864 |
| tgg aag aag gac ctt gca gag gac gaa gag gag gat gag gag gac<br>Trp Lys Lys Asp Leu Ala Glu Asp Glu Glu Glu Asp Glu Glu Asp<br>290                            295                        300 | | 912 |
| aca gaa gat ggc gtc agc ttc cag ccc tac att gaa cca cct tct ttc<br>Thr Glu Asp Gly Val Ser Phe Gln Pro Tyr Ile Glu Pro Pro Ser Phe<br>305                            310                        315                        320 | | 960 |
| ctg ggg caa gag cac cag gct cca ggg cac tcg gag gct ggt ggg gtg<br>Leu Gly Gln Glu His Gln Ala Pro Gly His Ser Glu Ala Gly Gly Val<br>                     325                        330                        335 | | 1008 |
| gac tca ggg agg ccc agg gct cct ctg gtc cca agc gaa ggc tcc tct<br>Asp Ser Gly Arg Pro Arg Ala Pro Leu Val Pro Ser Glu Gly Ser Ser<br>                     340                        345                        350 | | 1056 |
| gct tgg gat tct tca gac aga agc tgg gcc agc act gtg gac tcc tcc<br>Ala Trp Asp Ser Ser Asp Arg Ser Trp Ala Ser Thr Val Asp Ser Ser<br>355                            360                        365 | | 1104 |
| tgg gac agg gct ggg tcc tct ggc tat ttg gct gag aag ggg cca ggc<br>Trp Asp Arg Ala Gly Ser Ser Gly Tyr Leu Ala Glu Lys Gly Pro Gly<br>     370                        375                        380 | | 1152 |
| caa ggg ccg ggt ggg gat ggg cac caa gaa tct ctc cca cca cct gaa<br>Gln Gly Pro Gly Gly Asp Gly His Gln Glu Ser Leu Pro Pro Pro Glu<br>385                            390                        395                        400 | | 1200 |
| ttc tcc aag gac tcg ggt ttc ctg gaa gag ctc cca gaa gat aac ctc<br>Phe Ser Lys Asp Ser Gly Phe Leu Glu Glu Leu Pro Glu Asp Asn Leu<br>                     405                        410                        415 | | 1248 |
| tcc tcc tgg gcc acc tgg ggc acc tta cca ccg gag ccg aat ctg gtc<br>Ser Ser Trp Ala Thr Trp Gly Thr Leu Pro Pro Glu Pro Asn Leu Val<br>                     420                        425                        430 | | 1296 |
| cct ggg gga ccc cca gtt tct ctt cag aca ctg acc ttc tgc tgg gaa<br>Pro Gly Gly Pro Pro Val Ser Leu Gln Thr Leu Thr Phe Cys Trp Glu<br>                     435                        440                        445 | | 1344 |
| agc agc cct gag gag gaa gag gag gcg agg gaa tca gaa att gag gac<br>Ser Ser Pro Glu Glu Glu Glu Glu Ala Arg Glu Ser Glu Ile Glu Asp<br>450                            455                        460 | | 1392 |
| agc gat gcg ggc agc tgg ggg gct gag agc acc cag agg acc gag gac<br>Ser Asp Ala Gly Ser Trp Gly Ala Glu Ser Thr Gln Arg Thr Glu Asp<br>465                            470                        475                        480 | | 1440 |
| agg ggc cgg aca ttg ggg cat tac atg gcc agg tga<br>Arg Gly Arg Thr Leu Gly His Tyr Met Ala Arg  *<br>                     485                        490 | | 1476 |

```
<210> SEQ ID NO 14
<211> LENGTH: 491
<212> TYPE: PRT
<213> ORGANISM: Homo sapiens

<400> SEQUENCE: 14
```

Met Ala Gly Pro Glu Arg Trp Gly Pro Leu Leu Leu Cys Leu Leu Gln
1                  5                       10                     15

Ala Ala Pro Gly Arg Pro Arg Leu Ala Pro Pro Gln Asn Val Thr Leu

```
                 20                  25                  30
Leu Ser Gln Asn Phe Ser Val Tyr Leu Thr Trp Leu Pro Gly Leu Gly
             35                  40                  45
Asn Pro Gln Asp Val Thr Tyr Phe Val Ala Tyr Gln Ser Ser Pro Thr
 50                  55                  60
Arg Arg Arg Trp Arg Glu Val Glu Glu Cys Ala Gly Thr Lys Glu Leu
 65                  70                  75                  80
Leu Cys Ser Met Met Cys Leu Lys Lys Gln Asp Leu Tyr Asn Lys Phe
                 85                  90                  95
Lys Gly Arg Val Arg Thr Val Ser Pro Ser Ser Lys Ser Pro Trp Val
                100                 105                 110
Glu Ser Glu Tyr Leu Asp Tyr Leu Phe Glu Val Glu Pro Ala Pro Pro
            115                 120                 125
Val Leu Val Leu Thr Gln Thr Glu Glu Ile Leu Ser Ala Asn Ala Thr
            130                 135                 140
Tyr Gln Leu Pro Pro Cys Met Pro Pro Leu Phe Leu Lys Tyr Glu Val
145                 150                 155                 160
Ala Phe Trp Gly Gly Gly Ala Gly Thr Lys Thr Leu Phe Pro Val Thr
                165                 170                 175
Pro His Gly Gln Pro Val Gln Ile Thr Leu Gln Pro Ala Ala Ser Glu
            180                 185                 190
His His Cys Leu Ser Ala Arg Thr Ile Tyr Thr Phe Ser Val Pro Lys
            195                 200                 205
Tyr Ser Lys Phe Ser Lys Pro Thr Cys Phe Leu Leu Glu Val Pro Glu
    210                 215                 220
Ala Asn Trp Ala Phe Leu Val Leu Pro Ser Leu Leu Ile Leu Leu Leu
225                 230                 235                 240
Val Ile Ala Ala Gly Gly Val Ile Trp Lys Thr Leu Met Gly Asn Pro
                245                 250                 255
Trp Phe Gln Arg Ala Lys Met Pro Arg Ala Leu Glu Leu Thr Arg Gly
            260                 265                 270
Val Arg Pro Thr Pro Arg Val Arg Ala Pro Ala Thr Gln Gln Thr Arg
            275                 280                 285
Trp Lys Lys Asp Leu Ala Glu Asp Glu Glu Glu Asp Glu Glu Asp
    290                 295                 300
Thr Glu Asp Gly Val Ser Phe Gln Pro Tyr Ile Glu Pro Ser Phe
305                 310                 315                 320
Leu Gly Gln Glu His Gln Ala Pro Gly His Ser Glu Ala Gly Val
                325                 330                 335
Asp Ser Gly Arg Pro Arg Ala Pro Leu Val Pro Ser Glu Gly Ser Ser
            340                 345                 350
Ala Trp Asp Ser Ser Asp Arg Ser Trp Ala Ser Thr Val Asp Ser Ser
            355                 360                 365
Trp Asp Arg Ala Gly Ser Ser Gly Tyr Leu Ala Glu Lys Gly Pro Gly
    370                 375                 380
Gln Gly Pro Gly Gly Asp Gly His Gln Glu Ser Leu Pro Pro Pro Glu
385                 390                 395                 400
Phe Ser Lys Asp Ser Gly Phe Leu Glu Glu Leu Pro Glu Asp Asn Leu
                405                 410                 415
Ser Ser Trp Ala Thr Trp Gly Thr Leu Pro Pro Glu Pro Asn Leu Val
            420                 425                 430
Pro Gly Gly Pro Pro Val Ser Leu Gln Thr Leu Thr Phe Cys Trp Glu
            435                 440                 445
```

```
Ser Ser Pro Glu Glu Glu Glu Ala Arg Glu Ser Glu Ile Glu Asp
    450                 455                 460

Ser Asp Ala Gly Ser Trp Gly Ala Glu Ser Thr Gln Arg Thr Glu Asp
465                 470                 475                 480

Arg Gly Arg Thr Leu Gly His Tyr Met Ala Arg
                485                 490

<210> SEQ ID NO 15
<211> LENGTH: 674
<212> TYPE: DNA
<213> ORGANISM: Homo sapiens
<220> FEATURE:
<221> NAME/KEY: CDS
<222> LOCATION: (1)...(636)
<220> FEATURE:
<221> NAME/KEY: misc_feature
<222> LOCATION: (0)...(0)
<223> OTHER INFORMATION: IL-28RA soluble variant

<400> SEQUENCE: 15 atg gcg ggg ccc gag cgc tgg ggc ccc ctg ctc ctg tgc ctg ctg cag      48
Met Ala Gly Pro Glu Arg Trp Gly Pro Leu Leu Leu Cys Leu Leu Gln
1               5                   10                  15 gcc gct cca ggg agg ccc cgt ctg gcc cct ccc cag aat gtg acg ctg      96
Ala Ala Pro Gly Arg Pro Arg Leu Ala Pro Pro Gln Asn Val Thr Leu
                20                  25                  30 ctc tcc cag aac ttc agc gtg tac ctg aca tgg ctc cca ggg ctt ggc     144
Leu Ser Gln Asn Phe Ser Val Tyr Leu Thr Trp Leu Pro Gly Leu Gly
            35                  40                  45 aac ccc cag gat gtg acc tat ttt gtg gcc tat cag agc tct ccc acc     192
Asn Pro Gln Asp Val Thr Tyr Phe Val Ala Tyr Gln Ser Ser Pro Thr
        50                  55                  60 cgt aga cgg tgg cgc gaa gtg gaa gag tgt gcg gga acc aag gag ctg     240
Arg Arg Arg Trp Arg Glu Val Glu Glu Cys Ala Gly Thr Lys Glu Leu
65                  70                  75                  80 cta tgt tct atg atg tgc ctg aag aaa cag gac ctg tac aac aag ttc     288
Leu Cys Ser Met Met Cys Leu Lys Lys Gln Asp Leu Tyr Asn Lys Phe
                85                  90                  95 aag gga cgc gtg cgg acg gtt tct ccc agc tcc aag tcc ccc tgg gtg     336
Lys Gly Arg Val Arg Thr Val Ser Pro Ser Ser Lys Ser Pro Trp Val
                100                 105                 110 gag tcc gaa tac ctg gat tac ctt ttt gaa gtg gag ccg gcc cca cct     384
Glu Ser Glu Tyr Leu Asp Tyr Leu Phe Glu Val Glu Pro Ala Pro Pro
            115                 120                 125 gtc ctg gtg ctc acc cag acg gag gag atc ctg agt gcc aat gcc acg     432
Val Leu Val Leu Thr Gln Thr Glu Glu Ile Leu Ser Ala Asn Ala Thr
        130                 135                 140 tac cag ctg ccc ccc tgc atg ccc cca ctg gat ctg aag tat gag gtg     480
Tyr Gln Leu Pro Pro Cys Met Pro Pro Leu Asp Leu Lys Tyr Glu Val
145                 150                 155                 160 gca ttc tgg aag gag ggg gcc gga aac aag gtg gga agc tcc ttt cct     528
Ala Phe Trp Lys Glu Gly Ala Gly Asn Lys Val Gly Ser Ser Phe Pro
                165                 170                 175 gcc ccc agg cta ggc ccg ctc ctc cac ccc ttc tta ctc agg ttc ttc     576
Ala Pro Arg Leu Gly Pro Leu Leu His Pro Phe Leu Leu Arg Phe Phe
            180                 185                 190 tca ccc tcc cag cct gct cct gca ccc ctc ctc cag gaa gtc ttc cct     624
Ser Pro Ser Gln Pro Ala Pro Ala Pro Leu Leu Gln Glu Val Phe Pro
        195                 200                 205 gta cac tcc tga cttctggcag tcagccctaa taaaatctga tcaaagta           674
Val His Ser *
    210
```

-continued

```
<210> SEQ ID NO 16
<211> LENGTH: 211
<212> TYPE: PRT
<213> ORGANISM: Homo sapiens

<400> SEQUENCE: 16

Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
                20                  25                  30

Leu Ser Gln Asn Phe Ser Val Tyr Leu Thr Trp Leu Pro Gly Leu Gly
            35                  40                  45

Asn Pro Gln Asp Val Thr Tyr Phe Val Ala Tyr Gln Ser Ser Pro Thr
        50                  55                  60

Arg Arg Arg Trp Arg Glu Val Glu Glu Cys Ala Gly Thr Lys Glu Leu
 65                 70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
                100                 105                 110

Glu Ser Glu Tyr Leu Asp Tyr Leu Phe Glu Val Glu Pro Ala Pro Pro
            115                 120                 125

Val Leu Val Leu Thr Gln Thr Glu Glu Ile Leu Ser Ala Asn Ala Thr
        130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Val Gly Ser Ser Phe Pro
                165                 170                 175

Ala Pro Arg Leu Gly Pro Leu Leu His Pro Phe Leu Leu Arg Phe Phe
            180                 185                 190

Ser Pro Ser Gln Pro Ala Pro Ala Pro Leu Leu Gln Glu Val Phe Pro
        195                 200                 205

Val His Ser
210

<210> SEQ ID NO 17
<211> LENGTH: 734
<212> TYPE: DNA
<213> ORGANISM: Homo sapiens
<220> FEATURE:
<221> NAME/KEY: sig_peptide
<222> LOCATION: (53)...(127)
<220> FEATURE:
<221> NAME/KEY: mat_peptide
<222> LOCATION: (128)...(655)
<220> FEATURE:
<221> NAME/KEY: CDS
<222> LOCATION: (53)...(655)

<400> SEQUENCE: 17
tgggtgacag cctcagagtg tttcttctgc tgacaaagac cagagatcag ga atg aaa      58
                                                          Met Lys
                                                          -25 cta gac atg act ggg gac tgc acg cca gtg ctg gtg ctg atg gcc gca      106
Leu Asp Met Thr Gly Asp Cys Thr Pro Val Leu Val Leu Met Ala Ala
        -20                 -15                 -10 gtg ctg acc gtg act gga gca gtt cct gtc gcc agg ctc cac ggg gct      154
Val Leu Thr Val Thr Gly Ala Val Pro Val Ala Arg Leu His Gly Ala
    -5                   1                   5 ctc ccg gat gca agg ggc tgc cac ata gcc cag ttc aag tcc ctg tct      202
```

```
                Leu Pro Asp Ala Arg Gly Cys His Ile Ala Gln Phe Lys Ser Leu Ser
                 10                  15                  20                  25 cca cag gag ctg cag gcc ttt aag agg gcc aaa gat gcc tta gaa gag              250
Pro Gln Glu Leu Gln Ala Phe Lys Arg Ala Lys Asp Ala Leu Glu Glu
                 30                  35                  40 tcg ctt ctg ctg aag gac tgc agg tgc cac tcc cgc ctc ttc ccc agg              298
Ser Leu Leu Leu Lys Asp Cys Arg Cys His Ser Arg Leu Phe Pro Arg
                 45                  50                  55 acc tgg gac ctg agg cag ctg cag gtg agg gag cgc ccc atg gct ttg              346
Thr Trp Asp Leu Arg Gln Leu Gln Val Arg Glu Arg Pro Met Ala Leu
                 60                  65                  70 gag gct gag ctg gcc ctg acg ctg aag gtt ctg gag gcc acc gct gac              394
Glu Ala Glu Leu Ala Leu Thr Leu Lys Val Leu Glu Ala Thr Ala Asp
        75                  80                  85 act gac cca gcc ctg gtg gac gtc ttg gac cag ccc ctt cac acc ctg              442
Thr Asp Pro Ala Leu Val Asp Val Leu Asp Gln Pro Leu His Thr Leu
 90                  95                 100                 105 cac cat atc ctc tcc cag ttc cgg gcc tgt atc cag cct cag ccc acg              490
His His Ile Leu Ser Gln Phe Arg Ala Cys Ile Gln Pro Gln Pro Thr
                    110                 115                 120 gca ggg ccc agg acc cgg ggc cgc ctc cac cat tgg ctg tac cgg ctc              538
Ala Gly Pro Arg Thr Arg Gly Arg Leu His His Trp Leu Tyr Arg Leu
             125                 130                 135 cag gag gcc cca aaa aag gag tcc cct ggc tgc ctc gag gcc tct gtc              586
Gln Glu Ala Pro Lys Lys Glu Ser Pro Gly Cys Leu Glu Ala Ser Val
             140                 145                 150 acc ttc aac ctc ttc cgc ctc ctc acg cga gac ctg aat tgt gtt gcc              634
Thr Phe Asn Leu Phe Arg Leu Leu Thr Arg Asp Leu Asn Cys Val Ala
     155                 160                 165 agt ggg gac ctg tgt gtc tga ccctcccacc agtcatgcaa cctgagattt                 685
Ser Gly Asp Leu Cys Val  *
170                 175 tatttataaa ttagccactt gtcttaattt attgccaccc agtcgctat                        734

<210> SEQ ID NO 18
<211> LENGTH: 200
<212> TYPE: PRT
<213> ORGANISM: Homo sapiens
<220> FEATURE:
<221> NAME/KEY: SIGNAL
<222> LOCATION: (1)...(25)

<400> SEQUENCE: 18

Met Lys Leu Asp Met Thr Gly Asp Cys Thr Pro Val Leu Val Leu Met
-25                 -20                 -15                 -10

Ala Ala Val Leu Thr Val Thr Gly Ala Val Pro Val Ala Arg Leu His
         -5                   1                   5

Gly Ala Leu Pro Asp Ala Arg Gly Cys His Ile Ala Gln Phe Lys Ser
             10                  15                  20

Leu Ser Pro Gln Glu Leu Gln Ala Phe Lys Arg Ala Lys Asp Ala Leu
     25                  30                  35

Glu Glu Ser Leu Leu Lys Asp Cys Arg Cys His Ser Arg Leu Phe
 40                  45                  50                  55

Pro Arg Thr Trp Asp Leu Arg Gln Leu Gln Val Arg Glu Arg Pro Met
                 60                  65                  70

Ala Leu Glu Ala Glu Leu Ala Leu Thr Leu Lys Val Leu Glu Ala Thr
             75                  80                  85

Ala Asp Thr Asp Pro Ala Leu Val Asp Val Leu Asp Gln Pro Leu His
         90                  95                 100
```

```
Thr Leu His His Ile Leu Ser Gln Phe Arg Ala Cys Ile Gln Pro Gln
        105                 110                 115

Pro Thr Ala Gly Pro Arg Thr Arg Gly Arg Leu His His Trp Leu Tyr
120                 125                 130                 135

Arg Leu Gln Glu Ala Pro Lys Lys Glu Ser Pro Gly Cys Leu Glu Ala
                140                 145                 150

Ser Val Thr Phe Asn Leu Phe Arg Leu Leu Thr Arg Asp Leu Asn Cys
                155                 160                 165

Val Ala Ser Gly Asp Leu Cys Val
        170                 175

<210> SEQ ID NO 19
<211> LENGTH: 856
<212> TYPE: DNA
<213> ORGANISM: Homo sapiens
<220> FEATURE:
<221> NAME/KEY: sig_peptide
<222> LOCATION: (98)...(154)
<220> FEATURE:
<221> NAME/KEY: mat_peptide
<222> LOCATION: (155)...(700)
<220> FEATURE:
<221> NAME/KEY: CDS
<222> LOCATION: (98)...(700)

<400> SEQUENCE: 19
aattaccttt tcactttaca cacatcatct tggattgccc attttgcgtg gctaaaaagc      60
agagccatgc cgctggggaa gcagttgcga tttagcc atg gct gca gct tgg acc     115
                                        Met Ala Ala Ala Trp Thr
                                                        -15 gtg gtg ctg gtg act ttg gtg cta ggc ttg gcc gtg gca ggc cct gtc     163
Val Val Leu Val Thr Leu Val Leu Gly Leu Ala Val Ala Gly Pro Val
        -10                  -5                   1 ccc act tcc aag ccc acc aca act ggg aag ggc tgc cac att ggc agg     211
Pro Thr Ser Lys Pro Thr Thr Thr Gly Lys Gly Cys His Ile Gly Arg
    5                   10                  15 ttc aaa tct ctg tca cca cag gag cta gcg agc ttc aag aag gcc agg     259
Phe Lys Ser Leu Ser Pro Gln Glu Leu Ala Ser Phe Lys Lys Ala Arg
 20                  25                  30                  35 gac gcc ttg gaa gag tca ctc aag ctg aaa aac tgg agt tgc agc tct     307
Asp Ala Leu Glu Glu Ser Leu Lys Leu Lys Asn Trp Ser Cys Ser Ser
                40                  45                  50 cct gtc ttc ccc ggg aat tgg gac ctg agg ctt ctc cag gtg agg gag     355
Pro Val Phe Pro Gly Asn Trp Asp Leu Arg Leu Leu Gln Val Arg Glu
            55                  60                  65 cgc cct gtg gcc ttg gag gct gag ctg gcc ctg acg ctg aag gtc ctg     403
Arg Pro Val Ala Leu Glu Ala Glu Leu Ala Leu Thr Leu Lys Val Leu
        70                  75                  80 gag gcc gct gct ggc cca gcc ctg gag gac gtc cta gac cag ccc ctt     451
Glu Ala Ala Ala Gly Pro Ala Leu Glu Asp Val Leu Asp Gln Pro Leu
 85                  90                  95 cac acc ctg cac cac atc ctc tcc cag ctc cag gcc tgt atc cag cct     499
His Thr Leu His His Ile Leu Ser Gln Leu Gln Ala Cys Ile Gln Pro
100                 105                 110                 115 cag ccc aca gca ggg ccc agg ccc cgg ggc cgc ctc cac cac tgg ctg     547
Gln Pro Thr Ala Gly Pro Arg Pro Arg Gly Arg Leu His His Trp Leu
                120                 125                 130 cac cgg ctc cag gag gcc ccc aaa aag gag tcc gct ggc tgc ctg gag     595
His Arg Leu Gln Glu Ala Pro Lys Lys Glu Ser Ala Gly Cys Leu Glu
            135                 140                 145 gca tct gtc acc ttc aac ctc ttc cgc ctc ctc acg cga gac ctc aaa     643
Ala Ser Val Thr Phe Asn Leu Phe Arg Leu Leu Thr Arg Asp Leu Lys
```

```
                   150                 155                 160
tat gtg gcc gat ggg aac ctg tgt ctg aga acg tca acc cac cct gag    691
Tyr Val Ala Asp Gly Asn Leu Cys Leu Arg Thr Ser Thr His Pro Glu
    165                 170                 175 tcc acc tga caccccacac cttatttatg cgctgagccc tactccttcc            740
Ser Thr *
180 ttaatttatt cctctcacc ctttatttat gaagctgcag ccctgactga gacatagggc   800 tgagtttatt gttttacttt tatacattat gcacaaataa acaacaagga attgga      856

<210> SEQ ID NO 20
<211> LENGTH: 200
<212> TYPE: PRT
<213> ORGANISM: Homo sapiens
<220> FEATURE:
<221> NAME/KEY: SIGNAL
<222> LOCATION: (1)...(19)

<400> SEQUENCE: 20

Met Ala Ala Ala Trp Thr Val Val Thr Leu Val Leu Gly Leu
              -15                 -10                 -5

Ala Val Ala Gly Pro Val Pro Thr Ser Lys Pro Thr Thr Gly Lys
              1                   5                   10

Gly Cys His Ile Gly Arg Phe Lys Ser Leu Ser Pro Gln Glu Leu Ala
        15                  20                  25

Ser Phe Lys Lys Ala Arg Asp Ala Leu Glu Glu Ser Leu Lys Leu Lys
30                  35                  40                  45

Asn Trp Ser Cys Ser Ser Pro Val Phe Pro Gly Asn Trp Asp Leu Arg
                50                  55                  60

Leu Leu Gln Val Arg Glu Arg Pro Val Ala Leu Glu Ala Glu Leu Ala
            65                  70                  75

Leu Thr Leu Lys Val Leu Glu Ala Ala Ala Gly Pro Ala Leu Glu Asp
        80                  85                  90

Val Leu Asp Gln Pro Leu His Thr Leu His His Ile Leu Ser Gln Leu
    95                  100                 105

Gln Ala Cys Ile Gln Pro Gln Pro Thr Ala Gly Pro Arg Pro Arg Gly
110                 115                 120                 125

Arg Leu His His Trp Leu His Arg Leu Gln Glu Ala Pro Lys Lys Glu
                130                 135                 140

Ser Ala Gly Cys Leu Glu Ala Ser Val Thr Phe Asn Leu Phe Arg Leu
            145                 150                 155

Leu Thr Arg Asp Leu Lys Tyr Val Ala Asp Gly Asn Leu Cys Leu Arg
        160                 165                 170

Thr Ser Thr His Pro Glu Ser Thr
    175                 180

<210> SEQ ID NO 21
<211> LENGTH: 734
<212> TYPE: DNA
<213> ORGANISM: Homo sapiens
<220> FEATURE:
<221> NAME/KEY: sig_peptide
<222> LOCATION: (53)...(127)
<220> FEATURE:
<221> NAME/KEY: mat_peptide
<222> LOCATION: (128)...(655)
<220> FEATURE:
<221> NAME/KEY: CDS
<222> LOCATION: (53)...(655)

<400> SEQUENCE: 21
```

```
tgggtgacag cctcagagtg tttcttctgc tgacaaagac cagagatcag ga atg aaa       58
                                                          Met Lys
                                                          -25 cta gac atg acc ggg gac tgc atg cca gtg ctg gtg ctg atg gcc gca        106
Leu Asp Met Thr Gly Asp Cys Met Pro Val Leu Val Leu Met Ala Ala
        -20                 -15                 -10 gtg ctg acc gtg act gga gca gtt cct gtc gcc agg ctc cgc ggg gct        154
Val Leu Thr Val Thr Gly Ala Val Pro Val Ala Arg Leu Arg Gly Ala
         -5                   1                   5 ctc ccg gat gca agg ggc tgc cac ata gcc cag ttc aag tcc ctg tct        202
Leu Pro Asp Ala Arg Gly Cys His Ile Ala Gln Phe Lys Ser Leu Ser
 10                  15                  20                  25 cca cag gag ctg cag gcc ttt aag agg gcc aaa gat gcc tta gaa gag        250
Pro Gln Glu Leu Gln Ala Phe Lys Arg Ala Lys Asp Ala Leu Glu Glu
             30                  35                  40 tcg ctt ctg ctg aag gac tgc aag tgc cgc tcc cgc ctc ttc ccc agg        298
Ser Leu Leu Leu Lys Asp Cys Lys Cys Arg Ser Arg Leu Phe Pro Arg
                 45                  50                  55 acc tgg gac ctg agg cag ctg cag gtg agg gag cgc ccc gtg gct ttg        346
Thr Trp Asp Leu Arg Gln Leu Gln Val Arg Glu Arg Pro Val Ala Leu
                     60                  65                  70 gag gct gag ctg gcc ctg acg ctg aag gtt ctg gag gcc acc gct gac        394
Glu Ala Glu Leu Ala Leu Thr Leu Lys Val Leu Glu Ala Thr Ala Asp
 75                  80                  85 act gac cca gcc ctg ggg gat gtc ttg gac cag ccc ctt cac acc ctg        442
Thr Asp Pro Ala Leu Gly Asp Val Leu Asp Gln Pro Leu His Thr Leu
             90                  95                 100                 105 cac cat atc ctc tcc cag ctc cgg gcc tgt atc cag cct cag ccc acg        490
His His Ile Leu Ser Gln Leu Arg Ala Cys Ile Gln Pro Gln Pro Thr
                110                 115                 120 gca ggg ccc agg acc cgg ggc cgc ctc cac cat tgg ctg cac cgg ctc        538
Ala Gly Pro Arg Thr Arg Gly Arg Leu His His Trp Leu His Arg Leu
                    125                 130                 135 cag gag gcc cca aaa aag gag tcc cct ggc tgc ctc gag gcc tct gtc        586
Gln Glu Ala Pro Lys Lys Glu Ser Pro Gly Cys Leu Glu Ala Ser Val
                        140                 145                 150 acc ttc aac ctc ttc cgc ctc ctc acg cga gac ctg aat tgt gtt gcc        634
Thr Phe Asn Leu Phe Arg Leu Leu Thr Arg Asp Leu Asn Cys Val Ala
 155                 160                 165 agc ggg gac ctg tgt gtc tga cccttccgcc agtcatgcaa cctgagattt          685
Ser Gly Asp Leu Cys Val  *
170                 175 tatttataaa ttagccactt ggcttaattt attgccaccc agtcgctat                  734

<210> SEQ ID NO 22
<211> LENGTH: 200
<212> TYPE: PRT
<213> ORGANISM: Homo sapiens
<220> FEATURE:
<221> NAME/KEY: SIGNAL
<222> LOCATION: (1)...(25)

<400> SEQUENCE: 22

Met Lys Leu Asp Met Thr Gly Asp Cys Met Pro Val Leu Val Leu Met
-25                 -20                 -15                 -10

Ala Ala Val Leu Thr Val Thr Gly Ala Val Pro Val Ala Arg Leu Arg
                 -5                   1                   5

Gly Ala Leu Pro Asp Ala Arg Gly Cys His Ile Ala Gln Phe Lys Ser
         10                  15                  20

Leu Ser Pro Gln Glu Leu Gln Ala Phe Lys Arg Ala Lys Asp Ala Leu
```

```
                    25                  30                  35
Glu Glu Ser Leu Leu Leu Lys Asp Cys Lys Cys Arg Ser Arg Leu Phe
 40                  45                  50                  55

Pro Arg Thr Trp Asp Leu Arg Gln Leu Gln Val Arg Glu Arg Pro Val
                 60                  65                  70

Ala Leu Glu Ala Glu Leu Ala Leu Thr Leu Lys Val Leu Glu Ala Thr
             75                  80                  85

Ala Asp Thr Asp Pro Ala Leu Gly Asp Val Leu Asp Gln Pro Leu His
         90                  95                 100

Thr Leu His His Ile Leu Ser Gln Leu Arg Ala Cys Ile Gln Pro Gln
    105                 110                 115

Pro Thr Ala Gly Pro Arg Thr Arg Gly Arg Leu His His Trp Leu His
120                 125                 130                 135

Arg Leu Gln Glu Ala Pro Lys Lys Glu Ser Pro Gly Cys Leu Glu Ala
                140                 145                 150

Ser Val Thr Phe Asn Leu Phe Arg Leu Leu Thr Arg Asp Leu Asn Cys
            155                 160                 165

Val Ala Ser Gly Asp Leu Cys Val
        170                 175

<210> SEQ ID NO 23
<211> LENGTH: 528
<212> TYPE: DNA
<213> ORGANISM: Artificial Sequence
<220> FEATURE:
<223> OTHER INFORMATION: IL-28A mutant C48S
<220> FEATURE:
<221> NAME/KEY: CDS
<222> LOCATION: (1)...(528)

<400> SEQUENCE: 23 gtt cct gtc gcc agg ctc cac ggg gct ctc ccg gat gca agg ggc tgc      48
Val Pro Val Ala Arg Leu His Gly Ala Leu Pro Asp Ala Arg Gly Cys
 1               5                  10                  15 cac ata gcc cag ttc aag tcc ctg tct cca cag gag ctg cag gcc ttt      96
His Ile Ala Gln Phe Lys Ser Leu Ser Pro Gln Glu Leu Gln Ala Phe
             20                  25                  30 aag agg gcc aaa gat gcc tta gaa gag tcg ctt ctg ctg aag gac tcc     144
Lys Arg Ala Lys Asp Ala Leu Glu Glu Ser Leu Leu Leu Lys Asp Ser
         35                  40                  45 agg tgc cac tcc cgc ctc ttc ccc agg acc tgg gac ctg agg cag ctg     192
Arg Cys His Ser Arg Leu Phe Pro Arg Thr Trp Asp Leu Arg Gln Leu
     50                  55                  60 cag gtg agg gag cgc ccc atg gct ttg gag gct gag ctg gcc ctg acg     240
Gln Val Arg Glu Arg Pro Met Ala Leu Glu Ala Glu Leu Ala Leu Thr
 65                  70                  75                  80 ctg aag gtt ctg gag gcc acc gct gac act gac cca gcc ctg gtg gac     288
Leu Lys Val Leu Glu Ala Thr Ala Asp Thr Asp Pro Ala Leu Val Asp
                 85                  90                  95 gtc ttg gac cag ccc ctt cac acc ctg cac cat atc ctc tcc cag ttc     336
Val Leu Asp Gln Pro Leu His Thr Leu His His Ile Leu Ser Gln Phe
            100                 105                 110 cgg gcc tgt atc cag cct cag ccc acg gca ggg ccc agg acc cgg ggc     384
Arg Ala Cys Ile Gln Pro Gln Pro Thr Ala Gly Pro Arg Thr Arg Gly
        115                 120                 125 cgc ctc cac cat tgg ctg tac cgg ctc cag gag gcc cca aaa aag gag     432
Arg Leu His His Trp Leu Tyr Arg Leu Gln Glu Ala Pro Lys Lys Glu
    130                 135                 140 tcc cct ggc tgc ctc gag gcc tct gtc acc ttc aac ctc ttc cgc ctc     480
Ser Pro Gly Cys Leu Glu Ala Ser Val Thr Phe Asn Leu Phe Arg Leu
```

```
                145                 150                 155                 160
ctc acg cga gac ctg aat tgt gtt gcc agt ggg gac ctg tgt gtc tga       528
Leu Thr Arg Asp Leu Asn Cys Val Ala Ser Gly Asp Leu Cys Val  *
                165                 170                 175
```

<210> SEQ ID NO 24
<211> LENGTH: 175
<212> TYPE: PRT
<213> ORGANISM: Artificial Sequence
<220> FEATURE:
<223> OTHER INFORMATION: IL-28A mutant C48S

<400> SEQUENCE: 24

```
Val Pro Val Ala Arg Leu His Gly Ala Leu Pro Asp Ala Arg Gly Cys
 1               5                  10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Ser
        35                  40                  45

Arg Cys His Ser Arg Leu Phe Pro Arg Thr Trp Asp Leu Arg Gln Leu
    50                  55                  60

Gln Val Arg Glu Arg Pro Met Ala Leu Glu Ala Glu Leu Ala Leu Thr
65                  70                  75                  80

Leu Lys Val Leu Glu Ala Thr Ala Asp Thr Asp Pro Ala Leu Val Asp
                85                  90                  95

Val Leu Asp Gln Pro Leu His Thr Leu His His Ile Leu Ser Gln Phe
            100                 105                 110

Arg Ala Cys Ile Gln Pro Gln Pro Thr Ala Gly Pro Arg Thr Arg Gly
        115                 120                 125

Arg Leu His His Trp Leu Tyr Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175
```

<210> SEQ ID NO 25
<211> LENGTH: 531
<212> TYPE: DNA
<213> ORGANISM: Artificial Sequence
<220> FEATURE:
<223> OTHER INFORMATION: met IL-28A mutant C49S
<220> FEATURE:
<221> NAME/KEY: CDS
<222> LOCATION: (1)...(531)

<400> SEQUENCE: 25

```
atg gtt cct gtc gcc agg ctc cac ggg gct ctc ccg gat gca agg ggc        48
Met Val Pro Val Ala Arg Leu His Gly Ala Leu Pro Asp Ala Arg Gly
 1               5                  10                  15 tgc cac ata gcc cag ttc aag tcc ctg tct cca cag gag ctg cag gcc        96
Cys His Ile Ala Gln Phe Lys Ser Leu Ser Pro Gln Glu Leu Gln Ala
            20                  25                  30 ttt aag agg gcc aaa gat gcc tta gaa gag tcg ctt ctg ctg aag gac       144
Phe Lys Arg Ala Lys Asp Ala Leu Glu Glu Ser Leu Leu Leu Lys Asp
        35                  40                  45 tcc agg tgc cac tcc cgc ctc ttc ccc agg acc tgg gac ctg agg cag       192
Ser Arg Cys His Ser Arg Leu Phe Pro Arg Thr Trp Asp Leu Arg Gln
    50                  55                  60 ctg cag gtg agg gag cgc ccc atg gct ttg gag gct gag ctg gcc ctg       240
Leu Gln Val Arg Glu Arg Pro Met Ala Leu Glu Ala Glu Leu Ala Leu
```

```
                                     65                  70                  75                  80
acg ctg aag gtt ctg gag gcc acc gct gac act gac cca gcc ctg gtg                     288
Thr Leu Lys Val Leu Glu Ala Thr Ala Asp Thr Asp Pro Ala Leu Val
                    85                  90                  95 gac gtc ttg gac cag ccc ctt cac acc ctg cac cat atc ctc tcc cag                     336
Asp Val Leu Asp Gln Pro Leu His Thr Leu His His Ile Leu Ser Gln
                100                 105                 110 ttc cgg gcc tgt atc cag cct cag ccc acg gca ggg ccc agg acc cgg                     384
Phe Arg Ala Cys Ile Gln Pro Gln Pro Thr Ala Gly Pro Arg Thr Arg
            115                 120                 125 ggc cgc ctc cac cat tgg ctg tac cgg ctc cag gag gcc cca aaa aag                     432
Gly Arg Leu His His Trp Leu Tyr Arg Leu Gln Glu Ala Pro Lys Lys
        130                 135                 140 gag tcc cct ggc tgc ctc gag gcc tct gtc acc ttc aac ctc ttc cgc                     480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc                     528
Leu Leu Thr Arg Asp Leu Asn Cys Val Ala Ser Gly Asp Leu Cys Val
                165                 170                 175 tga                                                                                  531
 *
```

<210> SEQ ID NO 26
<211> LENGTH: 176
<212> TYPE: PRT
<213> ORGANISM: Artificial Sequence
<220> FEATURE:
<223> OTHER INFORMATION: met IL-28A mutant C49S

<400> SEQUENCE: 26

Met Val Pro Val Ala Arg Leu His Gly Ala Leu Pro Asp Ala Arg Gly
 1               5                  10                  15

Cys His Ile Ala Gln Phe Lys Ser Leu Ser Pro Gln Glu Leu Gln Ala
                20                  25                  30

Phe Lys Arg Ala Lys Asp Ala Leu Glu Glu Ser Leu Leu Leu Lys Asp
            35                  40                  45

Ser Arg Cys His Ser Arg Leu Phe Pro Arg Thr Trp Asp Leu Arg Gln
        50                  55                  60

Leu Gln Val Arg Glu Arg Pro Met Ala Leu Glu Ala Glu Leu Ala Leu
65                  70                  75                  80

Thr Leu Lys Val Leu Glu Ala Thr Ala Asp Thr Asp Pro Ala Leu Val
                85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
    130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 27
<211> LENGTH: 528
<212> TYPE: DNA
<213> ORGANISM: Artificial Sequence
<220> FEATURE:
<223> OTHER INFORMATION: IL-28A mutant C50S
<220> FEATURE:

```
<221> NAME/KEY: CDS
<222> LOCATION: (1)...(528)

<400> SEQUENCE: 27 gtt cct gtc gcc agg ctc cac ggg gct ctc ccg gat gca agg ggc tgc      48
Val Pro Val Ala Arg Leu His Gly Ala Leu Pro Asp Ala Arg Gly Cys
 1               5                  10                  15 cac ata gcc cag ttc aag tcc ctg tct cca cag gag ctg cag gcc ttt      96
His Ile Ala Gln Phe Lys Ser Leu Ser Pro Gln Glu Leu Gln Ala Phe
             20                  25                  30 aag agg gcc aaa gat gcc tta gaa gag tcg ctt ctg ctg aag gac tgc     144
Lys Arg Ala Lys Asp Ala Leu Glu Glu Ser Leu Leu Leu Lys Asp Cys
         35                  40                  45 agg tcc cac tcc cgc ctc ttc ccc agg acc tgg gac ctg agg cag ctg     192
Arg Ser His Ser Arg Leu Phe Pro Arg Thr Trp Asp Leu Arg Gln Leu
     50                  55                  60 cag gtg agg gag cgc ccc atg gct ttg gag gct gag ctg gcc ctg acg     240
Gln Val Arg Glu Arg Pro Met Ala Leu Glu Ala Glu Leu Ala Leu Thr
 65                  70                  75                  80 ctg aag gtt ctg gag gcc acc gct gac act gac cca gcc ctg gtg gac     288
Leu Lys Val Leu Glu Ala Thr Ala Asp Thr Asp Pro Ala Leu Val Asp
                 85                  90                  95 gtc ttg gac cag ccc ctt cac acc ctg cac cat atc ctc tcc cag ttc     336
Val Leu Asp Gln Pro Leu His Thr Leu His His Ile Leu Ser Gln Phe
            100                 105                 110 cgg gcc tgt atc cag cct cag ccc acg gca ggg ccc agg acc cgg ggc     384
Arg Ala Cys Ile Gln Pro Gln Pro Thr Ala Gly Pro Arg Thr Arg Gly
        115                 120                 125 cgc ctc cac cat tgg ctg tac cgg ctc cag gag gcc cca aaa aag gag     432
Arg Leu His His Trp Leu Tyr Arg Leu Gln Glu Ala Pro Lys Lys Glu
    130                 135                 140 tcc cct ggc tgc ctc gag gcc tct gtc acc ttc aac ctc ttc cgc ctc     480
Ser Pro Gly Cys Leu Glu Ala Ser Val Thr Phe Asn Leu Phe Arg Leu
145                 150                 155                 160 ctc acg cga gac ctg aat tgt gtt gcc agt ggg gac ctg tgt gtc tga    528
Leu Thr Arg Asp Leu Asn Cys Val Ala Ser Gly Asp Leu Cys Val *
                165                 170                 175

<210> SEQ ID NO 28
<211> LENGTH: 175
<212> TYPE: PRT
<213> ORGANISM: Artificial Sequence
<220> FEATURE:
<223> OTHER INFORMATION: IL-28A mutant C50S

<400> SEQUENCE: 28

Val Pro Val Ala Arg Leu His Gly Ala Leu Pro Asp Ala Arg Gly Cys
 1               5                  10                  15

His Ile Ala Gln Phe Lys Ser Leu Ser Pro Gln Glu Leu Gln Ala Phe
             20                  25                  30

Lys Arg Ala Lys Asp Ala Leu Glu Glu Ser Leu Leu Leu Lys Asp Cys
         35                  40                  45

Arg Ser His Ser Arg Leu Phe Pro Arg Thr Trp Asp Leu Arg Gln Leu
     50                  55                  60

Gln Val Arg Glu Arg Pro Met Ala Leu Glu Ala Glu Leu Ala Leu Thr
 65                  70                  75                  80

Leu Lys Val Leu Glu Ala Thr Ala Asp Thr Asp Pro Ala Leu Val Asp
                 85                  90                  95

Val Leu Asp Gln Pro Leu His Thr Leu His His Ile Leu Ser Gln Phe
            100                 105                 110
```

```
        Arg Ala Cys Ile Gln Pro Gln Pro Thr Ala Gly Pro Arg Thr Arg Gly
                    115                 120                 125

Arg Leu His His Trp Leu Tyr Arg Leu Gln Glu Ala Pro Lys Lys Glu
                    130                 135                 140

Ser Pro Gly Cys Leu Glu Ala Ser Val Thr Phe Asn Leu Phe Arg Leu
        145                 150                 155                 160

Leu Thr Arg Asp Leu Asn Cys Val Ala Ser Gly Asp Leu Cys Val
                        165                 170                 175

<210> SEQ ID NO 29
<211> LENGTH: 531
<212> TYPE: DNA
<213> ORGANISM: Artificial Sequence
<220> FEATURE:
<223> OTHER INFORMATION: met IL-28A mutant C51S
<220> FEATURE:
<221> NAME/KEY: CDS
<222> LOCATION: (1)...(531)

<400> SEQUENCE: 29 atg gtt cct gtc gcc agg ctc cac ggg gct ctc ccg gat gca agg ggc     48
Met Val Pro Val Ala Arg Leu His Gly Ala Leu Pro Asp Ala Arg Gly
1               5                   10                  15 tgc cac ata gcc cag ttc aag tcc ctg tct cca cag gag ctg cag gcc     96
Cys His Ile Ala Gln Phe Lys Ser Leu Ser Pro Gln Glu Leu Gln Ala
                20                  25                  30 ttt aag agg gcc aaa gat gcc tta gaa gag tcg ctt ctg ctg aag gac    144
Phe Lys Arg Ala Lys Asp Ala Leu Glu Glu Ser Leu Leu Leu Lys Asp
            35                  40                  45 tgc agg tcc cac tcc cgc ctc ttc ccc agg acc tgg gac ctg agg cag    192
Cys Arg Ser His Ser Arg Leu Phe Pro Arg Thr Trp Asp Leu Arg Gln
        50                  55                  60 ctg cag gtg agg gag cgc ccc atg gct ttg gag gct gag ctg gcc ctg    240
Leu Gln Val Arg Glu Arg Pro Met Ala Leu Glu Ala Glu Leu Ala Leu
65                  70                  75                  80 acg ctg aag gtt ctg gag gcc acc gct gac act gac cca gcc ctg gtg    288
Thr Leu Lys Val Leu Glu Ala Thr Ala Asp Thr Asp Pro Ala Leu Val
                85                  90                  95 gac gtc ttg gac cag ccc ctt cac acc ctg cac cat atc ctc tcc cag    336
Asp Val Leu Asp Gln Pro Leu His Thr Leu His His Ile Leu Ser Gln
            100                 105                 110 ttc cgg gcc tgt atc cag cct cag ccc acg gca ggc ccc agg acc cgg    384
Phe Arg Ala Cys Ile Gln Pro Gln Pro Thr Ala Gly Pro Arg Thr Arg
        115                 120                 125 ggc cgc ctc cac cat tgg ctg tac cgg ctc cag gag gcc cca aaa aag    432
Gly Arg Leu His His Trp Leu Tyr Arg Leu Gln Glu Ala Pro Lys Lys
130                 135                 140 gag tcc cct ggc tgc ctc gag gcc tct gtc acc ttc aac ctc ttc cgc    480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc    528
Leu Leu Thr Arg Asp Leu Asn Cys Val Ala Ser Gly Asp Leu Cys Val
                165                 170                 175 tga                                                                531
 *

<210> SEQ ID NO 30
<211> LENGTH: 176
<212> TYPE: PRT
<213> ORGANISM: Artificial Sequence
<220> FEATURE:
<223> OTHER INFORMATION: met IL-28A mutant C51S
```

-continued

<400> SEQUENCE: 30

```
Met Val Pro Val Ala Arg Leu His Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Cys Arg Ser His Ser Arg Leu Phe Pro Arg Thr Trp Asp Leu Arg Gln
50                  55                  60

Leu Gln Val Arg Glu Arg Pro Met Ala Leu Glu Ala Glu Leu Ala Leu
65                  70                  75                  80

Thr Leu Lys Val Leu Glu Ala Thr Ala Asp Thr Asp Pro Ala Leu Val
                85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 31
<211> LENGTH: 546
<212> TYPE: DNA
<213> ORGANISM: Artificial Sequence
<220> FEATURE:
<223> OTHER INFORMATION: IL-29 mutant C171S
<220> FEATURE:
<221> NAME/KEY: CDS
<222> LOCATION: (1)...(546)

<400> SEQUENCE: 31 ggt ccg gtt ccg acc tct aaa cca acc acc act ggt aaa ggt tgc cac      48
Gly Pro Val Pro Thr Ser Lys Pro Thr Thr Thr Gly Lys Gly Cys His
1               5                   10                  15 atc ggt cgt ttc aaa tct ctg tct ccg cag gaa ctg gct tct ttc aaa      96
Ile Gly Arg Phe Lys Ser Leu Ser Pro Gln Glu Leu Ala Ser Phe Lys
            20                  25                  30 aaa gct cgt gac gct ctg gaa gaa tct ctg aaa ctg aaa aac tgg tct     144
Lys Ala Arg Asp Ala Leu Glu Glu Ser Leu Lys Leu Lys Asn Trp Ser
        35                  40                  45 tgc tct tct ccg gtt ttc ccg ggt aac tgg gat ctg cgt ctg ctg cag     192
Cys Ser Ser Pro Val Phe Pro Gly Asn Trp Asp Leu Arg Leu Leu Gln
50                  55                  60 gtt cgt gaa cgt ccg gtt gct ctg gaa gct gaa ctg gct ctg acc ctg     240
Val Arg Glu Arg Pro Val Ala Leu Glu Ala Glu Leu Ala Leu Thr Leu
65                  70                  75                  80 aaa gtt ctg gaa gct gct gca ggt cct gct ctg gaa gat gtt ctg gat     288
Lys Val Leu Glu Ala Ala Ala Gly Pro Ala Leu Glu Asp Val Leu Asp
                85                  90                  95 cag ccg ctg cac act ctg cac cac atc ctg tct cag ctg cag gct tgc     336
Gln Pro Leu His Thr Leu His His Ile Leu Ser Gln Leu Gln Ala Cys
            100                 105                 110 att caa ccg caa ccg acc gct ggt ccg cgt ccg cgt ggt cgt ctg cac     384
Ile Gln Pro Gln Pro Thr Ala Gly Pro Arg Pro Arg Gly Arg Leu His
        115                 120                 125
```

```
cac tgg ctg cat cgt ctg cag gaa gct ccg aaa aaa gaa tct gct ggt      432
His Trp Leu His Arg Leu Gln Glu Ala Pro Lys Lys Glu Ser Ala Gly
    130                 135                 140 tgc ctg gaa gct tct gtt acc ttc aac ctg ttc cgt ctg ctg acc cgt      480
Cys Leu Glu Ala Ser Val Thr Phe Asn Leu Phe Arg Leu Leu Thr Arg
145                 150                 155                 160 gat ctg aaa tac gtt gct gat ggt aac ctg tct ctg cgt acc tct acc      528
Asp Leu Lys Tyr Val Ala Asp Gly Asn Leu Ser Leu Arg Thr Ser Thr
                165                 170                 175 cat ccg gaa tct acc taa                                              546
His Pro Glu Ser Thr *
            180

<210> SEQ ID NO 32
<211> LENGTH: 181
<212> TYPE: PRT
<213> ORGANISM: Artificial Sequence
<220> FEATURE:
<223> OTHER INFORMATION: IL-29 mutant C171S

<400> SEQUENCE: 32

Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Ser Leu Arg Thr Ser Thr
                165                 170                 175

His Pro Glu Ser Thr
            180

<210> SEQ ID NO 33
<211> LENGTH: 549
<212> TYPE: DNA
<213> ORGANISM: Artificial Sequence
<220> FEATURE:
<223> OTHER INFORMATION: met IL-29 mutant C172S
<220> FEATURE:
<221> NAME/KEY: CDS
<222> LOCATION: (1)...(549)

<400> SEQUENCE: 33 atg ggt ccg gtt ccg acc tct aaa cca acc acc act ggt aaa ggt tgc      48
Met Gly Pro Val Pro Thr Ser Lys Pro Thr Thr Thr Gly Lys Gly Cys
1               5                   10                  15 cac atc ggt cgt ttc aaa tct ctg tct ccg cag gaa ctg gct tct ttc      96
```

```
His Ile Gly Arg Phe Lys Ser Leu Ser Pro Gln Glu Leu Ala Ser Phe
             20                  25                  30 aaa aaa gct cgt gac gct ctg gaa gaa tct ctg aaa ctg aaa aac tgg    144
Lys Lys Ala Arg Asp Ala Leu Glu Glu Ser Leu Lys Leu Lys Asn Trp
         35                  40                  45 tct tgc tct tct ccg gtt ttc ccg ggt aac tgg gat ctg cgt ctg ctg    192
Ser Cys Ser Ser Pro Val Phe Pro Gly Asn Trp Asp Leu Arg Leu Leu
     50                  55                  60 cag gtt cgt gaa cgt ccg gtt gct ctg gaa gct gaa ctg gct ctg acc    240
Gln Val Arg Glu Arg Pro Val Ala Leu Glu Ala Glu Leu Ala Leu Thr
 65                  70                  75                  80 ctg aaa gtt ctg gaa gct gct gca ggt cct gct ctg gaa gat gtt ctg    288
Leu Lys Val Leu Glu Ala Ala Ala Gly Pro Ala Leu Glu Asp Val Leu
                 85                  90                  95 gat cag ccg ctg cac act ctg cac cac atc ctg tct cag ctg cag gct    336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg    384
Cys Ile Gln Pro Gln Pro Thr Ala Gly Pro Arg Pro Arg Gly Arg Leu
        115                 120                 125 cac cac tgg ctg cat cgt ctg cag gaa gct ccg aaa aaa gaa tct gct    432
His His Trp Leu His Arg Leu Gln Glu Ala Pro Lys Lys Glu Ser Ala
    130                 135                 140 ggt tgc ctg gaa gct tct gtt acc ttc aac ctg ttc cgt ctg ctg acc    480
Gly Cys Leu Glu Ala Ser Val Thr Phe Asn Leu Phe Arg Leu Leu Thr
145                 150                 155                 160 cgt gat ctg aaa tac gtt gct gat ggt aac ctg tct ctg cgt acc tct    528
Arg Asp Leu Lys Tyr Val Ala Asp Gly Asn Leu Ser Leu Arg Thr Ser
                165                 170                 175 acc cat ccg gaa tct acc taa                                        549
Thr His Pro Glu Ser Thr *
            180

<210> SEQ ID NO 34
<211> LENGTH: 182
<212> TYPE: PRT
<213> ORGANISM: Artificial Sequence
<220> FEATURE:
<223> OTHER INFORMATION: met IL-29 mutant C172S

<400> SEQUENCE: 34

Met Gly Pro Val Pro Thr Ser Lys Pro Thr Thr Thr Gly Lys Gly Cys
 1               5                  10                  15

His Ile Gly Arg Phe Lys Ser Leu Ser Pro Gln Glu Leu Ala Ser Phe
             20                  25                  30

Lys Lys Ala Arg Asp Ala Leu Glu Glu Ser Leu Lys Leu Lys Asn Trp
         35                  40                  45

Ser Cys Ser Ser Pro Val Phe Pro Gly Asn Trp Asp Leu Arg Leu Leu
     50                  55                  60

Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
                 85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140
```

```
Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Ser Leu Arg Thr Ser
                165                 170                 175

Thr His Pro Glu Ser Thr
            180

<210> SEQ ID NO 35
<211> LENGTH: 531
<212> TYPE: DNA
<213> ORGANISM: Artificial Sequence
<220> FEATURE:
<223> OTHER INFORMATION: met IL-28A
<220> FEATURE:
<221> NAME/KEY: CDS
<222> LOCATION: (1)...(531)

<400> SEQUENCE: 35 atg gtt cct gtc gcc agg ctc cac ggg gct ctc ccg gat gca agg ggc      48
Met Val Pro Val Ala Arg Leu His Gly Ala Leu Pro Asp Ala Arg Gly
 1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
                20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
            35                  40                  45 tgc agg tgc cac tcc cgc ctc ttc ccc agg acc tgg gac ctg agg cag     192
Cys Arg Cys His Ser Arg Leu Phe Pro Arg Thr Trp Asp Leu Arg Gln
        50                  55                  60 ctg cag gtg agg gag cgc ccc atg gct ttg gag gct gag ctg gcc ctg     240
Leu Gln Val Arg Glu Arg Pro Met Ala Leu Glu Ala Glu Leu Ala Leu
 65                 70                  75                  80 acg ctg aag gtt ctg gag gcc acc gct gac act gac cca gcc ctg gtg     288
Thr Leu Lys Val Leu Glu Ala Thr Ala Asp Thr Asp Pro Ala Leu Val
                85                  90                  95 gac gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ttc cgg gcc tgt atc cag cct cag ccc acg gca ggg ccc agg acc cgg     384
Phe Arg Ala Cys Ile Gln Pro Gln Pro Thr Ala Gly Pro Arg Thr Arg
        115                 120                 125 ggc cgc ctc cac cat tgg ctg tac cgg ctc cag gag gcc cca aaa aag     432
Gly Arg Leu His His Trp Leu Tyr Arg Leu Gln Glu Ala Pro Lys Lys
130                 135                 140 gag tcc cct ggc tgc ctc gag gcc tct gtc acc ttc aac ctc ttc cgc     480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc     528
Leu Leu Thr Arg Asp Leu Asn Cys Val Ala Ser Gly Asp Leu Cys Val
                165                 170                 175 tga                                                                  531
 *

<210> SEQ ID NO 36
<211> LENGTH: 176
<212> TYPE: PRT
<213> ORGANISM: Artificial Sequence
<220> FEATURE:
<223> OTHER INFORMATION: met IL-28A

<400> SEQUENCE: 36

Met Val Pro Val Ala Arg Leu His Gly Ala Leu Pro Asp Ala Arg Gly
```

```
                    1               5                  10                  15
               Cys His Ile Ala Gln Phe Lys Ser Leu Ser Pro Gln Glu Leu Gln Ala
                                20                  25                  30

Phe Lys Arg Ala Lys Asp Ala Leu Glu Glu Ser Leu Leu Leu Lys Asp
                                35                  40                  45

Cys Arg Cys His Ser Arg Leu Phe Pro Arg Thr Trp Asp Leu Arg Gln
                50                  55                  60

Leu Gln Val Arg Glu Arg Pro Met Ala Leu Ala Glu Leu Ala Leu
                65                  70                  75                  80

Thr Leu Lys Val Leu Glu Ala Thr Ala Asp Thr Asp Pro Ala Leu Val
                                85                  90                  95

Asp Val Leu Asp Gln Pro Leu His Thr Leu His His Ile Leu Ser Gln
                               100                 105                 110

Phe Arg Ala Cys Ile Gln Pro Gln Pro Thr Ala Gly Pro Arg Thr Arg
                               115                 120                 125

Gly Arg Leu His His Trp Leu Tyr Arg Leu Gln Glu Ala Pro Lys Lys
                               130                 135                 140

Glu Ser Pro Gly Cys Leu Glu Ala Ser Val Thr Phe Asn Leu Phe Arg
                145                 150                 155                 160

Leu Leu Thr Arg Asp Leu Asn Cys Val Ala Ser Gly Asp Leu Cys Val
                               165                 170                 175

<210> SEQ ID NO 37
<211> LENGTH: 621
<212> TYPE: DNA
<213> ORGANISM: Artificial Sequence
<220> FEATURE:
<223> OTHER INFORMATION: met IL-29
<220> FEATURE:
<221> NAME/KEY: CDS
<222> LOCATION: (1)...(549)

<400> SEQUENCE: 37 atg ggc cct gtc ccc act tcc aag ccc acc aca act ggg aag ggc tgc        48
Met Gly Pro Val Pro Thr Ser Lys Pro Thr Thr Thr Gly Lys Gly Cys
 1               5                  10                  15 cac att ggc agg ttc aaa tct ctg tca cca cag gag cta gcg agc ttc        96
His Ile Gly Arg Phe Lys Ser Leu Ser Pro Gln Glu Leu Ala Ser Phe
                20                  25                  30 aag aag gcc agg gac gcc ttg gaa gag tca ctc aag ctg aaa aac tgg       144
Lys Lys Ala Arg Asp Ala Leu Glu Glu Ser Leu Lys Leu Lys Asn Trp
            35                  40                  45 agt tgc agc tct cct gtc ttc ccc ggg aat tgg gac ctg agg ctt ctc       192
Ser Cys Ser Ser Pro Val Phe Pro Gly Asn Trp Asp Leu Arg Leu Leu
        50                  55                  60 cag gtg agg gag cgc cct gtg gcc ttg gag gct gag ctg gcc ctg acg       240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta       288
Leu Lys Val Leu Glu Ala Ala Ala Gly Pro Ala Leu Glu Asp Val Leu
                85                  90                  95 gac cag ccc ctt cac acc ctg cac cac atc ctc tcc cag ctc cag gcc       336
Asp Gln Pro Leu His Thr Leu His His Ile Leu Ser Gln Leu Gln Ala
               100                 105                 110 tgt atc cag cct cag ccc aca gca ggg ccc agg ccc cgg ggc cgc ctc       384
Cys Ile Gln Pro Gln Pro Thr Ala Gly Pro Arg Pro Arg Gly Arg Leu
           115                 120                 125 cac cac tgg ctg cac cgg ctc cag gag gcc ccc aaa aag gag tcc gct       432
His His Trp Leu His Arg Leu Gln Glu Ala Pro Lys Lys Glu Ser Ala
       130                 135                 140
```

```
ggc tgc ctg gag gca tct gtc acc ttc aac ctc ttc cgc ctc ctc acg    480
Gly Cys Leu Glu Ala Ser Val Thr Phe Asn Leu Phe Arg Leu Leu Thr
145                 150                 155                 160 cga gac ctc aaa tat gtg gcc gat ggg aac ctg tgt ctg aga acg tca    528
Arg Asp Leu Lys Tyr Val Ala Asp Gly Asn Leu Cys Leu Arg Thr Ser
                165                 170                 175 acc cac cct gag tcc acc tga cacccacac cttatttatg cgctgagccc        579
Thr His Pro Glu Ser Thr *
            180 tactccttcc ttaatttatt cctctcacc ctttatttat ga                      621

<210> SEQ ID NO 38
<211> LENGTH: 182
<212> TYPE: PRT
<213> ORGANISM: Artificial Sequence
<220> FEATURE:
<223> OTHER INFORMATION: met IL-29

<400> SEQUENCE: 38

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr
            180

<210> SEQ ID NO 39
<211> LENGTH: 531
<212> TYPE: DNA
<213> ORGANISM: Artificial Sequence
<220> FEATURE:
<223> OTHER INFORMATION: met IL-28B
<220> FEATURE:
<221> NAME/KEY: CDS
<222> LOCATION: (1)...(531)

<400> SEQUENCE: 39 atg gtt cct gtc gcc agg ctc cgc ggg gct ctc ccg gat gca agg ggc    48
Met Val Pro Val Ala Arg Leu Arg Gly Ala Leu Pro Asp Ala Arg Gly
1               5                   10                  15 tgc cac ata gcc cag ttc aag tcc ctg tct cca cag gag ctg cag gcc    96
Cys His Ile Ala Gln Phe Lys Ser Leu Ser Pro Gln Glu Leu Gln Ala
```

```
                        20                      25                          30
ttt aag agg gcc aaa gat gcc tta gaa gag tcg ctt ctg ctg aag gac        144
Phe Lys Arg Ala Lys Asp Ala Leu Glu Glu Ser Leu Leu Leu Lys Asp
             35                      40                      45 tgc aag tgc cgc tcc cgc ctc ttc ccc agg acc tgg gac ctg agg cag        192
Cys Lys Cys Arg Ser Arg Leu Phe Pro Arg Thr Trp Asp Leu Arg Gln
 50                      55                      60 ctg cag gtg agg gag cgc ccc gtg gct ttg gag gct gag ctg gcc ctg        240
Leu Gln Val Arg Glu Arg Pro Val Ala Leu Glu Ala Glu Leu Ala Leu
 65                      70                      75                  80 acg ctg aag gtt ctg gag gcc acc gct gac act gac cca gcc ctg ggg        288
Thr Leu Lys Val Leu Glu Ala Thr Ala Asp Thr Asp Pro Ala Leu Gly
                 85                      90                      95 gat gtc ttg gac cag ccc ctt cac acc ctg cac cat atc ctc tcc cag        336
Asp Val Leu Asp Gln Pro Leu His Thr Leu His His Ile Leu Ser Gln
             100                     105                     110 ctc cgg gcc tgt atc cag cct cag ccc acg gca ggg ccc agg acc cgg        384
Leu Arg Ala Cys Ile Gln Pro Gln Pro Thr Ala Gly Pro Arg Thr Arg
         115                     120                     125 ggc cgc ctc cac cat tgg ctg cac cgg ctc cag gag gcc cca aaa aag        432
Gly Arg Leu His His Trp Leu His Arg Leu Gln Glu Ala Pro Lys Lys
 130                     135                     140 gag tcc cct ggc tgc ctc gag gcc tct gtc acc ttc aac ctc ttc cgc        480
Glu Ser Pro Gly Cys Leu Glu Ala Ser Val Thr Phe Asn Leu Phe Arg
145                     150                     155                 160 ctc ctc acg cga gac ctg aat tgt gtt gcc agc ggg gac ctg tgt gtc        528
Leu Leu Thr Arg Asp Leu Asn Cys Val Ala Ser Gly Asp Leu Cys Val
                 165                     170                     175 tga                                                                    531
 *
```

<210> SEQ ID NO 40
<211> LENGTH: 176
<212> TYPE: PRT
<213> ORGANISM: Artificial Sequence
<220> FEATURE:
<223> OTHER INFORMATION: met IL-28B

<400> SEQUENCE: 40

```
Met Val Pro Val Ala Arg Leu Arg Gly Ala Leu Pro Asp Ala Arg Gly
 1               5                   10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Cys Lys Cys Arg Ser Arg Leu Phe Pro Arg Thr Trp Asp Leu Arg Gln
     50                  55                  60

Leu Gln Val Arg Glu Arg Pro Val Ala Leu Glu Ala Glu Leu Ala Leu
 65                  70                  75                  80

Thr Leu Lys Val Leu Glu Ala Thr Ala Asp Thr Asp Pro Ala Leu Gly
                 85                  90                  95

Asp Val Leu Asp Gln Pro Leu His Thr Leu His His Ile Leu Ser Gln
             100                 105                 110

Leu Arg Ala Cys Ile Gln Pro Gln Pro Thr Ala Gly Pro Arg Thr Arg
         115                 120                 125

Gly Arg Leu His His Trp Leu His Arg Leu Gln Glu Ala Pro Lys Lys
     130                 135                 140

Glu Ser Pro Gly Cys Leu Glu Ala Ser Val Thr Phe Asn Leu Phe Arg
145                 150                 155                 160
```

```
Leu Leu Thr Arg Asp Leu Asn Cys Val Ala Ser Gly Asp Leu Cys Val
            165                 170                 175
```